(12) United States Patent
Herzon et al.

(10) Patent No.: US 10,316,037 B1
(45) Date of Patent: Jun. 11, 2019

(54) COMPOUNDS AND METHODS FOR TREATING CANCER

(71) Applicant: YALE UNIVERSITY, New Haven, CT (US)

(72) Inventors: Seth Herzon, Madison, CT (US); Alan Healy, New Haven, CT (US)

(73) Assignee: YALE UNIVERSITY, New Haven, CT (US)

( * ) Notice: Subject to any disclaimer, the term of this patent is extended or adjusted under 35 U.S.C. 154(b) by 0 days.

(21) Appl. No.: 15/799,588

(22) Filed: Oct. 31, 2017

Related U.S. Application Data

(60) Provisional application No. 62/417,563, filed on Nov. 4, 2016.

(51) Int. Cl.
| | | |
|---|---|---|
| C07D 471/04 | (2006.01) | |
| A61P 35/00 | (2006.01) | |
| C07D 519/00 | (2006.01) | |

(52) U.S. Cl.
CPC .......... *C07D 471/04* (2013.01); *A61P 35/00* (2018.01); *C07D 519/00* (2013.01)

(58) Field of Classification Search
CPC .................................................. C07D 471/04
See application file for complete search history.

(56) References Cited

U.S. PATENT DOCUMENTS

| | | |
|---|---|---|
| 4,870,287 A | 9/1989 | Cole et al. |
| 5,091,313 A | 2/1992 | Change |
| 5,169,939 A | 12/1992 | Gefter et al. |
| 5,202,238 A | 4/1993 | Fell |
| 5,204,244 A | 4/1993 | Fell |
| 5,292,867 A | 3/1994 | Chang |
| 5,760,395 A | 6/1998 | Johnstone |
| 5,824,311 A | 10/1998 | Greene |
| 5,830,880 A | 11/1998 | Sedlacek et al. |
| 5,846,945 A | 12/1998 | McCormick |
| 2010/0284921 A1 | 11/2010 | Gordon et al. |

FOREIGN PATENT DOCUMENTS

| | | |
|---|---|---|
| WO | 89/09622 | 10/1989 |
| WO | 93/21319 | 10/1993 |

OTHER PUBLICATIONS

Pirrung "Handbook of Synthetic Organic Chemistry" Second Edition, Academic Press: San Diego, 2017.*
Dorwald F. A. Side Reactions in Organic Synthesis, 2005, Wiley: VCH, Weinheim p. IX of Preface p. 1-15.*
Healy, "A Mechanistic Model for Colibactin-Induced Genotoxicity" J. Am. Chem. Soc. 2016, 138, 15563-15570.*
Brachmann,"Colibactin biosynthesis and biological activity depend on the rare aminomalonyl polyketide precursor." Chemical Communications 2015, 51(66), 13138-13141 (STN abstract only).*
Zha, "Machinery from the pks Island Facilitates Isolation of a Candidate Precolibactin. Characterization of Polyketide Synthase" ACS Chemical Biology, 2016, 11(5), 1287-1295 Feb. 18, 2016.*
Austin-Ward Ed, Villaseca C. Gene therapy and its applications. Rev med Chile, 1998;126(7):ISSN 0034-9887.
Boulianne GL, et al. Production of functional chimaeric mouse/human antibody. Nature, 1984;312(13):643-646.
Bukowski, et al. Efficacy of Multimodality Therapy in Advanced Renal Cell Carcinoma. Urology, 1998;51:933-937.
Carter PJ, Senter PD. Antibody-Drug Conjugates for Cancer Therapy. Cancer J, 2008;14:154-169.
Christodoulides M, et al. Immunization with recombinant class 1 outer-membrane protein from Neisseria meningitidis: influence of liposomes and adjuvants on antibody avidity, recognition of native protein and the induction of a bactericidal immune response against meningococci. Microbiology, 1998;144:3027-3037.
Davidson NJ, et al. IL-12, But not IFN-gamma, Plays a Major Role in Sustaining the Chronic Phase of Colitis in IL-10-Deficient Mice. The Journal of Immunology, 1998;161:3143-3149.
Goding JW. Monoclonal Antibodies: principles and practice. Academic Press Limited, 24-28 Oval Road, London NW1 7DX, 1996.
Hale G, et al. Remission Induction in Non-Hodgekin Lymphoma with Reshaped Human Monoclonal Antibody Campath-1H. The Lancet, 1988;1394-1399.
Hanibuchi M, et al. Therapeutic Efficacy of Mouse-Human Chimeric Anti-Ganglioside GM2 Monoclonal Antibody Against Multiple Organ Micrometastases of Human Lung Cancer in NK Cell-Depleted SCID Mice. Int. J. Cancer, 1998;78:480-485.
Harlow E, Lane D. Immunoprecipitation: Preclearing the Lysate. CSH Protoc, Sep. 1, 2006;2006(4). pii: pdb. prot4536.
Healy AR, et al. Convergent and Modular Synthesis of Candidate Precolibactins. Structural Revision of Precolibactin A. J Am Chem Soc, 2016;138:5426-5432.
Hellstrand K, et al. Histamine and Cytokine Therapy. Acta Oncologica, 1998:37(4):347-353.
Hollander N. Immunotherapy for B-cell lymphoma: current status and prospective advances. Frontiers in Immunology, 2012;3:Article 3.
Hui GS, Hashimoto CN. Pathways for Potentiation of Immunogenicity during Adjuvant-Assisted Immunizations with Plasmodium falciparum Major Merozoite Surface Protein 1. Infection and Immunity, 1998;66(11):5329-5336.
Jones PT, et al. Replacing the complementarity-determining regions in a human antibody with those from a mouse. Nature, 1986;321:522-525.
Leal M, et al. Antibody-drug conjugates: an emerging modality for the treatment of cancer. Ann NY Acad Sci, 2014;1321:41-54.
Liu AY, et al. Chimeric mouse-human IgG1 antibody that can mediate lysis of cancer cells. Proc Natl Acad Sci, 1987;84:3439-3443.

(Continued)

*Primary Examiner* — David K O'Dell
(74) *Attorney, Agent, or Firm* — Henry D. Coleman; R. Neil Sudol

(57) ABSTRACT

The present invention is directed to novel anticancer compounds which show excellent activity as anticancer agents. The present invention is also directed to pharmaceutical compositions based upon these compounds and methods of treating cancer, including drug resistant, multiple drug resistant, metastatic and recurrent cancer.

25 Claims, 4 Drawing Sheets

(56) References Cited

OTHER PUBLICATIONS

Morrison SL, et al. Chimeric human antibody molecules: Mouse antigen-binding domains with human constant region domains. Proc Natl Acad Sci USA, 1984;81:6851-6855.
Pangborn MC, Mckinney JA. Purification of serologically active phosphoinositides of *Mycobacterium tuberculosis*. Journal of Lipid Research, 1966;7:627-633.
Qin L, et al. Promoter Attenuation in Gene Therapy: Interferon-gamma and Tumor Necrosis Factor-alpha Inhibit Transgene Expression. Human Gene Therapy, 1997;8:2019-2029.
Queen C, et al. A humanized antibody that binds to the interleukin 2 receptor. Proc Natl Acad Sci USA, 1989;86:10029-10033.
Tan LK, et al. A human-mouse chimeric immunoglobulin gene with a human variable region is expressed in mouse myeloma cells. J Immunol, 1985;135:3564-3567.
Tanaka A, Usuki T. Synthesis of the peptide moiety of the jamaicamides. Tetrahedron Letters, 2011;52:5036-5038.
Teicher BA. In Vivo/Ex Vivo and In Situ Assays Used in Cancer Research: A Brief Review. Toxicologic Pathology, 2009;37:114-122.
Teicher BA. Targets in small cell lung cancer. Biochemical Pharmacology, 2014;67:211-219.
Tuszynski GP, et al. Thrombospondin Promotes Platelet Aggregation. Blood, 1988;72:109-115.
Verhoeyen M, et al. Reshaping Human Antibodies: Grafting an Antilysozyme Activity. Science, 1988;239:1534-1536.
Whittle N, et al. Expression in COS cells of a mouse-human chimaeric B72/3 antibody. Protein Engineering, 1987;1 (6):499-505.

\* cited by examiner

Scheme 1

Scheme 2

Table 1

| Best-fit values | Kinamycin | | | | Tamoxifen | | | |
|---|---|---|---|---|---|---|---|---|
| | HeLa | LnCap | K562 | HCT116 | HeLa | LnCap | K562 | HCT116 |
| | | | | | | Ambiguous | Ambiguous | Ambiguous |
| Bottom | 6.9 | 14.1 | 10.2 | 2.8 | 12.5 | 19.5 | 2.0 | 27.3 |
| Top | 103.7 | 101.4 | 100.5 | 105.9 | 101.3 | 99.5 | 99.3 | 100.0 |
| LogEC50 | -8.3 | -7.4 | -7.8 | -8.0 | -5.1 | ~-4.973 | ~-5.003 | ~-5.008 |
| HillSlope | 1.1 | 1.1 | 1.4 | 0.6 | 2.9 | ~12.29 | ~13.23 | ~13.98 |
| EC50 | 5.263E-09 | 4.136E-08 | 1.418E-08 | 9.334E-09 | 0.000008544 | ~1.064e-005 | ~9.926e-006 | ~9.812e-006 |
| Span | 97 | 87 | 90 | 103 | 89 | 80 | 97 | 73 |

Table 2

| | Boc-NH-precoli-OH (16) | | | Boc-NH-precoli-SMe (S4) | | | Boc-NH-precoli-SMe2 (S5) | | |
|---|---|---|---|---|---|---|---|---|---|
| | HeLa | LnCap | K562 | HCT116 | HeLa | LnCap | K562 | HCT116 | HeLa | LnCap | K562 | HCT116 |
| Best-fit values | | | | | | | | | | | | |
| Bottom | - | - | -9.0 | - | - | - | -9.1 | - | - | - | -11.0 | - |
| Top | - | - | 85.2 | - | - | - | 88.9 | - | - | - | 144.4 | - |
| LogEC50 | - | - | -7.5 | - | - | - | -8.0 | - | - | - | -5.3 | - |
| HillSlope | - | - | 1.6 | - | - | - | 1.2 | - | - | - | 0.7 | - |
| EC50 | - | - | 3.533E-08 | - | - | - | 1.117E-08 | - | - | - | 5.415E-06 | - |
| Span | - | - | 94.25 | - | - | - | 97.99 | - | - | - | 155.3 | - |

Boc-NH-precoli-OH - HN-ES6811

Boc-NH-precoli-SMe - HN-ES6814

Curve: Boc-NH-precoli-SMe2 – HN-ES6815

COMPOUNDS AND METHODS FOR TREATING CANCER

RELATED APPLICATIONS

This application claims the benefit of priority of U.S. provisional patent application Ser. No. 62/417,563, filed 4 Nov. 2016 of identical title, the contents of which application is incorporated by reference in its entirety herein.

FIELD OF THE INVENTION

The present invention is directed to novel compounds which show excellent activity as anticancer agents. The present invention is also directed to pharmaceutical compositions based upon these compounds and methods of treating cancer, including drug resistant, multiple drug resistant, metastatic and recurrent cancer.

BACKGROUND OF THE INVENTION

The present invention is directed to compounds according to the chemical structure I:

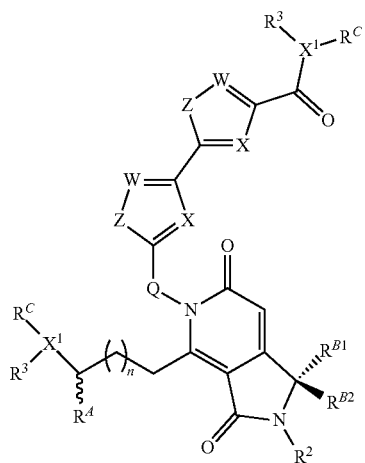

Where X or W is each independently N or C—$R^1$;
Each Z is independently S, O, N—$R^N$ or CR(R);
Each R is independently H, a $C_1$-$C_3$ alkyl group optionally substituted with one or two hydroxyl groups or up to three halogen groups or a O—($C_1$-$C_3$) alkoxy group;
Each $R^N$ is independently H or a $C_1$-$C_3$ alkyl group optionally substituted with one or two hydroxyl groups or up to three halogen groups, preferably H or methyl;
Q is O, S, N($R^1$) or C($R^Q$)$R^Q$;
$X^1$ is O, S, N($R^3$) or C($R^X$)$R^X$;
$R^A$ is H or an optionally substituted $C_1$-$C_8$ alkyl or alkene group, preferably H or a $C_1$-$C_3$ alkyl, most often methyl;
$R^Q$ and $R^X$ are each independently H or a $C_1$-$C_6$ (preferably $C_1$-$C_3$) alkyl group which is optionally substituted with one or two hydroxyl groups or up to three halogen groups;
$R^1$ and $R^2$ are each independently H or a $C_1$-$C_3$ alkyl group which is optionally substituted with one or two hydroxyl groups or up to three halogen groups;
Each $R^3$ when present, is independently H, a $C_1$-$C_6$ alkyl group optionally substituted with 1 or 2 hydroxyl groups or up to three halogen groups (preferably a $C_1$-$C_3$ alkyl group, more preferably methyl), a protecting group $P_G$ or a targeting element $T_E$ which is linked to $X^1$ (preferably a nitrogen) through a linker $L_C$ which is optionally cleavable;
n is 0, 1, 2, 3, or 4, preferably 1, 2 or 3 (more preferably 1);
$R^{B1}$ and $R^{B2}$ are each independently H, a $C_1$-$C_3$ alkyl group which is optionally substituted with one or two hydroxyl groups or up to three halo groups (F, Cl, Br or I, preferably Cl or F, most often F) or together $R^{B1}$ and $R^{B2}$ form a cyclopropyl or cyclobutyl group (preferably, $R^{B1}$ and $R^{B2}$ are each independently H, methyl or together form a cyclopropyl group);
Each $R^C$ is independently H, a $C_1$-$C_{12}$ optionally substituted alkyl or alkene group (preferably substituted with one or two hydroxyl groups, up to five halo groups), a $C_1$-$C_{12}$ (preferably $C_2$-$C_{12}$) optionally substituted acyl or ester group, or a —$(CH_2)_{n1}NR_1R_2$ or a —$(CH_2)_{n1}SR_SR_{S1}$ group where $R_S$ is absent or a $C_1$-$C_6$ optionally substituted alkyl group (preferably $R_S$ is absent or a methyl group—which forms a positive charge on the sulfur group) and $R_1$, $R_2$ and $R_{S1}$ are each independently H or a $C_1$-$C_6$ optionally substituted alkyl group (preferably a methyl group), a protecting group $P_G$ or a targeting element $T_E$ which is linked to the nitrogen or sulfur through a linker $L_C$ which is optionally cleavable, and n1 is 1-8 (preferably 1, 2, 3, 4 or 5), or $R^C$ (preferably no more than one $R^C$) forms a dimer compound through a linker group, the dimer compound according to the general chemical structure(s):

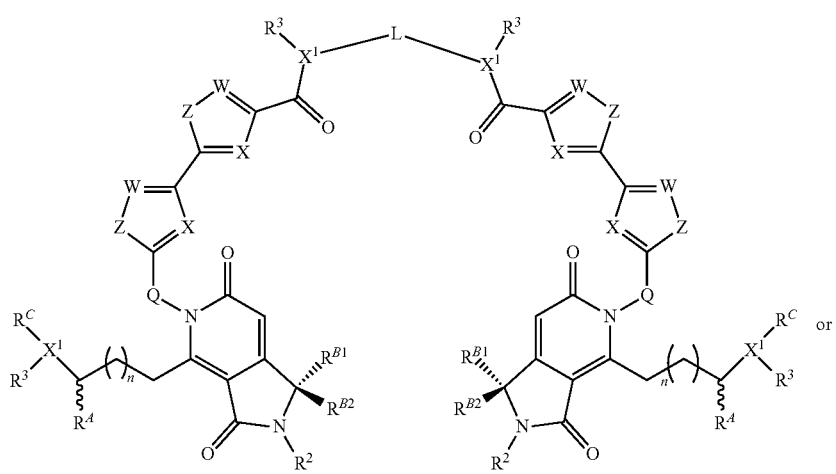

-continued

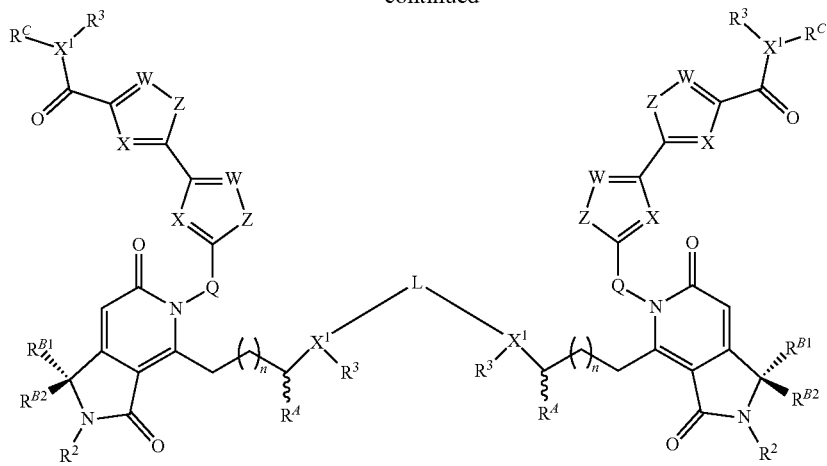

Where each of X, W, Z, $R^2$, $R^3$, $R^A$, n, $R^{B1}$ and $R^{B2}$, $X^1$ and $R^C$ are the same as for compound I above, and L is a linker group which covalently links the dimeric portions of the molecule to each other, or a pharmaceutically acceptable salt, stereoisomer, solvate or polymorph thereof.

In each of the above compounds, X is preferably N; Z is preferably S, O, N—H or N—$CH_3$ (more preferably S); W is preferably C—H, R is preferably H, methyl or OMe; $R^A$ is preferably H or a $C_1$-$C_3$ alkyl, preferably H or methyl; $R^1$ and $R^2$ are each independently preferably H or methyl; $R^3$ is H, methyl, an ester group (oxycarbonyl ester or carboxyester each having a $C_1$-$C_6$ alkyl group, in certain instances a tert-butyl group) a protecting group $P_G$ (preferably a BOC group when $X^1$ is N) or a targeting element $T_E$ which is linked to $X^1$ through an optionally cleavable linker $L_C$, $R^{B1}$ and $R^{B2}$ are each independently H, methyl or together form a cyclopropyl group and $R^C$ is H, methyl, a $C_1$-$C_{12}$ (preferably $C_2$-$C_{12}$) optionally substituted acyl or ester group, a —$(CH_2)_{n1}$—$N(CH_3)_2$ group or a —$(CH_2)_{n1}SR_SR_{S1}$ group where $R_S$ is absent or a $C_1$-$C_6$ optionally substituted alkyl group (preferably $R_S$ is absent or a methyl group—which forms a positive charge on the sulfur group) and $R_1$, $R_2$ and $R_{S1}$ are each independently H or a $C_1$-$C_6$ optionally substituted alkyl group (preferably a methyl group) and n is 1, 2, 3 or 4 (more preferably 2 or 3) or no more than one $R^C$ forms a dimer compound through linker L where L is preferably a —$(CH_2)_mN(R)(CH_2)_m$— group where R is H or a $C_1$-$C_3$ alkyl group (preferably H or methyl) and each m is independently from 1-12 (preferably, 1-10, more preferably 1, 2, 3, 4, 5, or 6).

In another embodiment, the invention is directed to compounds according to the chemical structure:

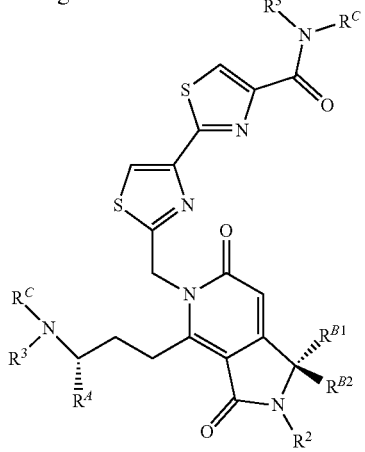

Where $R^A$ is H or an optionally substituted $C_1$-$C_8$ alkyl or alkene group, preferably H or a $C_1$-$C_3$ alkyl, most often methyl;

$R^2$ is H or a $C_1$-$C_3$ alkyl group which is optionally substituted with one or two hydroxyl groups or up to three halogen groups;

Each $R^3$ is independently H, a $C_1$-$C_6$ alkyl group optionally substituted with 1 or 2 hydroxyl groups or up to three halogen groups (preferably a $C_1$-$C_3$ alkyl group), a protecting group $P_G$ or a targeting element $T_E$ which is linked to the adjacent nitrogen through a linker Lc which is optionally cleavable;

$R^{B1}$ and $R^{B2}$ are each independently H, a $C_1$-$C_3$ alkyl group which is optionally substituted with one or two hydroxyl groups or up to three halo groups (F, Cl, Br or I, preferably Cl or F, most often F) or together $R^{B1}$ and $R^{B2}$ form a cyclopropyl or cyclobutyl group (preferably, $R^{B1}$ and $R^{B2}$ are each independently H, methyl or together form a cyclopropyl group);

Each $R^C$ is independently H, a $C_1$-$C_{12}$ optionally substituted alkyl or alkene group (preferably substituted with one or two hydroxyl groups, up to five halo groups), a $C_1$-$C_{12}$ (preferably $C_2$-$C_{12}$) optionally substituted acyl or ester group, or a —$(CH_2)_{n1}NR_1R_2$ or a —$(CH_2)_{n1}SR_SR_{S1}$ group where $R_S$ is absent or a $C_1$-$C_6$ optionally substituted alkyl group (preferably $R_S$ is absent or a methyl group—which forms a positive charge on the sulfur group) and $R_1$, $R_2$ and $R_{S1}$ are each independently H or a $C_1$-$C_6$ optionally substituted alkyl group (preferably a methyl group), a protecting group $P_G$ or a targeting element $T_E$ which is linked to the nitrogen through an optionally cleavable linker $L_C$, and n1 is 1-8 (preferably 1, 2, 3, 4 or 5), or $R^C$ (preferably no more than one $R^C$) forms a dimer compound through a linker group, the dimer compound according to the general chemical structure(s):

a $C_1$-$C_3$ alkyl group (preferably H or methyl) and each m is independently from 1-12 (preferably, 1-10, more preferably 1, 2, 3, 4, 5, or 6), or or a pharmaceutically acceptable salt, stereoisomer, solvate or polymorph thereof.

In another embodiment, preferred compounds according to the present invention include compounds according to the chemical structure:

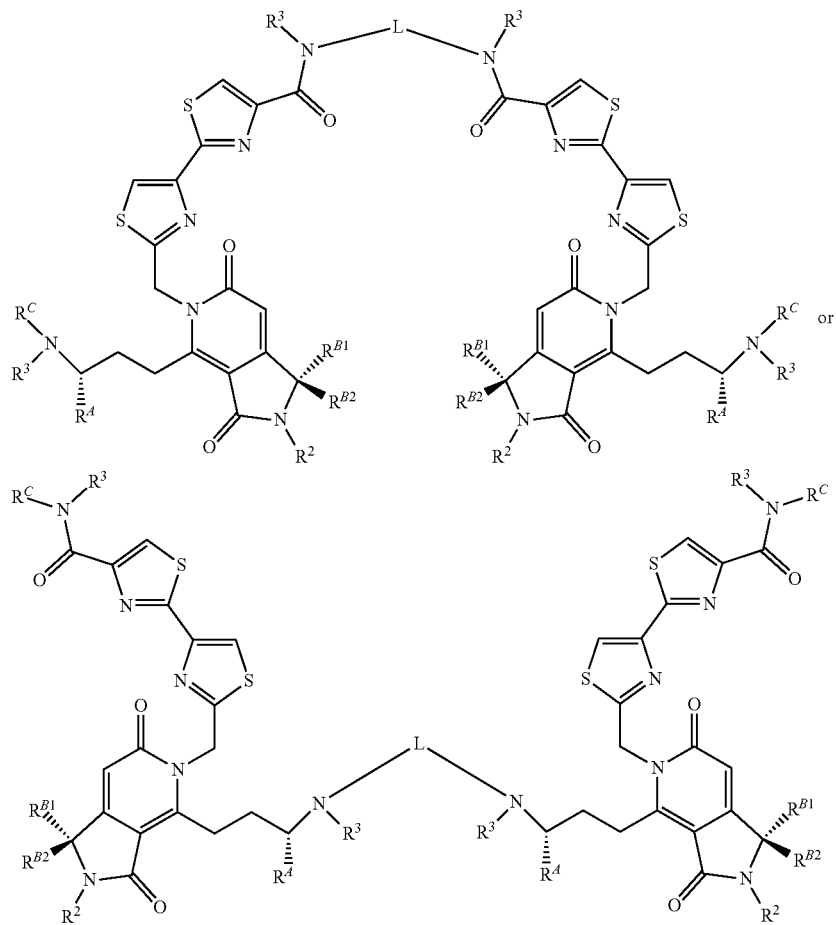

Where $R^A$, $R^2$, $R^3$, $R^{B1}$, $R^{B2}$, and $R^C$ are the same as above. In these compositions $R^A$ is preferably H or a $C_1$-$C_3$ alkyl, preferably H or methyl; $R^2$ is preferably H or methyl; $R^3$ is H, methyl, a protecting group $P_G$ (preferably a BOC group) or a targeting element $T_E$ which is linked to the adjacent nitrogen through an optionally cleavable linker $L_C$, $R^{B1}$ and $R^{B2}$ are each independently H, methyl or together form a cyclopropyl group and $R^C$ is H, methyl, a $C_1$-$C_{12}$ (preferably $C_2$-$C_{12}$) optionally substituted acyl or ester group, a —$(CH_2)_{n1}$—$N(CH_3)_2$ group or a —$(CH_2)_{n1}SR_SR_{S1}$ group where $R_S$ is absent or a $C_1$-$C_6$ optionally substituted alkyl group (preferably $R_S$ is absent or a methyl group—which forms a positive charge on the sulfur group) and $R_1$, $R_2$ and $R_{S1}$ are each independently H or a $C_1$-$C_6$ optionally substituted alkyl group (preferably a methyl group) and n1 is 1, 2, 3 or 4 (more preferably 2 or 3) or one $R^C$ (no more than one $R^C$) forms a dimer compound through linker L where L is preferably a —$(CH_2)_mN(R)(CH_2)_m$— group where R is H or

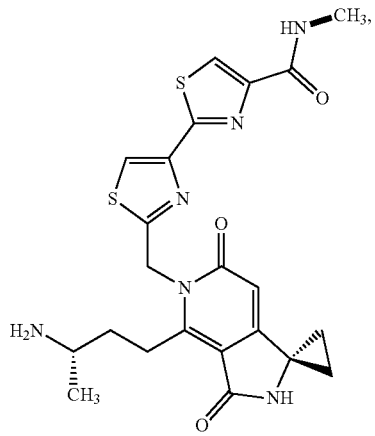

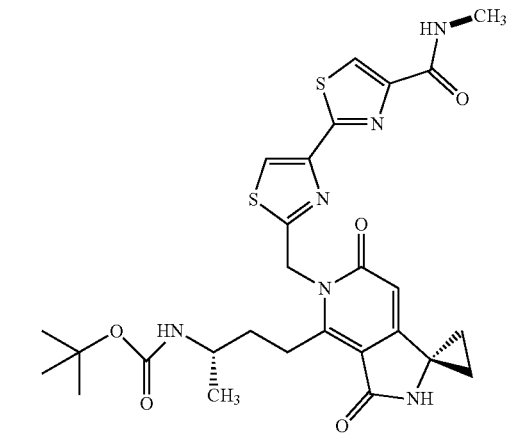
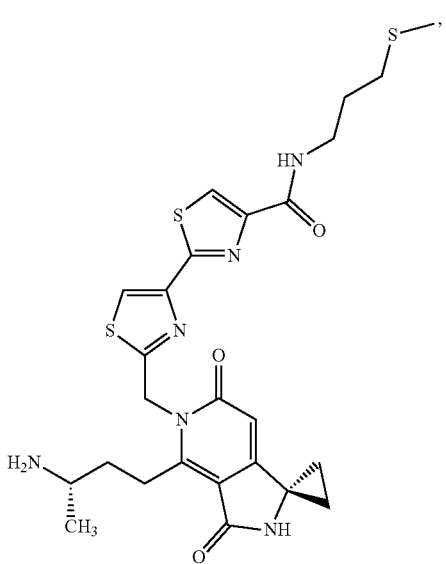
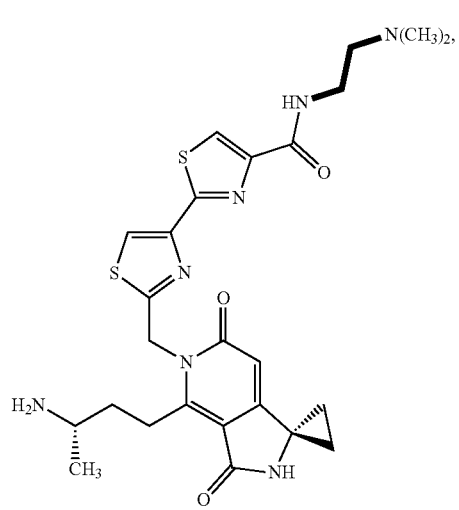
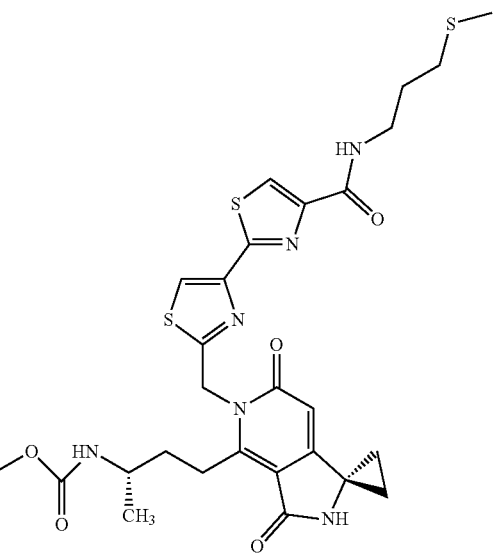
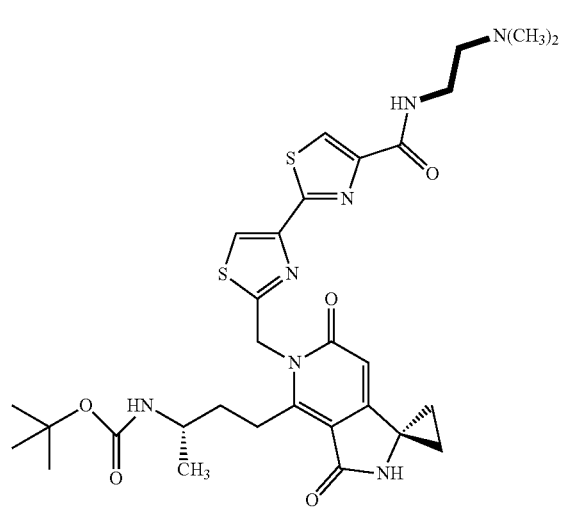
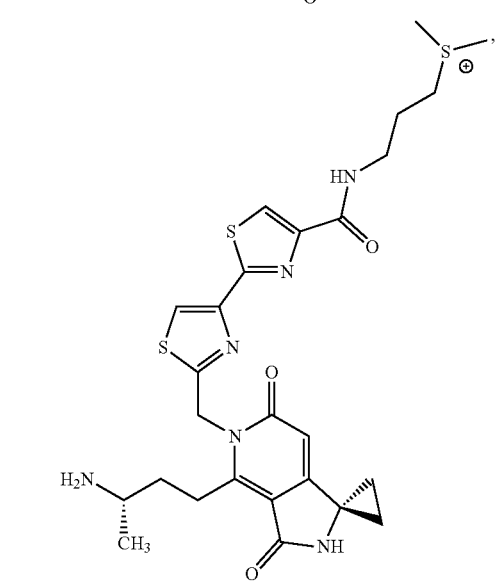

-continued

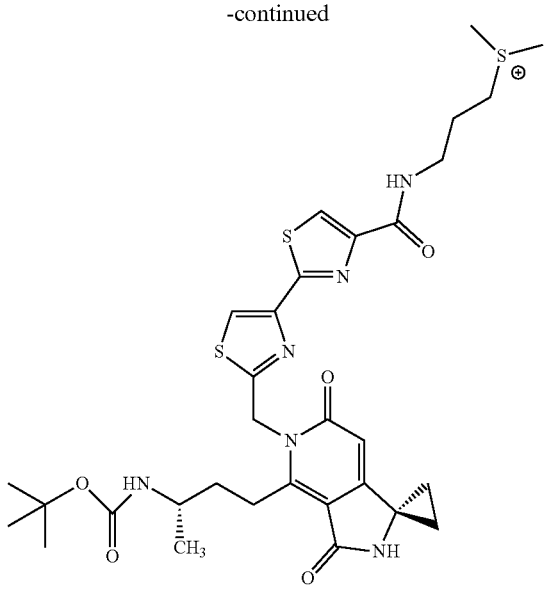

or a pharmaceutically acceptable salt, stereoisomer, solvate or polymorph thereof.

In an alternative embodiment, the present invention is directed to pharmaceutical compositions comprising an effective amount of at least one compound as described above, optionally in combination with at least one additional bioactive agent, preferably at least one additional anticancer agent.

In a further aspect of the invention, compounds according to the present invention are used to treat and/or reduce the likelihood of cancer in a patient in need thereof and to treat or reduce the likelihood that a cancer will metastasize or that a cancer in remission will reoccur (recurrence). The method of treating cancer comprises administering to a patient in need an effective amount of a compound as otherwise described herein in combination with a pharmaceutically acceptable carrier, additive or excipient, optionally in further combination with at least one additional bioactive agent, preferably an agent which is effective in treating cancer, metastatic cancer, recurrent cancer or one or more of its secondary conditions or effects.

Additional embodiments of the present invention are readily gleaned from a review of the Detailed Description of the Invention which Follows.

DETAILED DESCRIPTION OF THE INVENTION

Figure 1:
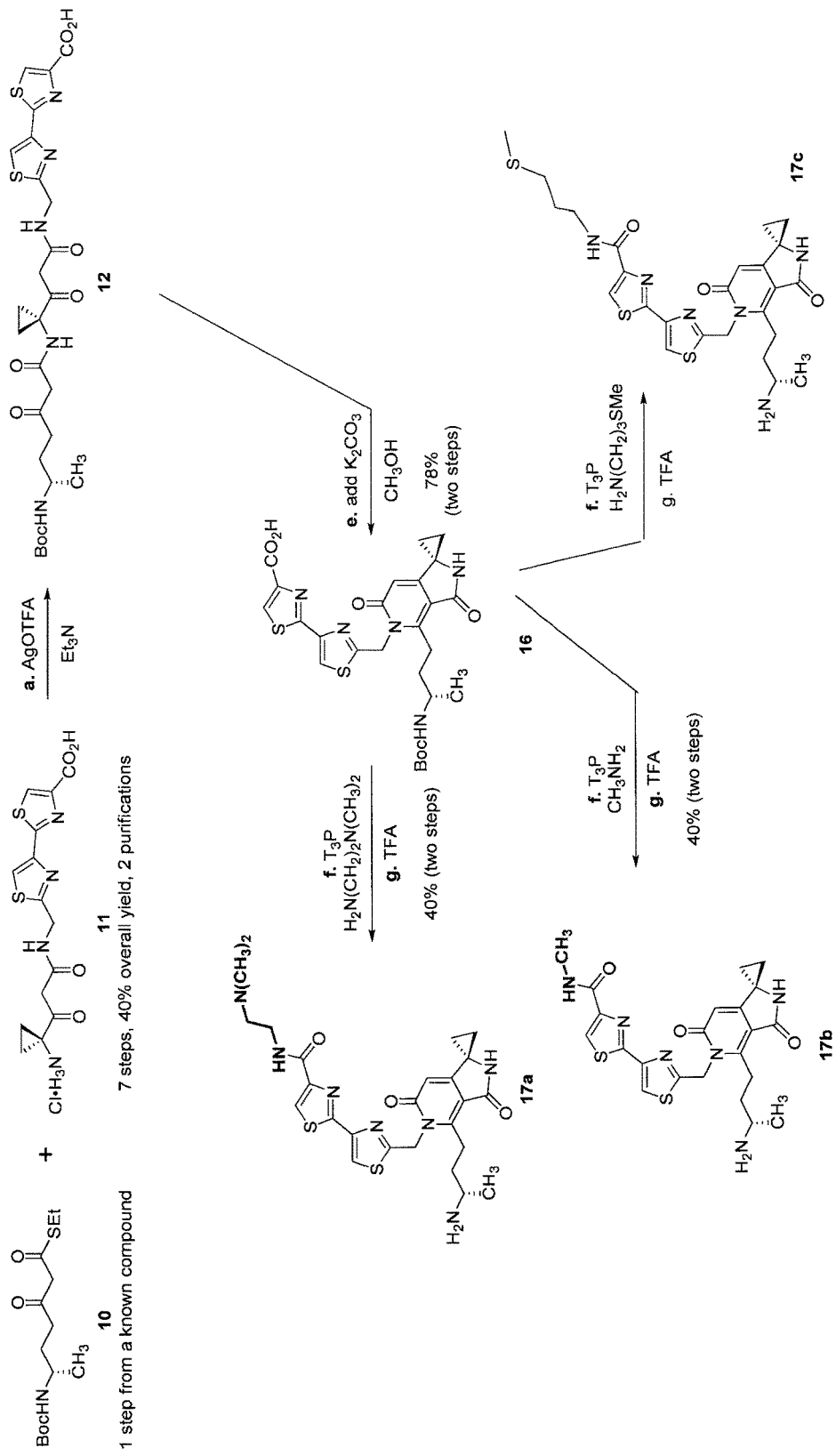
FIG. 1 shows scheme 1, which provides a chemical synthetic scheme to preferred compounds according to the present invention.
Figure 2:
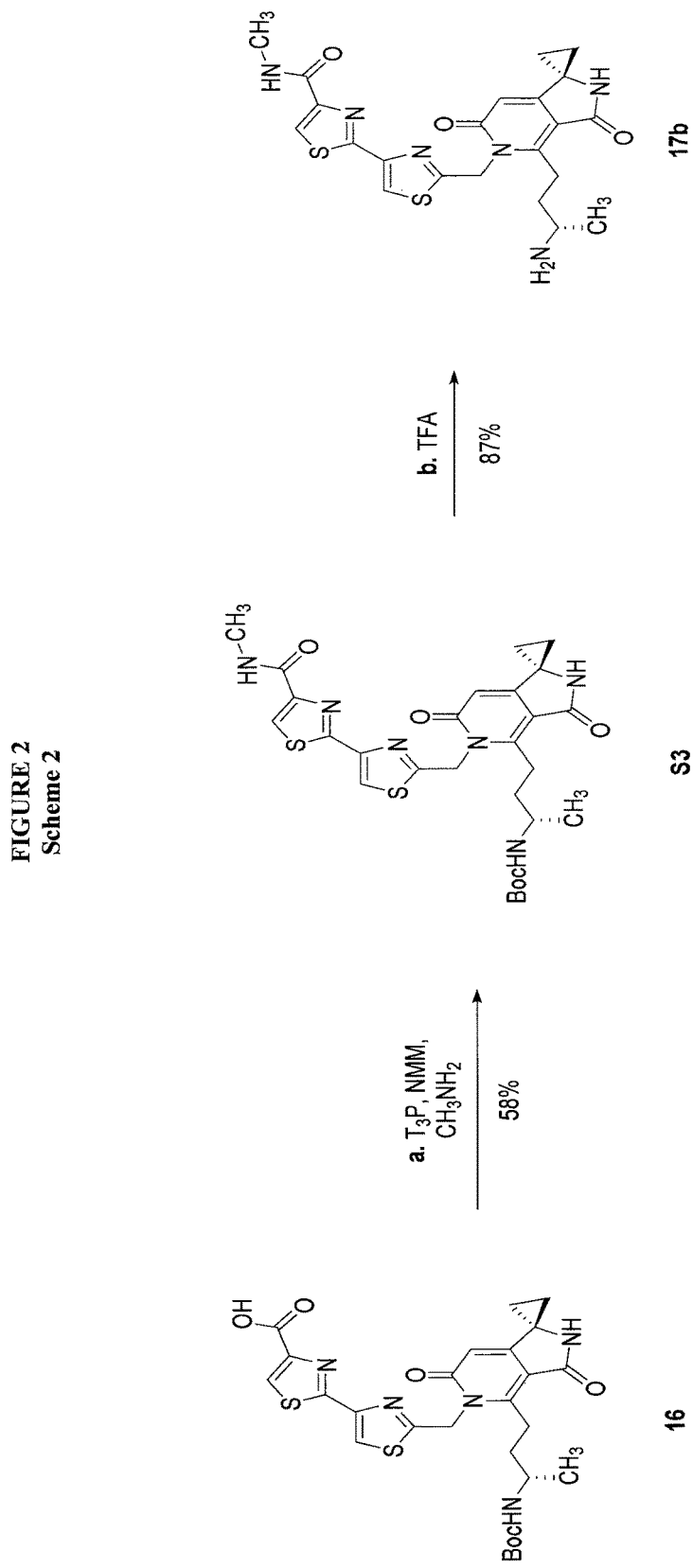
FIG. 2 shows scheme 2, which provides the steps for synthesizing amide compound 17b from the protected free carboxylic acid compound 16.

The following terms shall be used throughout the specification to describe the present invention. Where a term is not specifically defined herein, that term shall be understood to be used in a manner consistent with its use by those of ordinary skill in the art.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges that may independently be included in the smaller ranges are also encompassed within the invention, subject to any specifically excluded limit in the stated range. Where the stated range includes one or both of the limits, ranges excluding either both of those included limits are also included in the invention. In instances where a substituent is a possibility in one or more Markush groups, it is understood that only those substituents which form stable bonds are to be used.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a," "and" and "the" include plural references unless the context clearly dictates otherwise.

Furthermore, the following terms shall have the definitions set out below.

The term "patient" or "subject" is used throughout the specification within context to describe an animal, generally a mammal, especially including a domesticated animal and preferably a human, to whom treatment, including prophylactic treatment (prophylaxis), with the compounds or compositions according to the present invention is provided. For treatment of those infections, conditions or disease states which are specific for a specific animal such as a human patient, the term patient refers to that specific animal. In most instances, the patient or subject of the present invention is a human patient of either or both genders.

The term "effective" is used herein, unless otherwise indicated, to describe an amount of a compound or component which, when used within the context of its use, produces or effects an intended result, whether that result relates to the prophylaxis and/or therapy of an infection and/or disease state within the context of its use or as otherwise described herein. The term effective subsumes all other effective amount or effective concentration terms (including the term "therapeutically effective") which are otherwise described or used in the present application.

The term "compound" is used herein to describe any specific compound or bioactive agent disclosed herein, including any and all stereoisomers (including diastereomers, individual optical isomers/enantiomers or racemic mixtures and geometric isomers), pharmaceutically acceptable salts and prodrug forms. The term compound herein refers to stable compounds. Within its use in context, the term compound may refer to a single compound or a mixture of compounds as otherwise described herein. It is understood that the choice of substituents or bonds within a Markush or other group of substituents or bonds is provided to form a stable compound from those choices within that Markush or other group.

The term "pharmaceutically acceptable" as used herein means that the compound or composition is suitable for administration to a subject to achieve the treatments described herein, without unduly deleterious side effects in light of the severity of the disease and necessity of the treatment.

"Hydrocarbon" or "hydrocarbyl" refers to any monovalent (or divalent in the case of alkylene groups) radical containing carbon and hydrogen, which may be straight, branch-chained or cyclic in nature. Hydrocarbons include linear, branched and cyclic hydrocarbons, including alkyl groups, alkylene groups, saturated and unsaturated hydrocarbon groups including aromatic groups both substituted and unsubstituted, alkene groups (containing double bonds between two carbon atoms) and alkyne groups (containing triple bonds between two carbon atoms). In certain instances, the terms substituted alkyl and alkylene are sometimes used synonymously.

"Alkyl" refers to a fully saturated monovalent radical containing carbon and hydrogen, and which may be cyclic, branched or a straight chain. Examples of alkyl groups are methyl, ethyl, n-butyl, n-hexyl, n-heptyl, n-octyl, n-nonyl, n-decyl, isopropyl, 2-methyl-propyl, cyclopropyl, cyclopropylmethyl, cyclobutyl, cyclopentyl, cyclopentylethyl, cyclohexylethyl and cyclohexyl. Preferred alkyl groups are $C_1$-$C_6$ alkyl groups. "Alkylene" refers to a fully saturated hydrocarbon which is divalent (may be linear, branched or cyclic) and which is optionally substituted. Preferred alkylene groups are $C_1$-$C_6$ alkylene groups. Other terms used to indicate substitutent groups in compounds according to the present invention are as conventionally used in the art.

The term "aryl" or "aromatic", in context, refers to a substituted or unsubstituted monovalent aromatic radical having a single ring (e.g., benzene or phenyl). Other examples of aryl groups, in context, may include heterocyclic aromatic ring systems "heteroaryl" groups having one or more nitrogen, oxygen, or sulfur atoms in the ring (5- or 6-membered heterocyclic rings) such as imidazole, furyl, pyrrole, pyridyl, furanyl, thiene, thiazole, pyridine, pyrimidine, pyrazine, triazole, oxazole, among others, which may be substituted or unsubstituted as otherwise described herein.

The term "substituted" shall mean substituted at a carbon or nitrogen position within a molecule or moiety within context, a hydroxyl, carboxyl, cyano (C≡N), nitro ($NO_2$), halogen (preferably, 1, 2 or 3 halogens, especially on an alkyl, especially a methyl group such as a trifluoromethyl), alkyl group (preferably, $C_1$-$C_{12}$, more preferably, $C_1$-$C_6$), alkoxy group (preferably, $C_1$-$C_6$ alkyl or aryl, including phenyl and substituted phenyl), a $C_1$-$C_6$ thioether, ester (both oxycarbonyl esters and carboxy ester, preferably, $C_1$-$C_6$ alkyl or aryl esters) including alkylene ester (such that attachment is on the alkylene group, rather than at the ester function which is preferably substituted with a $C_1$-$C_6$ alkyl or aryl group), thioester (preferably, $C_1$-$C_6$ alkyl or aryl), halogen (preferably, F or Cl), nitro or amine (including a five- or six-membered cyclic alkylene amine, further including a $C_1$-$C_6$ alkyl amine or $C_1$-$C_6$ dialkyl amine which alkyl groups may be substituted with one or two hydroxyl groups), amido, which is preferably substituted with one or two $C_1$-$C_6$ alkyl groups (including a carboxamide which is substituted with one or two $C_1$-$C_6$ alkyl groups), alkanol (preferably, $C_1$-$C_6$ alkyl or aryl), or alkanoic acid (preferably, $C_1$-$C_6$ alkyl or aryl) or a thiol (preferably, $C_1$-$C_6$ alkyl or aryl), or thioalkanoic acid (preferably, $C_1$-$C_6$ alkyl or aryl). Preferably, the term "substituted" shall mean within its context of use alkyl, alkoxy, halogen, ester, keto, nitro, cyano and amine (especially including mono- or di-$C_1$-$C_6$ alkyl substituted amines which may be optionally substituted with one or two hydroxyl groups). Any substitutable position in a compound according to the present invention may be substituted in the present invention, but often no more than 3, more preferably no more than 2 substituents (in some instances only 1 or no substituents) is present on a ring. Preferably, the term "unsubstituted" shall mean substituted with one or more H atoms.

The term "tumor" is used to describe a malignant or benign growth or tumefacent.

The term "neoplasia" refers to the uncontrolled and progressive multiplication of tumor cells, under conditions that would not elicit, or would cause cessation of, multiplication of normal cells. Neoplasia results in a "neoplasm", which is defined herein to mean any new and abnormal growth, particularly a new growth of tissue, in which the growth of cells is uncontrolled and progressive. Thus, neoplasia includes "cancer", which herein refers to a proliferation of tumor cells having the unique trait of loss of normal controls, resulting in unregulated growth, lack of differentiation, local tissue invasion, and/or metastasis. The cancer may be "naïve", metastatic or recurrent and includes drug resistant and multiple drug resistant cancers, all of which may be treated using compounds according to the present invention.

As used herein, neoplasms include, without limitation, morphological irregularities in cells in tissue of a subject or host, as well as pathologic proliferation of cells in tissue of a subject, as compared with normal proliferation in the same type of tissue. Additionally, neoplasms include benign tumors and malignant tumors (e.g., colon tumors) that are either invasive or noninvasive. Malignant neoplasms are distinguished from benign neoplasms in that the former show a greater degree of anaplasia, or loss of differentiation and orientation of cells, and have the properties of invasion and metastasis. Examples of neoplasms or neoplasias from which the target cell of the present invention may be derived include, without limitation, carcinomas (e.g., squamous-cell carcinomas, adenocarcinomas, hepatocellular carcinomas, and renal cell carcinomas), particularly those of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, particularly Ewing's sarcoma, hemangiosarcoma, Kaposi's sarcoma, liposarcoma, myosarcomas, peripheral neuroepithelioma, and synovial sarcoma; tumors of the central nervous system (e.g., gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas); germ-line tumors (e.g., bowel cancer, breast cancer, prostate cancer, cervical cancer, uterine/endometrial cancer, lung cancer, ovarian cancer, testicular cancer, thyroid cancer, astrocytoma, esophageal cancer, pancreatic cancer, stomach cancer, liver cancer, colon cancer, and melanoma); mixed types of neoplasias, particularly carcinosarcoma and Hodgkin's disease; and tumors of mixed origin, such as WACMs' tumor and teratocarcinomas, which may be treated by one or more compounds according to the present invention. See, (Beers and Berkow (eds.), The Merck Manual of Diagnosis and Therapy, 17.sup.th ed. (Whitehouse Station, N.J.: Merck Research Laboratories, 1999) 973-74, 976, 986, 988, 991.

In certain particular aspects of the present invention, the cancer which is treated is metastatic cancer. Metastatic cancer may be found in virtually all tissues of a cancer patient in late stages of the disease, including the lymph system/nodes (lymphoma), in bones, in bladder tissue, in kidney tissue, liver tissue and in virtually any tissue, including brain (brain cancer/tumor). Thus, the present invention is generally applicable and may be used to treat any cancer in any tissue, regardless of etiology. In other instances, the cancer which is treated, including prophylactically treated, is a recurrent cancer, which often recurs after an initial remission. The present invention also may be used to reduce the likelihood of a cancer recurring and for treating a cancer which has recurred. In further instances the present compounds may be used to treat cancer stem cells, which often occur in metastatic and recurrent cancers.

The term "targeting element", "cancer cell targeting element", "$T_E$", "$CCT_E$" or "cell targeting element" is used to describe that portion of a compound according to the present invention which comprises at least one moiety which is capable of selectively binding to a cancer cell (these compounds are alternative described as chimeric compounds because of the dual nature of the compound). Targeting groups for including in compounds according to the present invention include small molecules which bind to folate receptors (folate receptor binding moiety), antibody-type $CCT_E$s such as monoclonal antibodies (especially a humanized monoclonal antibody) such as herceptin or antibody fragments (FAB), including single chain variable fragment (scFv) antibodies which bind to cancer cells, a PSMA binding moiety or a YSA peptide (which binds to Ephrin A2 (EphA2), as otherwise described herein. The targeting element $T_E$ may also include a peptide (e.g. a low pH insertion peptide, among others), an antibody or antibody fragment, a group according to the chemical structure

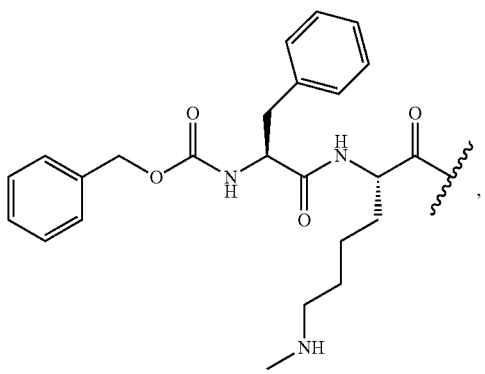 [SMILES: *C(=O)[C@H](CCCCNC)NC(=O)[C@H](Cc1ccccc1)NC(=O)OCc1ccccc1]

or a cysteine-cathepsin moiety.

The term "folate receptor binding moiety" (FRBM) or (FM) is used to describe a folate moiety which binds to cancer cells selectively and is used in the present invention to target folate receptors on cancer cells which are often overexpressed or hyperexpressed on cancer cells compared to normal cells. The folate receptor, given its selective heightened expression on cancer cells compared to normal cells represents an excellent selective target to bind compounds according to the present invention to cancer cells for uptake into cells where the intercalating moiety may exhibit its antiproliferative activity, resulting in cancer cell death. Folate receptor I is often overexpressed in numerous cancer cells including ovarian, breast, uterine, cervical, renal, lung, colorectal and brain cancer cells, thus making it an important targeting site for compounds according to the present invention.

Folate receptor binding moieties for use in the present invention include the following chemical structures:

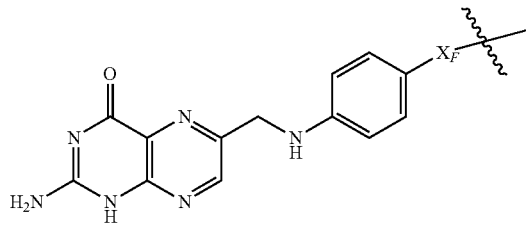

where $X_F$ is C(O), S(O), S(O)$_2$, CR$_F$R$_F$, O, S or N—R$_F$,
where R$_F$ is H or a C$_1$-C$_3$ alkyl (preferably H).

The term "prostate specific membrane antigen" or "PSMA" according to the chemical structure is directed to a cancer cell targeting moiety that binds to prostate specific membrane antigen (PSMA) which is frequently overexpressed or hyperexpressed in cancer cells. PSMA, although found on prostate cancer cells, including metastatic prostate cancer cells, are also found on virtually all other cancer cells and may be used to selectively target compounds according to the present invention to cancer cells. A number of metastatic and recurrent cancers also hyperexpress PSMA compared to naïve cancers and PSMA may represent a particularly useful binding site for metastatic and/or recurrent cancers.

PSMA binding moieties include moieties according to the chemical structure:

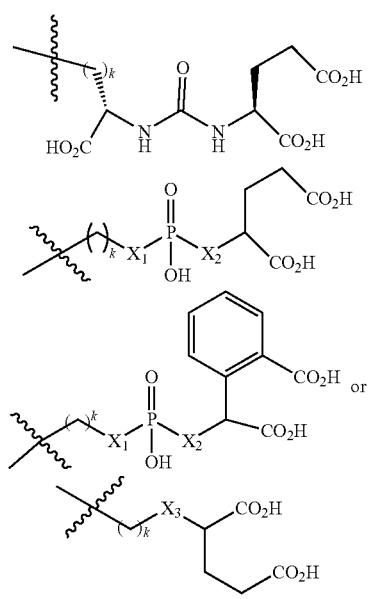

Where $X_1$ and $X_2$ are each independently CH$_2$, O, NH or S;
$X_3$ is O, CH$_2$, NR$^1$, S(O), S(O)$_2$, —S(O)$_2$O, —OS(O)$_2$, or OS(O)$_2$O;
R$^1$ is H, a C$_1$-C$_3$ alkyl group, or a —C(O)(C$_1$-C$_3$) group;
k is an integer from 0 to 20, 8 to 12, 1 to 15, 1 to 10, 1 to 8, 1 to 6, 1, 2, 3, 4, 5 or 6;
or a salt or enantiomer thereof.

A preferred PSMA binding group (CCT$_E$) for use in the present invention is the group

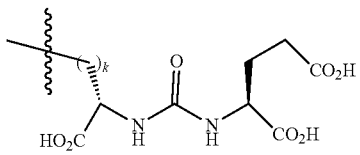

Where k is 2, 3 or 4, preferably 3 or 4. This CCT$_E$ group, as well as the others, optionally has an amine group or other functional group at the distill end of the alkylene group (k) such that k is formed from, for example, a lysine amino acid, such that the amine group or other functional group may participate in further reactions to form a linker, a connector group [CON], a multifunctional group [MULTICON] or may be linked directly to an (ACM) as otherwise described herein.

The term "antibody", also referred to an immunoglobulin (Ig), is a protein, which is Y-shaped and produced by B-cells that the immune system uses to identify and neutralize foreign objects in the body, such as pathogens, including viruses, bacteria and cancer cells, which the immune system recognizes as objects to the immune system. As used herein, antibody includes, but is not limited to, monoclonal antibodies. The following disclosure from U.S. Patent Application Document No. 20100284921, the entire contents of which are hereby incorporated by reference, exemplifies techniques that are useful in making antibodies which may be modified and employed in chimeric compounds of the instant invention.

Pursuant to its use in the present invention, the antibody is preferably a chimeric antibody. For human use, the antibody is preferably a humanized chimeric antibody. [A]n anti-target-structure antibody . . . may be monovalent, divalent or polyvalent in order to achieve target structure binding. Monovalent immunoglobulins are dimers (HL) formed of a hybrid heavy chain associated through disulfide bridges with a hybrid light chain. Divalent immunoglobulins are tetramers (H2L2) formed of two dimers associated through at least one disulfide bridge.

As discussed above, the term antibody for use in the present invention includes compounds which exhibit binding characteristics comparable to those of the antibodies, and include, for example, hybridized and single chain antibodies, as well as fragments thereof. Methods of producing such compounds are disclosed in PCT Application Nos. WO 1993/21319 and WO 1989/09622. These compounds include polypeptides with amino acid sequences substantially the same as the amino acid sequence of the variable or hypervariable regions of the antibodies raised against targets on cancer cells pursuant to the practice of the present invention. These may be readily modified to link these CCT$_E$s to the (ACM), thus forming chimeric compounds hereunder.

Compounds according to the present invention which serve to bind to target cancer cells include fragments of antibodies (FAB) that have the same, or substantially the same, binding characteristics to those of the whole antibody. Such fragments may contain one or both Fab fragments or the F(ab')$_2$ fragment. Preferably the antibody fragments contain all six complement determining regions of the whole antibody, although fragments containing fewer than all of such regions, such as three, four or five complement determining regions, are also functional. The functional equivalents are members of the IgG immunoglobulin class and subclasses thereof, but may be or may combine any one of the following immunoglobulin classes: IgM, IgA, IgD, or IgE, and subclasses thereof. Heavy chains of various subclasses, such as the IgG subclasses, are responsible for different effector functions and thus, by choosing the desired heavy chain constant region, hybrid antibodies with desired effector function are produced. Preferred constant regions are gamma 1 (IgG1), gamma 2 (IgG2 and IgG), gamma 3 (IgG3) and gamma 4 (IgG4). The light chain constant region can be of the kappa or lambda type.

In another approach, the monoclonal antibodies may be advantageously cleaved by proteolytic enzymes to generate fragments retaining the target structure binding site. For example, proteolytic treatment of IgG antibodies with papain at neutral pH generates two identical so-called "Fab" fragments, each containing one intact light chain disulfide-bonded to a fragment of the heavy chain (Fc). Each Fab fragment contains one antigen-combining site. The remaining portion of the IgG molecule is a dimer known as "Fc". Similarly, pepsin cleavage at pH 4 results in the so-called F(ab')2 fragment.

Single chain antibodies or Fv fragments are polypeptides that consist of the variable region of the heavy chain of the antibody linked to the variable region of the light chain, with or without an interconnecting linker. Thus, the Fv comprises an antibody combining site. Hybrid antibodies also may be employed as CCT$_E$s in the chimeric compounds according to the present invention. Hybrid antibodies have constant regions derived substantially or exclusively from human antibody constant regions and variable regions derived substantially or exclusively from the sequence of the variable region of a monoclonal antibody from each stable hybridoma.

Methods for preparation of fragments of antibodies (e.g. for preparing an antibody or an antigen binding fragment thereof having specific binding affinity for a cancer cell target are readily known to those skilled in the art. See, for example, Goding, "Monoclonal Antibodies Principles and Practice", Academic Press (1983), p. 119-123. Fragments of the monoclonal antibodies containing the antigen binding site, such as Fab and F(ab')2 fragments, may be preferred in therapeutic applications, owing to their reduced immunogenicity. Such fragments are less immunogenic than the intact antibody, which contains the immunogenic Fc portion. Hence, as used herein, the term "antibody" includes intact antibody molecules and fragments thereof that retain antigen binding ability.

When the antibody used in the methods used in the practice of the invention is a monoclonal antibody, the antibody is generated using any known monoclonal antibody preparation procedures such as those described, for example, in Harlow et al. (supra) and in Tuszynski et al. (Blood 1988, 72:109-115). Generally, monoclonal antibodies directed against a desired antigen are generated from mice immunized with the antigen using standard procedures as referenced herein. Monoclonal antibodies directed against full length or fragments of target structure may be prepared using the techniques described in Harlow et al. (supra).

Chimeric animal-human monoclonal antibodies may be prepared by conventional recombinant DNA and gene transfection techniques well known in the art. The variable region genes of a mouse antibody-producing myeloma cell line of known antigen-binding specificity are joined with human immunoglobulin constant region genes. When such gene constructs are transfected into mouse myeloma cells, the antibodies produced are largely human but contain antigen-binding specificities generated in mice. As demonstrated by Morrison et al., 1984, Proc. Natl. Acad. Sci. USA 81:6851-6855, both chimeric heavy chain V region exon (VH)-human heavy chain C region genes and chimeric mouse light chain V region exon (VK)-human K light chain gene constructs may be expressed when transfected into mouse myeloma cell lines. When both chimeric heavy and light chain genes are transfected into the same myeloma cell, an intact H2L2 chimeric antibody is produced. The methodology for producing such chimeric antibodies by combining genomic clones of V and C region genes is described in the above-mentioned paper of Morrison et al., and by Boulianne et al. (Nature 1984, 312:642-646). Also see Tan et al. (J. Immunol. 1985, 135:3564-3567) for a description of high level expression from a human heavy chain promoter of a human-mouse chimeric K chain after transfection of mouse myeloma cells. As an alternative to combining genomic DNA, cDNA clones of the relevant V and C regions may be combined for production of chimeric antibodies, as described by Whitte et al. (Protein Eng. 1987, 1:499-505) and Liu et al. (Proc. Natl. Acad. Sci. USA 1987, 84:3439-3443). For examples of the preparation of chimeric antibodies, see the following U.S. Pat. Nos. 5,292,867; 5,091,313; 5,204,244; 5,202,238; and 5,169,939. The entire disclosures of these patents, and the publications mentioned in the preceding paragraph, are incorporated herein by reference. Any of these recombinant techniques are available for production of rodent/human chimeric monoclonal antibodies against target structures.

When antibodies other than human antibodies are modified for incorporation into chimeric compounds pursuant to the present invention, it may be necessary to reduce the immunogenicity of the murine antibody. To further reduce the immunogenicity of murine antibodies, "humanized" antibodies have been constructed in which only the minimum necessary parts of the mouse antibody, the complementarity-determining regions (CDRs), are combined with human V region frameworks and human C regions (Jones et al., 1986, Nature 321:522-525; Verhoeyen et al., 1988, Science 239:1534-1536; Hale et al., 1988, Lancet 2:1394-1399; Queen et al., 1989, Proc. Natl. Acad. Sci. USA 86:10029-10033). The entire disclosures of the aforementioned papers are incorporated herein by reference. This technique results in the reduction of the xenogeneic elements in the humanized antibody to a minimum. Rodent antigen binding sites are built directly into human antibodies by transplanting only the antigen binding site, rather than the entire variable domain, from a rodent antibody. This technique is available for production of chimeric rodent/human anti-target structure antibodies of reduced human immunogenicity."

The term antibody fragment or "FAB" is used to describe a fragment of an antibody which substantially maintains the same binding characteristics of the whole antibody, but eliminates other chemical features of the antibody which may complicate administration and produce untoward immunogenic responses in a patient.

The term "single-chain antibody variable fragment") or "scFv" is used to describe an artificial construct that links the sequences encoding the $V_H$ and $V_L$ domains of an antibody into a single polypeptide chain and lacks the rest of the antibody molecule. Because the antigen-binding site of an antibody is formed in a cavity at the interface between $V_H$ and $V_L$ domains, the scFv preserves the antigen binding activity of the intact antibody molecule. Normally the $V_H$ and $V_L$ domains are parts of different polypeptide chains (the heavy and light chains, respectively), but in the scFv they are joined into a single polypeptide that can be fused genetically to other proteins, for example, proteins on cancer cells to be targeted. These scFvs may form the basis of effective CCTEs on chimeric compounds according to the present invention.

The term "protecting group", "PG" or "blocking group" refers to a group which is introduced into a molecule by chemical modification of a function group to obtain chemoselectivity in a subsequent chemical reaction. It plays an important role in providing precursors to chemical components which provide compounds according to the present invention. Blocking groups may be used to protect functional groups on ACM groups, $CCT_E$ groups, connector molecules and/or linker molecules in order to assemble compounds according to the present invention. Typical blocking groups are used on alcohol groups, amine groups, carbonyl groups, carboxylic acid groups, phosphate groups and alkyne groups among others.

Exemplary alcohol/hydroxyl protecting groups include acetyl (removed by acid or base), benzoyl (removed by acid or base), benzyl (removed by hydrogenolysis, β-methoxyethoxymethyl ether (MEM, removed by acid), dimethoxytrityl [bis-(4-methoxyphenyl)phenylmethyl] (DMT, removed by weak acid), methoxymethyl ether (MOM, removed by acid), methoxytrityl [(4-methoxyphenyl)diphenylmethyl], (MMT, Removed by acid and hydrogenolysis), p-methoxylbenzyl ether (PMB, removed by acid, hydrogenolysis, or oxidation), methylthiomethyl ether (removed by acid), pivaloyl (Piv, removed by acid, base or reductant agents. More stable than other acyl protecting groups, tetrahydropyranyl (THP, removed by acid), tetrahydrofuran (THF, removed by acid), trityl (triphenyl methyl, (Tr, removed by acid), silyl ether (e.g. trimethylsilyl or TMS, tert-butyldimethylsilyl or TBDMS, tri-iso-propylsilyloxymethyl or TOM, and triisopropylsilyl or TIPS, all removed by acid or fluoride ion such as such as NaF, TBAF (tetra-n-butylammonium fluoride, HF-Py, or HF-NEt$_3$); methyl ethers (removed by TMSI in DCM, MeCN or chloroform or by BBr$_3$ in DCM) or ethoxyethlyl ethers (removed by strong acid).

Exemplary amine-protecting groups include carbobenzyloxy (Cbz group, removed by hydrogenolysis), p-Methoxylbenzyl carbon (Moz or MeOZ group, removed by hydrogenolysis), tert-butyloxycarbonyl (BOC group, removed by concentrated strong acid or by heating at elevated temperatures), 9-Fluorenylmethyloxycarbonyl (FMOC group, removed by weak base, such as piperidine or pyridine), acyl group (acetyl, benzoyl, pivaloyl, by treatment with base), benzyl (Bn groups, removed by hydrogenolysis), carbamate, removed by acid and mild heating, p-methoxybenzyl (PMB, removed by hydrogenolysis), 3,4-dimethoxybenzyl (DMPM, removed by hydrogenolysis), p-methoxyphenyl (PMP group, removed by ammonium cerium IV nitrate or CAN); tosyl (Ts group removed by concentrated acid and reducing agents, other sulfonamides, Mesyl, Nosyl & Nps groups, removed by samarium iodide, tributyl tin hydride.

Exemplary carbonyl protecting groups include acyclical and cyclical acetals and ketals (removed by acid), acylals (removed by Lewis acids) and dithianes (removed by metal salts or oxidizing agents).

Exemplary carboxylic acid protecting groups include methyl esters (removed by acid or base), benzyl esters (removed by hydrogenolysis), tert-butyl esters (removed by acid, base and reductants), esters of 2,6-disubstituted phenols (e.g. 2,6-dimethylphenol, 2,6-diisopropylphenol, 2,6-di-tert-butylphenol, removed at room temperature by DBU-catalyzed methanolysis under high-pressure conditions, silyl esters (removed by acid, base and organometallic reagents), orthoesters (removed by mild aqueous acid), oxazoline (removed by strong hot acid (pH<1, T>100° C.) or strong hot alkali (pH>12, T>100° C.)).

Exemplary phosphate group protecting groups including cyanoethyl (removed by weak base) and methyl (removed by strong nucleophiles, e.g. thiophenol/TEA).

Exemplary terminal alkyne protecting groups include propargyl alcohols and silyl groups.

The term "linker" (designated as "L", "(L)", "$L_C$" or ($L_C$)" in compounds according to the present invention) is used to describe a chemical moiety which, when present in chimeric molecules according to the present invention, covalently binds a (ACM) group to a ($CCT_E$) group, optionally through one or more [CON] groups and/or one or more alternative linker groups. The linker group may be cleavable or noncleavable depending on the function of the $CCT_E$ group or the compound itself (in the case of dimeric compounds according to the present invention). In general, antibody or antibody related ($CCT_E$) groups described above are generally, but not exclusively linked to a (ACM) group through a cleavable linker group. Other $CCT_E$s often are linked to (ACM) groups through a non-cleavable linker group.

Typical cleavable linker groups (L), which may be represented as ($L_{CL}$), for use in the present invention are represented by any chemical structure which is compatible with the chemistry of the chimeric compounds and their administration to a patient and readily cleave in or on a cell in which the chimeric molecule is introduced. In general, the cleavable linker for use in compounds according to the present invention is at least one chemical moiety, more often at least two chemical moieties in length to upwards of 100 or more moieties in length. These linkers are presented in detail hereinbelow. Often, one or more linkers, especially cleavable linker groups may be linked to one or more non-cleavable (non-labile) linker groups either directly or through a connector group (CON) or multiconnector group (MULTICON) as otherwise described herein. These form a more complex linker group.

Cleavable or labile linkers ($L_{CL}$) allow the [ACM] moiety to be cleaved from the (CCTM) in compounds according to the present invention order to provide a maximal effect in the cell, by allowing the ACM to be cleaved from the CCTM after the compound targets the cancer cell, facilitating entry of the ACM into the cell which causes cleavage/breakage and/or intercalation of the cell's DNA, causing cytotoxicity and cell death. These labile linkers include hydrolytically labile (acid labile) linkers, reductively labile linkers (principally disulfide linkers which are reductively cleaved by intracellular glutathione or other disulfide reducing agent) and enzymatically labile linkers (protease substrates).

In certain embodiments according to the present invention, the cleavable linker $L_{CL}$ is a disulfide wherein one of the sulfurs in the disulfide group is provided by a cysteinyl residue alone or as an oligopeptide ranging from about 1 to about 10 amino acid units in length, often 1, 2 or 3 amino acid units in length. In certain embodiments the oligopeptide is represented by a glutamyl cysteinyl dipeptide (with the amide formed between the sidechain carboxylic acid of the glutamic acid and the amine of the cysteinyl residue), a glycinyl cysteinyl dipeptide, an alaninyl cysteinyl dipeptide or a lysinyl cystinyl dipeptide. The dipeptide may be linked (mated) with another dipeptide of similar or different structure each having a cysteinyl residue linked to the cysteinyl residue of the other dipeptide, or the dipeptide may be linked with a mercaptide such as an alkyl mercaptide (which is further substituted with a group which can further link the cleavable linker to another group, such as a non-cleavable (non-labile) linker an (ACM) group or a ($CCT_E$) group or a connector group, etc.

In other embodiments the cleavable linker group ($L_{CL}$) is an oligopeptide (containing a disulfide group as described above) or other linker which contains an ester group which may readily cleaved. For example, a linker may consist of a dipeptide such as a glutamyl cysteinyl group which provides a disulfide link to a linker (such as a alkylene group or polyethylene glycol group) which can form an integral connector molecule (such as a difunctional triazole CON group or a MULTICON group) as otherwise described herein, or alternatively bind directly to an ACM group or a CCTM group.

Cleavable or labile linkers ($L_C$) may comprise a group represented by the chemical structures:

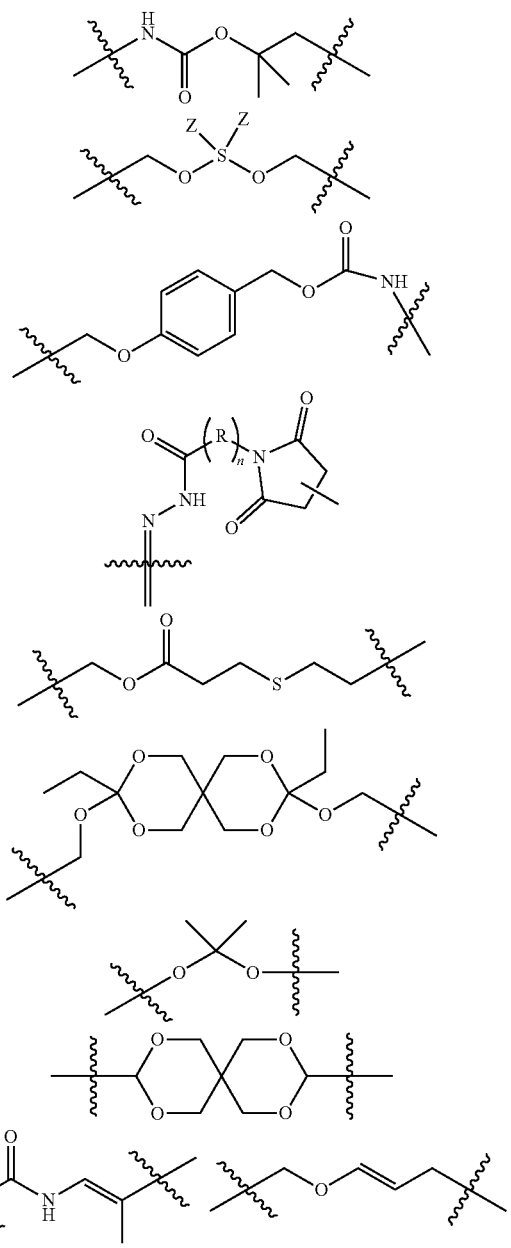

-continued

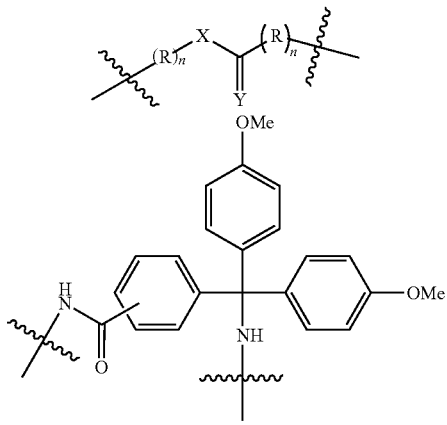

where R is an ethylene glycol group, a methylene group or an amino acid, preferably an ethylene glycol group or an amino acid and n in this labile linker is from 0 to 10, often from 1 to 6, or 1 to 3 and where points of attachment (as indicated) are to other portions of the cleavable or labile linker ($L_C$), a difunctional connector moiety (CON), a non-cleavable (non-labile) linker ($L_N$), or a multifunctional connector molecule [MULTICON], through which an [ACM] functional group and a [CCTM] functional group are linked as otherwise described herein;

X is O, N—$R^{AL}$ or S;

$R^{AL}$ is H or a $C_1$-$C_3$ alkyl group (often H or Me, most often H);

Y is O or S and

Z=Me, Et, iPr, tBu, Ph, each of which may be optionally substituted with one or more halogen groups (especially from three up to five Fs, preferably no more than three Fs) and where said Ph group may be further optionally substituted with a $C_1$-$C_3$ alkyl group (which itself may be substituted with up to three halogens, preferably F) or OMe.

Exemplary reductively cleaved moieties (by glutathione, other reductive species within the cell) include moieties according to the chemical formula:

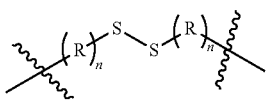

Where R is independently an ethylene glycol group, a methylene group or an amino acid where at least one amino acid (that which provides one of the sulfurs in the disulfide group) is a cysteinyl group (often, (R)n is a glutamyl cysteinyl or lysinyl cysteinyl dipeptide) and n in this labile linker is from 0 to 10, often from 1 to 6, or 1, 2 or 3 and where points of attachment (as indicated) are to other portions of the cleavable/labile linker [$L_{CL}$], a difunctional connector molecule or group (CON), a non-labile linker (NLL) or a multifunctional connector group molecule [MULTICON] as otherwise described herein.

Another reductively cleaved linker ($L_{CL}$) which is often used in compounds according to the present invention is represented by the following structure:

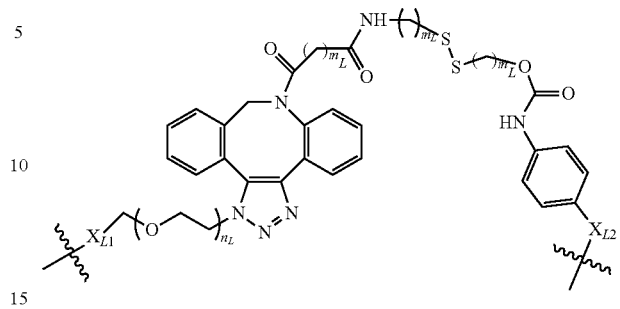

Where $X_{L1}$ is —$(CH_2)_{mL}$(C=O)—, —$(CH_2)_{mL''}$, $NR_{1L}$, $NR_{1L}$(C=O), S, S=O or S(O)$_2$, or a nucleophilic or electrophilic functional group (which can be further reacted to form a covalent link);

$X_{L2}$ is —$(CH_2)_{mL}$(C=O)—, —$(CH_2)_{mL''}$, —$(CH_2)_{mL}$ $NR_{1L}$—$(CH_2)_{mL''}$, $NR_{1L}$(C=O), S, S=O or S(O)$_2$, or a nucleophilic or electrophilic functional group (which can be further reacted to form a covalent link);

$R_{1L}$ is H or a $C_1$-$C_3$ alkyl group;

Each $m_L$ is independently 1, 2, 3, or 4 (often, each $m_L$ is 2);

mL' is 0, 1, 2, 3, 4, or 5 (preferably 0);

mL" is 1, 2, 3, 4 or 5; and $n_L$ is 0-20, 1-15, 2-10, 1-6, 1, 2, 3, 4, 5, 6, 7, or 8.

In certain embodiments of the above compounds as described above, $X_{L1}$ and $X_{L2}$ are optionally functional groups on the linker moiety (pre-linker molecules), for example, nucleophilic and/or electrophilic groups which are reactive with a corresponding electrophilic and/or nucleophilic group on the ACM, $CCT_E$, [CON] group or another linker molecule so that the ACM group, $CCT_E$, [CON] group or another linker molecule can be covalent linked or coupled to the linker group. In certain embodiments, $X_{L1}$ and/or $X_{L2}$ groups are nucleophilic groups such as amine groups, hydroxyl groups, sulfhydryl groups or nucleophilic carbon groups (e.g., carbanions) which couple and form covalent bonds with a corresponding electrophilic group such as an ester groups (which may be activated), acyl groups (activated), or other electrophilic groups such as trichloromethylmethyliminoester (—O—C=NH(CCl$_3$)), among others, on the ACM, $CCT_E$, [CON] moiety or alternative linker molecule. Alternatively, $X_{L1}$ and/or $X_{L2}$ may be nucleophilic groups such as an amine group, a hydroxyl group or a sulfhydryl group which are reactive with a corresponding electrophilic groups as described above. In these pre-linker molecules, each of $X_{L1}$ and $X_{L2}$ may be a nucleophilic and an electrophilic group. This approach applies to all linkers provided herein which may be presented as prelinker compounds capable of coupling with functional groups on the ACM, $CCT_E$, [CON] or alternative linker components of the present compounds.

In certain embodiments, the reductively cleaved linker ($L_{CL}$) is a moiety according to the chemical structure:

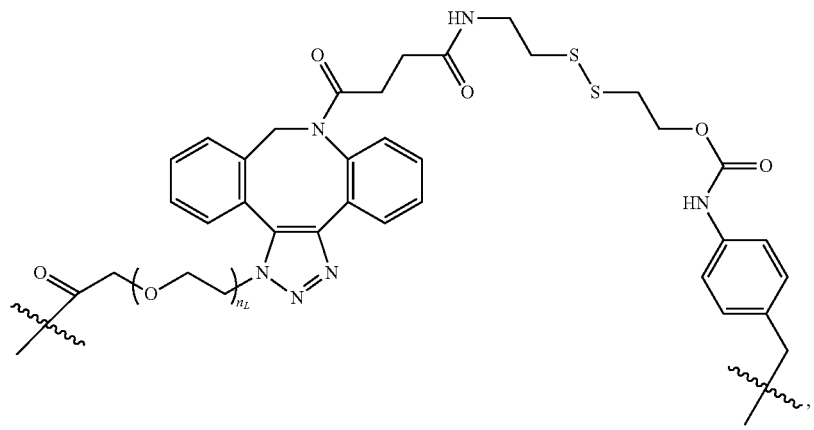

Where $n_L$ is 0-20, 1-15, 2-10, 1-6, 1, 2, 3, 4, 5, 6, 7, or 8.

In certain alternative embodiments, a partial cleavage linker containing an alkynyl containing functional group (which ultimately forms a connector group) is according to the chemical structure:

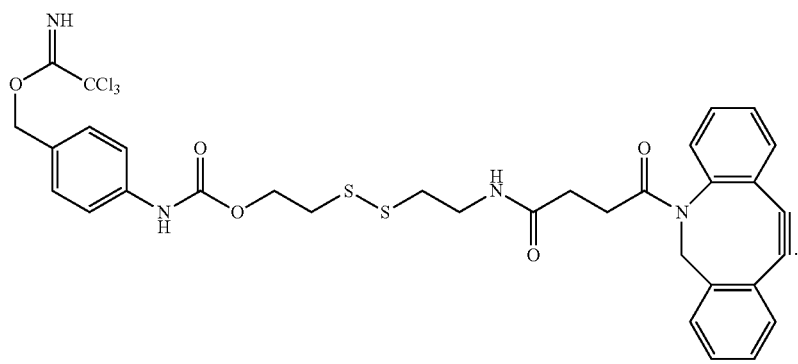

This linker may be reacted with other components (which may include $CCT_E$ groups, ACM groups, [CON] groups or alternative linkers containing a hydroxyl group to react with the trichloromethylmethyliminoester (—O—C=NH(CCl$_3$)) functional group at one end of the molecule and an azide group at the alkynyl functionality according to the present invention to form exemplary compounds according to the present invention.

In alternative versions of this approach, the linker molecule is according to the chemical structure:

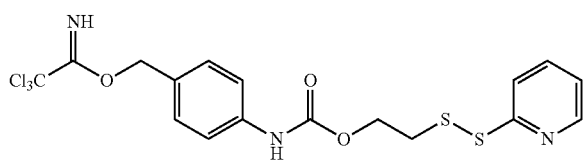

Where the trichloromethylmethyliminoester (—O—C=NH (CCl$_3$)) functional group may be used to covalently link a hydroxyl group to form an ether and the disulfide group is used to bind to a cysteinyl group of an antibody or other oligo- or polypeptide.

Exemplary enzymatically cleaved labile linkers include those according to the chemical structure:

Where the protease (cathepsin) substrate is a peptide containing from 2 to 50 amino acid units or more, often 2 to 25 amino acid units, 2 to 15 amino acid units, 2 to 10 amino acid units, 2 to 6 amino acids, 2 to 4 amino acids, 2, 3 or 4. Often, the protease substrate, above contains, comprises, consists essentially of or consists of the following peptides the point of attachment being at the distal ends of the peptide:
- -Gly-Phe-Leu-Gly-;
- -Ala-Leu-Ala-Leu;
- -Phe-Arg-;
- -Phe-Lys-;
- -Val-Cit- (valine-citrillune)
- -Val-Lys-
- -Val-Ala- and where R (above) is an ethylene glycol group, or a methylene group and n is from 0 to 10, often from 1 to 6, or 1 to 3 and where points of attachment (as indicated) are joined to other portions of the labile linker, a difunctional connector group or molecule (CON), a non-labile linker (NLL) or other moiety as described herein.

Other enzyme labile linkers are the beta-glucosidase labile linkers according to the chemical structure:

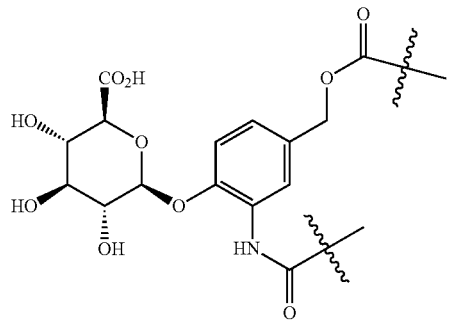 [SMILES: *C(=O)Nc1cc(COC(*)=O)ccc1O[C@@H]1O[C@H](C(=O)O)[C@@H](O)[C@H](O)[C@H]1O]

Where the points of attachment are joined to other portions of the labile linker, a difunctional connector moiety (CON), a non-labile linker (NLL) or a multifunctional connector group or molecule [MULTICON] as otherwise described herein.

In each of the above labile linkers, at the point of attachment in each group, the labile linker may be further linked to a non-labile linker as otherwise described herein, preferably a (poly)ethylene glycol group of from 1 to 12 glycol units (often 2 to 8 glycol units or 4 to 6 units) or an alkylene chain from 1 to 20 methylene units, often 1 to 10 methylene units, often 1 to 8 methylene units, more often 1 to 6 methylene unit, often 2 to 4 methylene units.

Preferred non-labile linkers include, for example, (poly) ethylene glycol linkers ranging in length from 2 to about 100 ethylene glycol units, preferably about 2 to 10 ethylene glycol units, about 2 to about 25, about 2 to about 15, about 2 to about 14, about 4 to about 10 units. In other preferred embodiments, the non-cleavable linker ($L_N$) is a polyethylene-co-polypropylene (PEG/PPG block copolymer) linker ranging from 2 to about 100, about 2 to about 25, about 2 to about 15, about 2 to about 14, about 2 to about 10, about 4 to about 10, combined ethylene glycol and propylene glycol units.

(Poly)alkylene chains as otherwise described herein are also preferred $L_N$ for use in the present invention. When present, these have 1 to about 100 units, often about 2 to 10 units, about 2 to about 25, about 2 to about 15, about 2 to about 14, about 4 to about 10 units. $L_N$ for use in the present invention may also contain one or more connector CON moieties as otherwise described herein which chemically connect separate (two or more) $L_N$ portions, the entire portion being labeled $L_N$. In addition, a non-cleavable linker $L_N$ may be linked through at least one connector moiety CON (as described in greater detail herein) to a cleavable linker $L_C$ in order to provide a linker moiety.

In certain preferred embodiments, the non-labile linker (NLL) is represented by the following exemplary structures (note that the NLL may contain one ore more CON moieties as discussed above):

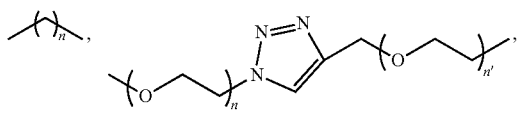

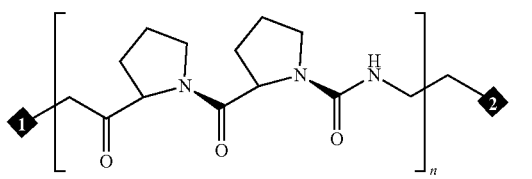

POLYPROLINE LINKER

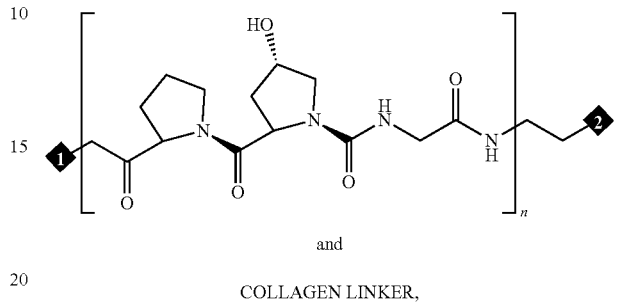

and

COLLAGEN LINKER, among numerous others, as described herein.

where n and n' are each independently 0 to 100, preferably 1 to 100, more preferably about 2 to about 20, about 2 to about 10, about 4 to about 10, about 4 to about 8.

The non-labile linker group NLL may also be a linker according to the chemical formula:

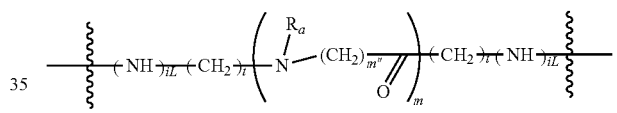

where $R_a$ is H or a $C_1$-$C_3$ alkyl, preferably $CH_3$, most often H;

m is an integer from 1 to 12, often 1, 2, 3, 4, 5, or 6;

m" is an integer 1, 2, 3, 4, 5, or 6, often 6;

t is 0, 1, 2, 3, 4, 5, or 6; and iL is 0 or 1, often 1; or a linker according to the structure:

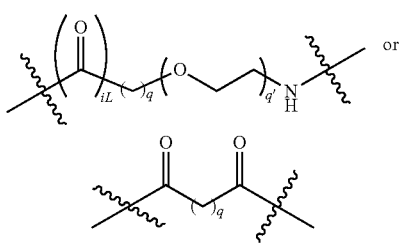

Where q is an integer from 0-12, preferably 1, 2, 3, 4, 5 or 6;

q' is 1 to 12, often 1, 2, 3, 4, 5 or 6 and iL is 0 or 1, preferably 1.

The two above linkers may be linked together to provide further linkers which are often used in compounds according to the present invention:

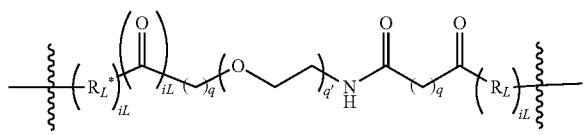

Where q is an integer from 0-12, preferably 0, 1, 2, 3, 4, 5 or 6;
q' is 1 to 12, often 1, 2, 3, 4, 5 or 6;
iL is 0 or 1; and
$R_L$ is an amino acid or an oligopeptide (which term includes a dipeptide) as otherwise described herein, especially including lysine, dilysine, or glycinelysine.

Another linker according to the present invention includes a linker based upon succinimide according to the chemical formula:

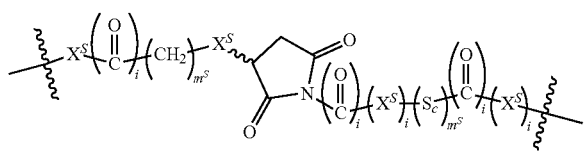

where each $X^S$ is independently a bond, S, O or N—$R^S$, preferably S;
$R^S$ is H or $C_{1-3}$ alkyl, preferably H;
$S_c$ is $CH_2$; $CH_2O$; or $CH_2CH_2O$;
i is 0 or 1; and
$m^S$ is 0, 1, 2, 3, 4, 5, 6, 7, 8, 9 or 10 (preferably 1-5).

In certain additional embodiments, the linker group is an amino acid, a dipeptide or an oligopeptide containing from 1 to 12, preferably 1 to 6 amino acid monomers or more. In certain embodiments, the oligopeptide is a dipeptide and the dipeptide is a dilysine or a glycinelysine dipeptide. When lysine is used as an amino acid in an oligopeptide linker, the sidechain alkylene amine may be used to link other linker groups or other components in the molecule. The dipeptide or oligopeptide may be considered a cleavable linker or non-cleavable depending upon the nature of the peptide.

In certain additional embodiments, as discussed above, the linker group NLL is a group

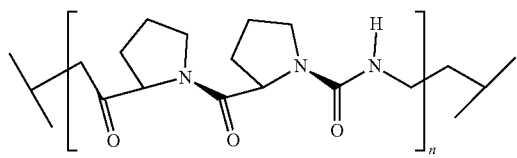

polyproline linker
or

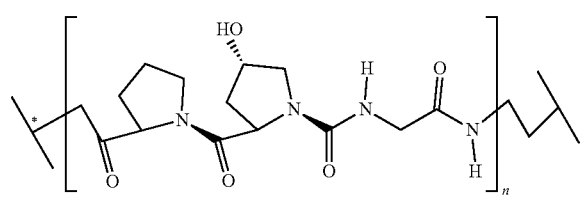

or collagen linker,
a group

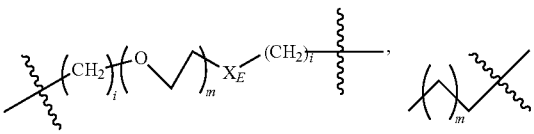

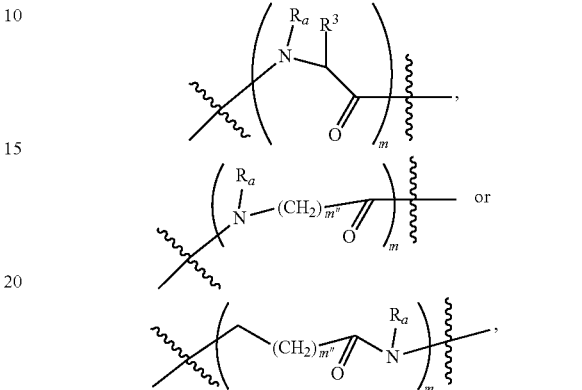

or a polypropylene glycol or polypropylene-co-polyethylene glycol linker having between 1 and 100 glycol units (1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 52 and 50, 3 and 45);
Where $R_a$ is H, $C_1$-$C_3$ alkyl or alkanol or forms a cyclic ring with $R^3$ (proline) and $R^3$ is a side chain derived of an amino acid preferably selected from the group consisting of alanine (methyl), arginine (propyleneguanidine), asparagine (methylenecarboxyamide), aspartic acid (ethanoic acid), cysteine (thiol, reduced or oxidized di-thiol), glutamine (ethylcarboxyamide), glutamic acid (propanoic acid), glycine (H), histidine (methyleneimidazole), isoleucine (1-methylpropane), leucine (2-methylpropane), lysine (butyleneamine), methionine (ethylmethylthioether), phenylalanine (benzyl), proline ($R^3$ forms a cyclic ring with $R_a$ and the adjacent nitrogen group to form a pyrrolidine group), serine (methanol), threonine (ethanol, 1-hydroxyethane), tryptophan (methyleneindole), tyrosine (methylene phenol) or valine (isopropyl);
$X_E$ is a bond, O, N—$R_{NA}$, or S;
$R_{NA}$ is H or $C_1$-$C_3$ alkyl, preferably H;
i is an integer from 0 to 6 (0, 1, 2, 3, 4, 5, or 6);
m" is an integer from 0 to 25, preferably 1 to 10, 1 to 8, 1, 2, 3, 4, 5, or 6;
m is an integer from 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5; and
n is an integer from 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5; or
L may also be a linker according to the chemical formula:

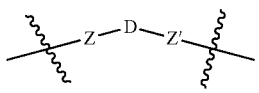

Where Z and Z' are each independently a bond, —$(CH_2)_i$—O, —$(CH_2)_i$—S, —$(CH_2)_i$—N—R,

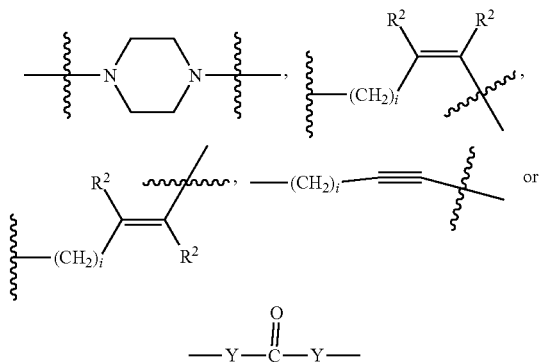

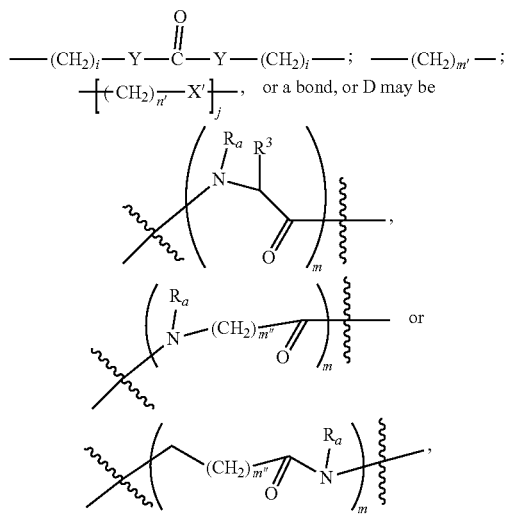

wherein said —(CH$_2$), group, if present in Z or Z', is bonded to [ACM], [CCT$_E$], or an optional difunctional connector group [CON], if present;
Each R is independently H, or a C$_1$-C$_3$ alkyl or alkanol group;
Each R$^2$ is independently H or a C$_1$-C$_3$ alkyl group;
Each Y is independently a bond, O, S or N—R;
Each i is independently 0 to 100, 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5;
D is or a polypropylene glycol or polypropylene-co-polyethylene glycol linker having between 1 and 100 glycol units (1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 52 and 50, 3 and 45);
with the proviso that Z, Z' and D are not each simultaneously bonds;
j is 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5;
m (within this context) is an integer from 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5; and
n (within this context) is an integer from about 1 to 100, about 1 to 75, about 1 to 60, about 1 to 50, about 1 to 45, about 1 to 35, about 1 to 25, about 1 to 20, about 1 to 15, 2 to 10, about 4 to 12, about 5 to 10, about 4 to 6, about 1 to 8, about 1 to 6, about 1 to 5, about 1 to 4, about 1 to 3, etc.).
m' is 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5;
m" is an integer between 0 to 25, preferably 1 to 10, 1 to 8, 0, 1, 2, 3, 4, 5, or 6;
n' is 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5;
X$^1$ is O, S or N—R;
R is as described above;
R$_a$ is H, C$_1$-C$_3$ alkyl or alkanol or forms a cyclic ring with R$^3$ (proline) and R$^3$ is a side chain derived of an amino acid preferably selected from the group consisting of alanine (methyl), arginine (propyleneguanidine), asparagine (methylenecarboxyamide), aspartic acid (ethanoic acid), cysteine (thiol, reduced or oxidized di-thiol), glutamine (ethylcarboxyamide), glutamic acid (propanoic acid), glycine (H), histidine (methyleneimidazole), isoleucine (1-methylpropane), leucine (2-methylpropane), lysine (butyleneamine), methionine (ethylmethylthioether), phenylalanine (benzyl), proline (R$^3$ forms a cyclic ring with R$_a$ and the adjacent nitrogen group to form a pyrrolidine group), serine (methanol), threonine (ethanol, 1-hydroxyethane), tryptophan (methyleneindole), tyrosine (methylene phenol) or valine (isopropyl).

It is noted that each of the linkers (both cleavable and non-cleavable linkers) identified in the present application may be further linked with connector molecules/moieties [CON] molecules/moieties, [ACM] groups and [CCT$_E$] groups through amide groups (which include alkylene groups on either or both sides of the amide group containing one to five methylene units), keto groups (which include alkylene keto groups containing one to five methylene units on either or both sides of the keto group), amine groups (which include alkylene amine groups containing one to five methylene units on either or both sides of the amine group), urethane groups (which include alkylene groups containing one to five methylene units on either or both sides of the urethane moiety), alkylene groups (containing from 1 to 5 methylene units), urea groups (which include alkylene groups containing one to five methylene units on either or both sides of the urethane moiety) amino acids, succinimide groups or other moieties compatible with the linker chemistry in order to link components of the molecules. It is noted that in the case of polyethylene glycol and polypeptide linkers, the use of an additional group (eg, alkylene amine or other group as described above) or a second linker group may be useful for joining the linker to another component of the molecule, including a [CON] group.

Additionally, more than one linker group identified herein may be linked together to form a linker group as otherwise used in the present compounds, consistent with the stability of the linker chemistries. These extended linkers are often, though not exclusively, linked through [CON] connecting groups as otherwise described herein.

In certain embodiments according to the present invention, linker molecules are provided which contain at least one and preferably at least two functional groups through which ACM, CCT$_E$, connector [CON] groups or even additional linker groups may be covalently linked to provide compounds according to the present invention. The functional groups are generally at or are proximally located at the distil ends of a linker molecule and may be electrophilic and/or nucleophilic groups or may be readily functionalized to functional groups (electrophilic and/or nucleophilic groups) which may be used to covalently link other molecules ACM moieties, $CCT_E$ moieties, [CON] molecules or even additional linker molecules) to the linker molecule.

In certain embodiments, functional groups on the linker moiety, include, for example, nucleophilic and/or electrophilic groups which are reactive with a corresponding electrophilic and/or nucleophilic group on the ACM, $CCT_E$ group so that the ACM group or the $CCT_E$ group can be covalent linked or coupled to the linker group. In certain embodiments, $X_{L1}$ and/or $X_{L2}$ groups are nucleophilic groups such as amine groups, hydroxyl groups, sulfhydryl groups, azide groups (for reaction with an alkynyl group to form triazole connector molecules) or nucleophilic carbon groups (e.g., carbanions) which couple and form covalent bonds with a corresponding electrophilic groups such as ester groups (activated), acyl groups (activated), or other electrophilic groups such as trichloromethylmethyliminoester (—O—C=NH(CCl$_3$)), or alkynyl groups (reactive with azide groups) among others, on the ACM or $CCT_E$. Alternatively, these functional groups may be used to link additional linker molecules, ACM and/or $CCT_E$ groups through connector [CON] molecules.

Another difunctional linker molecule for use in the present invention is directly linked to a [ACM] group or more often, a [$CCT_E$] group, as well as a [MULTICON] group as described herein. L $CCT_E$, $CCT_E$ and/or ACM groups optionally include [CON] groups to facilitate the binding of a linker group to the $CCT_E$ group and/or the ACM group.

Common difunctional connector groups [CON] which are used in the present invention, principally to link one end of a linker to another end of a linker to provide a longer linker or to connect a linker (and essentially become integral to the linker) to a ACM or $CCT_E$ group and include the following chemical groups or to:

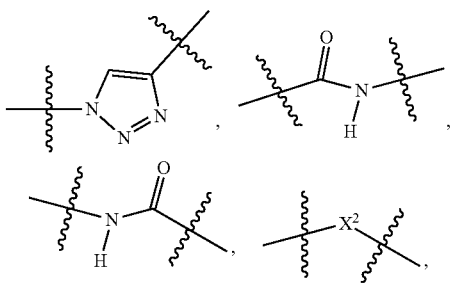

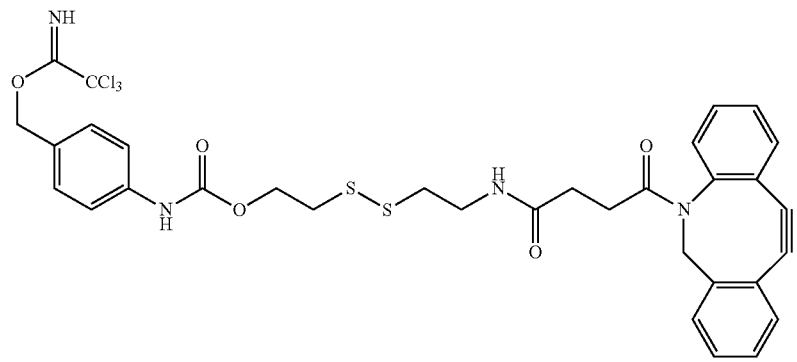

Where the trichloromethylmethyliminoester (—O—C=NH (CCl$_3$) functional group is reactive with a free hydroxyl group and the alkynyl group is reactive with an azido group to form a triazole connector [CON] moiety.

The term "difunctional connector group" or [CON] is used to describe a difunctional group which connects two (or more) portions of a linker group to extend the length of the linker group. In certain embodiments, a linker group is reacted with or forms a [CON] group with another linker group to form an extended linker group or with another moiety such as a ACM moiety or $CCT_E$ moiety to link the linker to that moiety. The reaction product of these groups results in an identifiable connector group [CON] which may be distinguishable from the linker group as otherwise described herein, but is integral to same and essentially forms a portion of the linker group. It is further noted that there is often overlap between the description of the difunctional connector group and the linker group, especially with respect to more common connector groups such as amide groups, oxygen (ether), sulfur (thioether), carbonyl or amine linkages, urea or carbonate —OC(O)O— groups, etc. as otherwise described herein. It is noted that a difunctional connector molecule [CON] used hereunder is often connected to one or two parts of a linker group which binds [ACM] to [$CCT_E$]. Alternatively, a [CON] group may be -continued

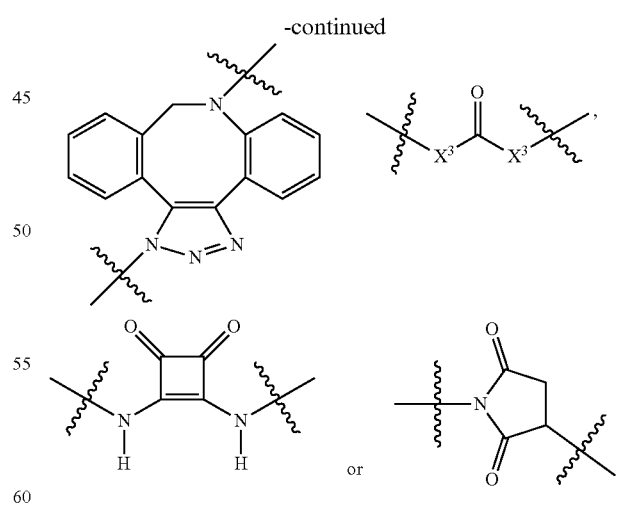

Where $X^2$ is CH$_2$, O, S, NR$^4$, S(O), S(O)$_2$, —S(O)$_2$O, —OS(O)$_2$, or OS(O)$_2$O;

$X^3$ is absent, CH$_2$, O, S, NR$^4$; and

R$^4$ is H, a C$_1$-C$_3$ alkyl or alkanol group, or a —C(O)(C$_1$-C$_3$) group.

In certain embodiments, [CON] is a

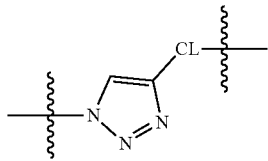

group;
where CL is

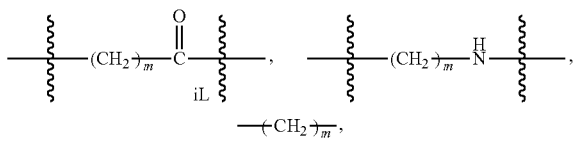

an amide, keto group, urethane or urea;
m in CL is an integer from 0 to 12, often 0, 1, 2, 3, 4, 5 or 6;
and iL is 0 or 1, often 1;

In other embodiments [CON] is a

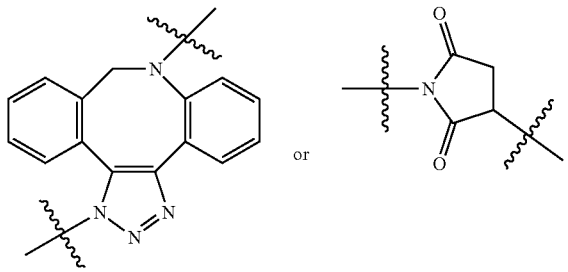 [SMILES: *N1Cc2ccccc2-c2c(nnn2*)-c2ccccc21 ; *C1CC(=O)N(*)C1=O]

group.

In certain embodiments, the [CON] group is often linked through the amine of the triazole or the succinimide moiety to a cleavable or non-cleavable linker or to an ACM group or $CCT_E$ group.

The term "multifunctional connector", symbolized by [MULTICON], is used to describe a chemical group or molecule which is optionally included in chimeric compounds according to the present invention which link at least one or more linker groups (which may be cleavable or non-cleavable), difunctional connector groups (CON), (ACM) groups or ($CCT_E$) groups as otherwise described herein. The connector group is the resulting moiety which forms from the facile condensation of at least three separate chemical fragments which contain reactive groups which can provide connector groups as otherwise described to produce chimeric compounds according to the present invention. It is noted that a multifunctional connector moiety or molecule [MULTICON] is readily distinguishable from a linker in that the multifunctional connector is the result of a specific chemistry which is used to provide chimeric compounds according to the present invention.

Connecting moieties in the present invention include at least one multifunctional moiety or molecule [MULTICON] which contains three or more functional groups which may be used to covalently bind (preferably, through a linker) to at least one [ACM] group (preferably more than one) and at least one [$CCT_E$] group (preferably more than one), thus linking each of these functional groups into a single compound. Multifunctional connector groups for use in the present invention include moities which have at least three or more functional groups which can bind to linkers to which are bound [ACM] and/or [$CCT_E$] groups in order to provide compounds which contain at least one [ACM] and [$CCT_E$] groups, but preferably more than one of each of these groups pursuant to the present invention. These multifunctional connector moieties may also bind to other multifunctional connector molecules in order to create compounds containing a number of [ACM] and [$CCT_E$] groups as defined herein.

Multifunctional connector molecules [MULTICON] comprise any molecule or moiety which contains at least three groups which may be linked to [ACM], [$CCT_E$] and/or linkers (non-labile linkers or labile linkers) and/or other connector groups (including difunctional and multifunctional connector groups) and often comprise five or six-membered aryl or heteroaryl groups (especially six-membered ring groups) exemplified by multifunctional, especially trifunctional or tetrafunctional aryl or heteroaryl groups, including phenyl, pyridyl, pyrimidinyl, 1,3,5-triazinyl, 1,2,3-triazinyl, 1,2,4-triazinyl groups, each of which is substituted with at least 3 and up to 6 functional groups. These functional groups may be derived from nucleophilic or electrophilic groups on the multifunctional connector molecule precursor (the multifunctional connector molecule which forms the [MULTICON] moiety in final compounds according to the present invention) which are condensed onto linker groups (each of which contains, for example an [ACM] group or a [$CCT_E$] group) which contains a group which can be linked to the [MULTICON] moiety. [MULTICON] groups which are used in the present invention preferably include substituted phenyl, pyridyl, pyrimidinyl and 1,3,5-triazinyl, 1,2,3-triazinyl, 1,2,4-triazinyl groups, and other groups of multifunctionality especially including groups according to the chemical structure:

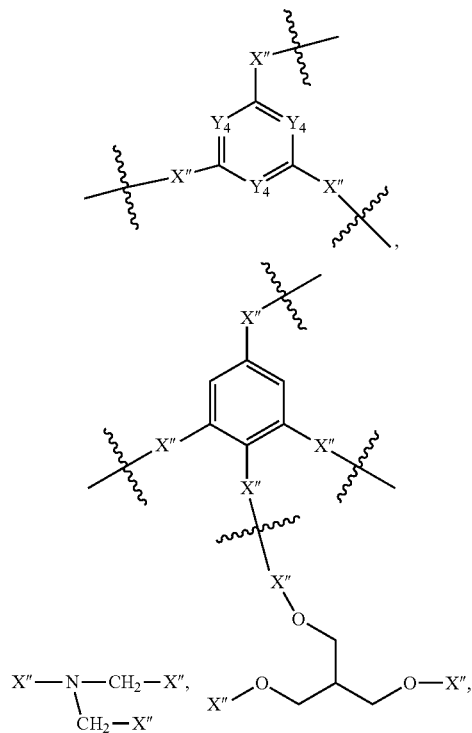

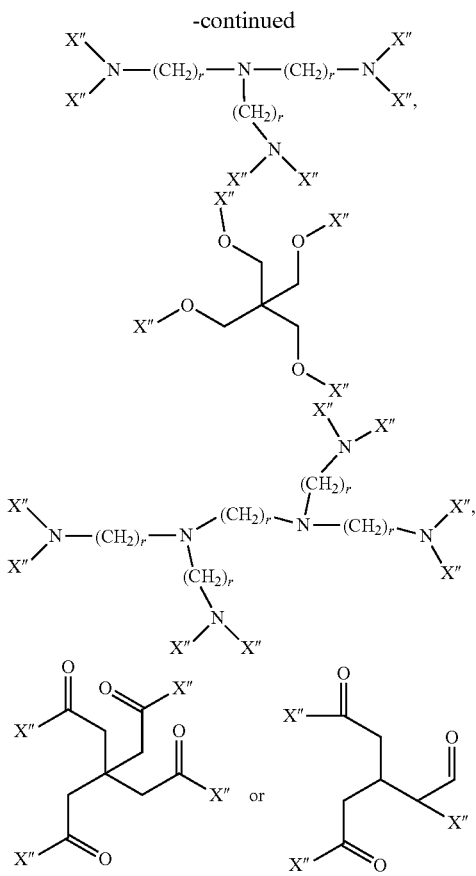

where $Y_4$ is C—H or N; and
Each X" is independently derived from an electrophilic or nucleophilic group, preferably $(CH_2)_{n''}O$, $(CH_2)_{n''}NR^{CON}$, $(CH_2)_{n''}S$,
$(CH_2)_{n''}$ or $(CH_2)_{n''}C=O$;
the substitutent $R^{CON}$ is H or a $C_1$-$C_3$ alkyl, preferably H or $CH_3$,
n" is 0, 1, 2 or 3 and
r is an integer from 1-12, often 1, 2, 3, 4, 5 or 6.

The term "pharmaceutically acceptable salt" or "salt" is used throughout the specification to describe a salt form of one or more of the compositions herein which are presented to increase the solubility of the compound in saline for parenteral delivery or in the gastric juices of the patient's gastrointestinal tract in order to promote dissolution and the bioavailability of the compounds. Pharmaceutically acceptable salts include those derived from pharmaceutically acceptable inorganic or organic bases and acids. Suitable salts include those derived from alkali metals such as potassium and sodium, alkaline earth metals such as calcium, magnesium and ammonium salts, among numerous other acids well known in the pharmaceutical art. Sodium and potassium salts may be preferred as neutralization salts of carboxylic acids and free acid phosphate containing compositions according to the present invention. The term "salt" shall mean any salt consistent with the use of the compounds according to the present invention. In the case where the compounds are used in pharmaceutical indications, including the treatment of prostate cancer, including metastatic prostate cancer, the term "salt" shall mean a pharmaceutically acceptable salt, consistent with the use of the compounds as pharmaceutical agents.

The term "coadministration" shall mean that at least two compounds or compositions are administered to the patient at the same time, such that effective amounts or concentrations of each of the two or more compounds may be found in the patient at a given point in time. Although compounds according to the present invention may be co-administered to a patient at the same time, the term embraces both administration of two or more agents at the same time or at different times, provided that effective concentrations of all coadministered compounds or compositions are found in the subject at a given time. Chimeric antibody-recruiting compounds according to the present invention may be administered with one or more additional anti-cancer agents or other agents which are used to treat or ameliorate the symptoms of cancer, especially prostate cancer, including metastatic prostate cancer.

The term "anticancer agent" or "additional anticancer agent" refers to a compound other than the chimeric compounds according to the present invention which may be used in combination with a compound according to the present invention for the treatment of cancer. Exemplary anticancer agents which may be coadministered in combination with one or more chimeric compounds according to the present invention include, for example, antimetabolites, inhibitors of topoisomerase I and II, alkylating agents and microtubule inhibitors (e.g., taxol), among others. Exemplary anticancer compounds for use in the present invention may include everolimus, trabectedin, abraxane, TLK 286, AV-299, DN-101, pazopanib, GSK690693, RTA 744, ON 9910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhibitor, a c-MET inhibitor, a PARP inhibitor, a Cdk inhibitor, an EGFR TK inhibitor, an IGFR-TK inhibitor, an anti-HGF antibody, a PI3 kinase inhibitors, an AKT inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofaturnurnab (Arzerra), zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR$_1$ KRX-0402, lucanthone, LY 317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, irinotecan, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1 H pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES(diethylstilbestrol), estradiol, estrogen, conjugated estrogen, bevacizumab, IMC-1C11, CHIR-258,); 3-[5-(methylsulfonylpiperadinemethyl)-indolylj-quinolone, vatalanib, AG-013736, AVE-0005, the acetate salt of [D-Ser(Bu t) 6, Azgly 10] (pyro-Glu-His-Trp-Ser-Tyr-D-Ser(Bu t)-Leu-Arg-Pro-Azgly-NH$_2$ acetate [$C_{59}H_{84}N_{18}Oi_4$-$(C_2H_4O_2)_X$ where x=1 to 2.4], goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, amsacrine, anagrelide, L-asparaginase, Bacillus Calmette-Guerin (BCG) vaccine, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gemcitabine, gleevac, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mercaptopurine, deoxycoformycin, calcitriol valrubicin, mithramycin, vinblastine, vinorelbine, topotecan, razoxin, marimastat, COL-3, neovastat, BMS-275291 squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin difinox, gefitinib, bortezimib, paclitaxel, irinotecan, topotecan, doxorubicin, docetaxel, vinorelbine, bevacizumab (monoclonal antibody) and erbitux, cremophor-free paclitaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonists, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa and darbepoetin alfa, among others.

In addition to anticancer agents, a number of other agents may be coadministered with chimeric compounds according to the present invention in the treatment of cancer. These include active agents, minerals, vitamins and nutritional supplements which have shown some efficacy in inhibiting cancer tissue or its growth or are otherwise useful in the treatment of cancer. For example, one or more of dietary selenium, vitamin E, lycopene, soy foods, curcumin (turmeric), vitamin D, green tea, omega-3 fatty acids and phytoestrogens, including beta-sitosterol, may be utilized in combination with the present compounds to treat cancer.

Without not being limited by way of theory, anticancer compounds according to the present invention which contain a cancer cell targeting element ($CCT_E$) and an anticancer moiety (ACM) selectively bind to cancer cells and through that binding, facilitate the introduction of the (ACM) moiety into the cancer cell selectively, where, the compound, inside the cell or during transport into the cancer cell, the cleavable linker is cleaved from the cancer cell targeting moiety, providing an agent for intercalating and/or damaging through breakage the cancer cell's DNA or other anticancer mechanism and causing cell death.

Pharmaceutical compositions comprising combinations of an effective amount of at least one compound disclosed herein, often a difunctional chimeric compound (containing at least one ACM and at least one $CCT_E$) according to the present invention, and one or more of the compounds as otherwise described herein, all in effective amounts, in combination with a pharmaceutically effective amount of a carrier, additive or excipient, represents a further aspect of the present invention. These may be used in combination with at least one additional, optional anticancer agent as otherwise disclosed herein.

The compositions of the present invention may be formulated in a conventional manner using one or more pharmaceutically acceptable carriers and may also be administered in controlled-release formulations. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium tri silicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir, among others. The term "parenteral" as used herein includes subcutaneous, intravenous, intramuscular, intra-articular, intra-synovial, intrasternal, intrathecal, intra-hepatic, intralesional and intracranial injection or infusion techniques. Preferably, the compositions are administered orally (including via intubation through the mouth or nose into the stomach), intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1, 3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions of this invention may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially to treat skin cancers, psoriasis or other diseases which occur in or on the skin. Suitable topical formulations are readily prepared for each of these areas or organs. Topical application for the lower intestinal tract can be effected in a rectal suppository formulation (see above) or in a suitable enema formulation. Topically-acceptable transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water.

Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of compound in a pharmaceutical composition of the instant invention that may be combined with the carrier materials to produce a single dosage form will vary depending upon the host and disease treated, the particular mode of administration. Preferably, the compositions should be formulated to contain between about 0.05 milligram to about 750 milligrams or more, more preferably about 1 milligram to about 600 milligrams, and even more preferably about 10 milligrams to about 500 milligrams of active ingredient, alone or in combination with at least one additional compound which may be used to treat cancer, prostate cancer or metastatic prostate cancer or a secondary effect or condition thereof.

Methods of treating patients or subjects in need for a particular disease state or condition as otherwise described herein, especially cancer, comprise administration of an effective amount of a pharmaceutical composition comprising therapeutic amounts of one or more of the novel compounds described herein and optionally at least one additional bioactive (e.g. anti-cancer) agent according to the present invention. The amount of active ingredient(s) used in the methods of treatment of the instant invention that may be combined with the carrier materials to produce a single dosage form will vary depending upon the host treated, the particular mode of administration. For example, the compositions could be formulated so that a therapeutically effective dose of between about 0.01, 0.1, 1, 5, 10, 15, 20, 25, 30, 35, 40, 45, 50, 55, 60, 65, 70, 75, 80, 85, 90 or 100 mg/kg of patient/day or in some embodiments, greater than 100, 110, 120, 130, 140, 150, 160, 170, 180, 190 or 200 mg/kg of the novel compounds can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

A patient or subject (e.g. a male human) suffering from cancer can be treated by administering to the patient (subject) an effective amount of a chimeric compound according to the present invention including pharmaceutically acceptable salts, solvates or polymorphs, thereof optionally in a pharmaceutically acceptable carrier or diluent, either alone, or in combination with other known anticancer or pharmaceutical agents, preferably agents which can assist in treating cancer, including metastatic cancer or ameliorate the secondary effects and conditions associated with cancer. This treatment can also be administered in conjunction with other conventional cancer therapies, such as radiation treatment or surgery.

The present compounds, alone or in combination with other agents as described herein, can be administered by any appropriate route, for example, orally, parenterally, intravenously, intradermally, subcutaneously, or topically, in liquid, cream, gel, or solid form, or by aerosol form.

The active compound is included in the pharmaceutically acceptable carrier or diluent in an amount sufficient to deliver to a patient a therapeutically effective amount for the desired indication, without causing serious toxic effects in the patient treated. A preferred dose of the active compound for all of the herein-mentioned conditions is in the range from about 10 ng/kg to 1000 mg/kg, preferably 0.1 to 300 mg/kg per day, more generally 0.5 to about 25 mg per kilogram body weight of the recipient/patient per day. A typical topical dosage will range from about 0.01-3% wt/wt in a suitable carrier.

The term "unit dose" or "dosage" refers to physically discrete units suitable for use in a subject, each unit containing a predetermined quantity of the therapeutic composition calculated to produce the desired anti-cancer responses discussed above in association with its administration, i.e., the appropriate route and treatment regimen. The quantity to be administered, both according to number of treatments and unit dose, depends on the effect desired, but generally falls within the ranges described above. The actual dosage amount of a composition of the present embodiments administered to a patient or subject can be determined by physical and physiological factors, such as body weight, the age, health, and sex of the subject, the type of disease being treated, the extent of disease penetration, previous or concurrent therapeutic interventions, idiopathy of the patient, the route of administration, and the potency, stability, and toxicity of the particular therapeutic substance. For example, a dose may also comprise from about 1 μg/kg/body weight to about 1000 mg/kg/body weight (this such range includes intervening doses) or more per administration, and any range derivable therein. In non-limiting examples of a derivable range from the numbers listed herein, a range of about 5 μg/kg/body weight to about 100 mg/kg/body weight, about 5 μg/kg/body weight to about 500 mg/kg/body weight, etc., also can be administered. The practitioner responsible for administration will, in any event, determine the concentration of active ingredient(s) in a composition and appropriate dose(s) for the individual subject.

The compound is conveniently administered in any suitable unit dosage form, including but not limited to one containing less than 1 mg, 1 mg to 3000 mg, preferably 5 to 500 mg of active ingredient per unit dosage form. An oral dosage of about 25-250 mg is often convenient.

The active ingredient is preferably administered to achieve peak plasma concentrations of the active compound of about 0.00001-30 mM, preferably about 0.1-30 μM. This may be achieved, for example, by the intravenous injection of a solution or formulation of the active ingredient, optionally in saline, or an aqueous medium or administered as a bolus of the active ingredient. Oral administration is also appropriate to generate effective plasma concentrations of active agent.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Oral compositions will generally include an inert diluent or an edible carrier. They may be enclosed in gelatin capsules or compressed into tablets. For the purpose of oral therapeutic administration, the active compound or its prodrug derivative can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or enteric agents.

The active compound or pharmaceutically acceptable salt thereof can be administered as a component of an elixir, suspension, syrup, wafer, chewing gum or the like. A syrup may contain, in addition to the active compounds, sucrose as a sweetening agent and certain preservatives, dyes and colorings and flavors.

The active compound or pharmaceutically acceptable salts thereof can also be mixed with other active materials that do not impair the desired action, or with materials that supplement the desired action, such as other anticancer agents, antibiotics, antifungals, antiinflammatories, or antiviral compounds. In certain preferred aspects of the invention, one or more chimeric antibody-recruiting compound according to the present invention is coadministered with another anticancer agent and/or another bioactive agent, as otherwise described herein.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In one embodiment, the active compounds are prepared with carriers that will protect the compound against rapid elimination from the body, such as a controlled and/or sustained release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions or cholestosomes may also be pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin fACM of dried lipid on the surface of the container. An aqueous solution of the active compound are then introduced into the container. The container is then swirled by hand to free lipid material from the sides of the container and to disperse lipid aggregates, thereby forming the liposomal suspension.

Combination Treatments

In certain embodiments, the compositions and methods of the present embodiments may involve an antibody or an antibody fragment against a cancer target to inhibit its activity in cancer cell proliferation, in combination with a second or additional therapy. Such therapy can be applied in the treatment of any disease that is associated with cell proliferation. In preferred embodiments, for example, the disease is cancer.

The methods and compositions, including combination therapies, enhance the therapeutic or protective effect, and/or increase the therapeutic effect of another anti-cancer or anti-hyperproliferative therapy. Therapeutic and prophylactic methods and compositions can be provided in a combined amount effective to achieve the desired effect, such as the killing of a cancer cell and/or the inhibition of cellular hyperproliferation. This process may involve contacting the cells with both an antibody or antibody fragment and a second therapy. A tissue, tumor, or cell can be contacted with one or more compositions or pharmacological formulation(s) comprising one or more of the agents (i.e., antibody or antibody fragment or an anti-cancer agent), or by contacting the tissue, tumor, and/or cell with two or more distinct compositions or formulations, wherein one composition provides 1) an antibody or antibody fragment, 2) an anti-cancer agent, or 3) both an antibody or antibody fragment and an anti-cancer agent. Also, it is contemplated that such a combination therapy can be used in conjunction with chemotherapy, radiotherapy, surgical therapy, or immunotherapy.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing, for example, both agents are delivered to a cell in a combined amount effective to kill the cell or prevent it from dividing.

An inhibitory antibody may be administered before, during, after, or in various combinations relative to an anti-cancer treatment. The administrations may be in intervals ranging from concurrently to minutes to days to weeks. In embodiments where the antibody or antibody fragment is provided to a patient separately from an anti-cancer agent, one would generally ensure that a significant period of time did not expire between the time of each delivery, such that the two compounds would still be able to exert an advantageously combined effect on the patient. In such instances, it is contemplated that one may provide a patient with the antibody therapy and the anti-cancer therapy within about 12 to 24 or 72 h of each other and, more particularly, within about 6-12 h of each other. In some situations it may be desirable to extend the time period for treatment significantly where several days (2, 3, 4, 5, 6, or 7) to several weeks (1, 2, 3, 4, 5, 6, 7, or 8) lapse between respective administrations.

In certain embodiments, a course of treatment will last 1-90 days or more (this such range includes intervening days). It is contemplated that one agent may be given on any day of day 1 to day 90 (this such range includes intervening days) or any combination thereof, and another agent is given on any day of day 1 to day 90 (this such range includes intervening days) or any combination thereof. Within a single day (24-hour period), the patient may be given one or multiple administrations of the agent(s). Moreover, after a course of treatment, it is contemplated that there may be a period of time at which no anti-cancer treatment is administered. This time period may last 1-7 days, and/or 1-5 weeks, and/or 1-12 months or more (this such range includes intervening days), depending on the condition of the patient, such as their prognosis, strength, health, etc. It is expected that the treatment cycles would be repeated as necessary.

Administration of any compound or therapy of the present embodiments to a patient will follow general protocols for the administration of such compounds, taking into account the toxicity, if any, of the agents. Therefore, in some embodiments there is a step of monitoring toxicity that is attributable to combination therapy.

Chemotherapy

A wide variety of chemotherapeutic agents/additional anti-cancer agents may be used in accordance with the present embodiments. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Radiotherapy

Other factors that cause DNA damage and have been used extensively include what are commonly known as γ-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287), and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

Immunotherapy

The skilled practitioner will understand that additional immunotherapies may be used in combination or in conjunction with methods of the embodiments. In the context of cancer treatment, immunotherapeutics, generally, rely on the use of immune effector cells and molecules to target and destroy cancer cells. Rituximab (RITUXAN®) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve as a targeting agent. Alternatively, the effector may be a lymphocyte carrying a surface molecule that interacts, either directly or indirectly, with a tumor cell target. Various effector cells include cytotoxic T cells and NK cells Antibody-drug conjugates have emerged as a breakthrough approach to the development of cancer therapeutics. Cancer is one of the leading causes of deaths in the world. Antibody-drug conjugates (ADCs) comprise monoclonal antibodies (MAbs) that are covalently linked to cell-killing drugs/moieties pursuant to the present invention. This approach combines the high specificity of MAbs against their antigen targets with highly potent cytotoxic drugs, resulting in "armed" MAbs that deliver the payload (drug) to tumor cells with enriched levels of the antigen (Carter et al., 2008; Teicher 2014; Leal et al., 2014). Targeted delivery of the drug also minimizes its exposure in normal tissues, resulting in decreased toxicity and improved therapeutic index. There are currently more than 30 ADC drug candidates in various stages of clinical trials for cancer treatment (Leal et al., 2014). As antibody engineering and linker-payload optimization are becoming more and more mature, the discovery and development of new ADCs such as those according to the present invention are increasingly dependent on the identification and validation of new targets that are suitable to this approach (Teicher 2009) and the generation of targeting MAbs. Two criteria for ADC targets are upregulated/high levels of expression in tumor cells and robust internalization.

In one aspect of immunotherapy, the tumor cell must bear some marker that is amenable to targeting, i.e., is not present on the majority of other cells. Many tumor markers exist and any of these may be suitable for targeting in the context of the present embodiments. Common tumor markers include CD20, carcinoembryonic antigen, tyrosinase (p97), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies currently under investigation or in use are immune adjuvants, e.g., *Mycobacterium bovis, Plasmodium falciparum*, dinitrochlorobenzene, and aromatic compounds (U.S. Pat. Nos. 5,801,005 and 5,739,169; Hui and Hashimoto, 1998; Christodoulides et al., 1998); cytokine therapy, e.g., interferons α, β, and γ, IL-1, GM-CSF, and TNF (Bukowski et al., 1998; Davidson et al., 1998; Hellstrand et al., 1998); gene therapy, e.g., TNF, IL-1, IL-2, and p53 (Qin et al., 1998; Austin-Ward and Villaseca, 1998; U.S. Pat. Nos. 5,830,880 and 5,846,945); and monoclonal antibodies, e.g., anti-CD20, anti-ganglioside GM2, and anti-p185 (Hollander, 2012; Hanibuchi et al., 1998; U.S. Pat. No. 5,824,311). It is contemplated that one or more anti-cancer therapies may be employed with the antibody therapies described herein.

Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present embodiments, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

Other Agents

It is contemplated that other agents may be used in combination with certain aspects of the present embodiments to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present embodiments to improve the anti-hyperproliferative efficacy of the treatments. Inhibitors of cell adhesion are contemplated to improve the efficacy of the present embodiments. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present embodiments to improve the treatment efficacy.

Chemical Synthesis

In order to synthesize compounds according to the present invention, chemical synthetic steps which are well known in the art are used. These often involve simple condensation reactions. In general, compounds according to the present invention are produced from a precursor compound which contains a moiety In certain embodiments, chimeric molecules are produced which Chimeric molecules according to the present invention are synthesized by condensing a linker molecule onto a functional group of an ACM group or a $CCT_E$ group and thereafter, either extending the linker which is covalently linked to the ACM group (or $CCT_E$) to a $CCT_E$ (or ACM group). Various approaches may be used. We provide exemplary chemistry for providing numerous compounds according to the present invention.

General Experimental Methods.

UV Spectroscopy.

UV thermal denaturation samples were prepared by mixing calf thymus DNA [32.0 mM base pairs (bps)] in 2.09 mM $NaH_2PO_4$, 7.13 mM $Na_2HPO_4$, 928 μM $Na_2EDTA$, 1.01 mM DMSO, pH 7.18 to a final volume of 1.0 mL. Samples were subjected to sonication (6 h) at 25° C. to effect complete dissolution. After incubation with 15a, 15b, 17a, and 17b for 5 min, 1 h, 3 h, 6 h, or 15 h, the UV thermal denaturation spectra of the samples were recorded at 260 nm as a function of temperature (55→80° C., heating rate: 0.5° C./min). First derivative plots were used to determine the denaturation temperature.

Electrophoretic Gel Assay.

The 4,163 bp plasmid pBR322 was propagated in DH5a, isolated by MaxiPrep (Qiagen), and linearized with 5 U/μg EcoRI (NEB). The cut plasmid was column purified and eluted into 10 mM Tris pH 8.0. For each reaction, 130 ng of DNA (20 μM base pairs) was incubated with compound in a 10 μL total volume. Reactions proceeded for 15 h at 37° C., unless otherwise noted. Compounds were diluted in DMSO such that each reaction consisted of a fixed 5% DMSO concentration. Pure MMS (Alfa Aesar) and cisplatin (Biovision) stock solutions were diluted into DMSO immediately prior to use. After incubation, 35 μL of denaturation buffer (6% sucrose, 1% sodium hydroxide, 0.04% bromophenol blue) was added to each reaction. Non-denatured control samples were diluted with 6% sucrose, 0.04% bromophenol blue. Samples were vortexed for 1 min, left at room temperature for 15 min, and then immediately frozen at −80° C. Thawed samples were then loaded onto a 1% agarose Tris-Borate-EDTA (TBE) gel stained with SybrGold (Molecular Probes) and run in TBE buffer for 1 hour at 120V.

General Experimental Procedures.

All reactions were performed in single-neck, flame-dried, round-bottomed flasks fitted with rubber septa under a positive pressure of nitrogen unless otherwise noted. Air- and moisture-sensitive liquids were transferred via syringe or stainless steel cannula, or were handled in a nitrogen-filled drybox (working oxygen level <10 ppm). Organic solutions were concentrated by rotary evaporation at 28-32° C. Flash-column chromatography was performed as described by Still et al.,[1] employing silica gel (60 Å, 40-63 µm particle size) purchased from Sorbent Technologies (Atlanta, Ga.). Anion-exchange chromatography was performed as described by Béland et al.,[2] employing trimethylamine acetate-functionalized silica gel (SiliaBond® TMA Acetate). Analytical thin-layered chromatography (TLC) was performed using glass plates pre-coated with silica gel (0.25 mm, 60 Å pore size) impregnated with a fluorescent indicator (254 nm). TLC plates were visualized by exposure to ultraviolet light (UV).

Materials.

Commercial solvents and reagents were used as received with the following exceptions. Dichloromethane, ether and N,N-dimethylformamide were purified according to the method of Pangborn et al.[3] Triethylamine was distilled from calcium hydride under an atmosphere of argon immediately before use. Di-iso-propylamine was distilled from calcium hydride and was stored under nitrogen. Methanol was distilled from magnesium turnings under an atmosphere of nitrogen immediately before use. Tetrahydrofuran was distilled from sodium-benzophenone under an atmosphere of nitrogen immediately before use. Deoxyribonucleic acid sodium salt from calf thymus (Type I, fibers) was purchased from Sigma Aldrich. Trimethylamine acetate-functionalized silica gel (SiliaBond® TMA Acetate) was purchased from SiliCycle (Quebec City, Calif.). tert-butyl-(S)-2-methyl-5-oxopyrrolidine-1-carboxylate (S1) was prepared according to the method of Tanaka, A.; Usuki, T. *Tetrahedron Lett.* 2011, 52, 5036. 2'-((3-(1-aminocyclopropyl)-3-oxopropanamido)methyl)-[2,4'-bithiazole]-4-carboxylic acid hydrochloride (11) was prepared according to the method of Healy, A. R.; Vizcaino, M. I.; Crawford, J. M.; Herzon, S. B. *J. Am. Chem. Soc.* 2016, 138, 5426.

Instrumentation.

Proton nuclear magnetic resonance spectra ($^1$H NMR) were recorded at 500 or 600 MHz at 24° C., unless otherwise noted. Chemical shifts are expressed in parts per million (ppm, δ scale) downfield from tetramethylsilane and are referenced to residual protium in the NMR solvent ($CD_2Cl_2$, δ 5.32; $CD_3OD$, δ 3.31; $C_2D_6OS$, δ 2.50). Data are represented as follows: chemical shift, multiplicity (s=singlet, d=doublet, t=triplet, q=quartet, m=multiplet and/or multiple resonances, br=broad, app=apparent), coupling constant in Hertz, integration, and assignment. Proton-decoupled carbon nuclear magnetic resonance spectra ($^{13}$C NMR) were recorded at 125 MHz at 24° C., unless otherwise noted. Chemical shifts are expressed in parts per million (ppm, δ scale) downfield from tetramethylsilane and are referenced to the carbon resonances of the solvent ($CD_2Cl_2$, δ 54.0; $CD_3OD$, δ 49.0; $C_2D_6OS$, δ 39.5). Signals of protons and carbons were assigned, as far as possible, by using the following two dimensional NMR spectroscopy techniques: [$^1$H, $^1$H] COSY (Correlation Spectroscopy), [$^1$H, $^{13}$C] HSQC (Heteronuclear Single Quantum Coherence) and long range [$^1$H, $^{13}$C] HMBC (Heteronuclear Multiple Bond Connectivity). Attenuated total reflectance Fourier transform infrared (ATR-FTIR) spectra were obtained using a Thermo Electron Corporation Nicolet 6700 FTIR spectrometer referenced to a polystyrene standard. Data are represented as follows: frequency of absorption ($cm^{-1}$), intensity of absorption (s=strong, m=medium, w=weak, br=broad). Analytical ultra high-performance liquid chromatography/mass spectrometry (UPLC/MS) was performed on a Waters UPLC/MS instrument equipped with a reverse-phase $C_{18}$ column (1.7 µm particle size, 2.1×50 mm), dual atmospheric pressure chemical ionization (API)/electrospray (ESI) mass spectrometry detector, and photodiode array detector. Samples were eluted with a linear gradient of 5% acetonitrile-water containing 0.1% formic acid→100% acetonitrile containing 0.1% formic acid over 0.75 min, followed by 100% acetonitrile containing 0.1% formic acid for 0.75 min, at a flow rate of 800 µL/min. High-resolution mass spectrometry (HRMS) were obtained on a Waters UPLC/HRMS instrument equipped with a dual API/ESI high-resolution mass spectrometry detector and photodiode array detector. Unless otherwise noted, samples were eluted over a reverse-phase $C_{18}$ column (1.7 µm particle size, 2.1×50 mm) with a linear gradient of 5% acetonitrile-water containing 0.1% formic acid→95% acetonitrile-water containing 0.1% formic acid for 1 min, at a flow rate of 600 µL/min. Optical rotations were measured on a Perkin Elmer polarimeter equipped with a sodium (589 nm, D) lamp. Optical rotation data are represented as follows: specific rotation ($[\alpha]_\lambda^T$), concentration (g/100 mL), and solvent. UV spectra were recorded on a Cary 3E UV/Vis spectrophotometer equipped with a thermoelectrically controlled 12-cell holder. High precision quartz SUPRASIL cells with a 1 cm path length were used for all absorbance studies.

Chemical Synthetic Procedures.

Synthesis of the β-Ketothioester 10:

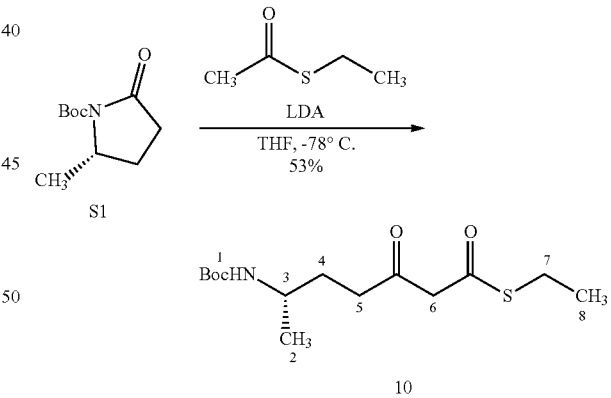

Ethyl thioacetate (2.08 mL, 19.5 mmol, 1.30 equiv) was added dropwise via syringe to a solution of lithium di-iso-propylamide (19.5 mmol, 1.30 equiv) in tetrahydrofuran (75 mL) at −78° C. The reaction mixture was stirred for 30 min at −78° C. A solution of the imide S1 (3.00 g, 15.1 mmol, 1 equiv) in tetrahydrofuran (28 mL) was added dropwise via cannula to the reaction mixture. The resulting mixture was stirred for 3 h at −78° C. The product mixture was diluted sequentially with saturated aqueous ammonium chloride solution (30 mL) and ethyl acetate (50 mL). The diluted product mixture was transferred to a separatory funnel and the layers that formed were separated. The aqueous layer was extracted with ethyl acetate (2×50 mL). The organic layers were combined and the combined organic layers were washed with saturated aqueous sodium chloride solution (30 mL). The washed organic layer was dried over sodium sulfate. The dried solution was filtered and the filtrate was concentrated. The residue obtained was purified by flash-column chromatography (eluting with 5% ethyl acetate-hexanes initially, grading to 20% ethyl acetate-hexanes, linear gradient) to provide the β-ketothioester 10 as a light pink solid (2.40 g, 53%).

$^1$H NMR (500 MHz, CD$_2$Cl$_2$) δ 4.38 (bs, 1H), 3.66 (s, 2H, H$_6$), 3.58 (m, 1H, H$_3$), 2.90 (q, J=6.9 Hz, 2H, H$_7$), 2.65-2.50 (m, 2H, H$_5$), 1.77-1.67 (m, 1H, H$_4$), 1.62-1.52 (m, 1H, H$_4$), 1.41 (s, 9H, H$_1$), 1.25 (t, J=7.8 Hz, 3H, H$_8$), 1.10 (d, J=6.6 Hz, 3H, H$_2$). $^{13}$C NMR (126 MHz, CD$_2$Cl$_2$) δ 202.4 (C), 192.6 (C), 155.9 (C), 79.3 (C), 58.2 (CH$_2$), 46.4 (CH), 40.4 (CH$_2$), 31.2 (CH$_2$), 28.7 (CH$_3$), 24.5 (CH$_2$), 21.8 (CH$_3$), 14.9 (CH$_3$). IR (ATR-FTIR), cm$^{-1}$: 3387 (m), 2797 (w), 2929 (w), 1717 (w), 1683 (s), 1512 (s), 1310 (m), 1170 (m), 1051 (s), 541 (m). HRMS-CI (m/z): [M+Na]$^+$ calcd for C$_{14}$H$_{25}$NNaO$_4$S, 326.1397; found, 326.1399. [α]$_D^{20}$ +8.0 (c 1.0, CH$_2$Cl$_2$).

Synthesis of the Pyridone 16:

$^1$H NMR (600 MHz, DMSO-d$_6$) δ 8.48 (bs, 1H, H$_6$), 8.39 (s, 1H, H$_{11}$), 8.25 (s, 1H, H$_{10}$), 6.80 (d, J=8.0 Hz, 1H), 6.17 (s, 1H, H$_8$), 5.60 (d, J=16.0 Hz, 1H, H$_9$), 5.49 (d, J=15.9 Hz, 1H, H$_9$), 3.63-3.52 (m, 1H, H$_3$), 3.53-3.45 (m, 1H, H$_5$), 3.32-3.14 (m, 1H, H$_5$), 1.75-1.60 (m, 2H, H$_4$), 1.37 (app t, J=2.7 Hz, 2H, H$_7$), 1.35 (app t, J=2.8 Hz, 1H, H$_7$), 1.30 (s, 9H, HA 1.06 (d, J=6.6 Hz, 3H, H$_2$). $^{13}$C NMR (151 MHz, DMSO-d$_6$) δ 166.9 (C), 166.7 (C), 162.3 (C), 161.8 (C), 161.6 (C), 159.9 (C), 155.1 (C), 153.0 (C), 149.3 (C), 147.2 (C), 128.3 (CH), 118.7 (CH), 109.7 (C), 103.3 (CH), 77.4 (C), 46.1 (CH), 44.2 (CH$_2$), 39.7 (C), 35.5 (CH$_2$), 28.2 (CH$_3$), 24.1 (CH$_2$), 20.7 (CH$_3$), 15.2 (CH$_2$). IR (ATR-FTIR), cm$^{-1}$: 3327 (w), 3121 (w), 2971 (w), 2355 (br w), 1720 (w), 1702 (w), 1674 (m), 1649 (s), 1571 (m), 1518 (m), 1171 (m), 578 (s). HRMS-CI (m/z): [M+H]$^+$ calcd for C$_{26}$H$_{30}$N$_5$O$_6$S$_2$, 572.1632; found, 572.1630. [α]$_D^{20}$ −64.0 (c 0.5, DMSO).

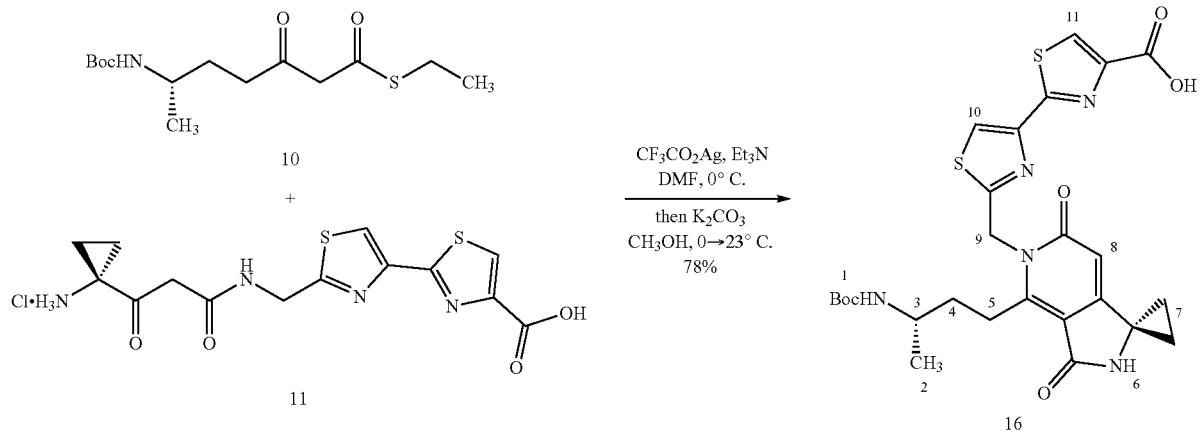

Silver trifluoroacetate (410 mg, 1.86 mmol, 2.00 equiv) was added to a solution of triethylamine (518 µL, 3.71 mmol, 4.00 equiv) and the amine 11 (374 mg, 930 µmol, 1 equiv) in N,N-dimethylformamide (6.0 mL) at 0° C. A solution of the β-ketothioester 10 (366 mg, 1.21 mmol, 1.30 equiv) in N,N-dimethylformamide (2.0 mL) was added dropwise via syringe to the reaction mixture. The reaction vessel was covered with foil to exclude light and the reaction mixture was stirred for 1 h at 0° C. Potassium carbonate (385 mg, 2.79 mmol, 3.00 equiv) and methanol (8.0 mL) were then added in sequence to the reaction mixture at 0° C. The reaction mixture was stirred for 30 min at 0° C. The heterogeneous product mixture was filtered through a fritted funnel. The filter cake was washed with methanol (10 mL). The filtrates were combined and the combined filtrates were concentrated. The residue obtained was applied to a trim-ethylamine acetate-functionalized silica column (Si-TMA acetate; eluting with 0.5% formic acid-acetonitrile). The fractions containing the product 16 were collected, combined, and concentrated to provide the pyridone 16 as a white solid (414 mg, 78%).

Synthesis of the Amide S2:

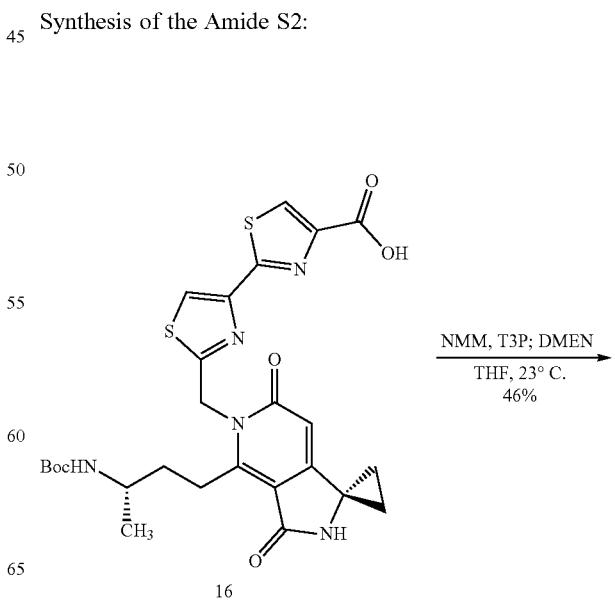

51
-continued

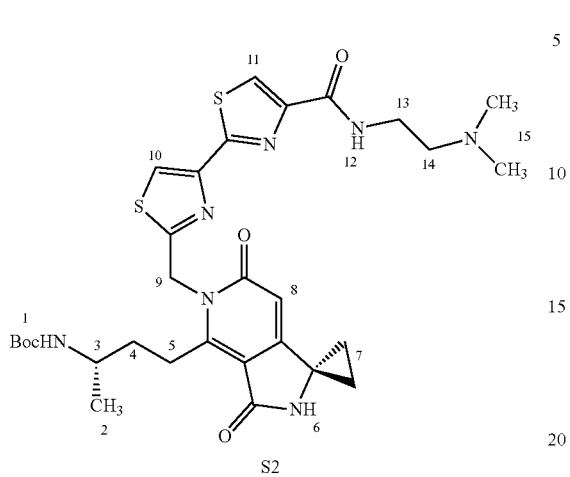

A solution of T3P in ethyl acetate (50 wt %, 54.7 µL, 91.8 µmol, 1.50 equiv) and 4-methylmorpholine (33.7 µL, 306 µmol, 5.00 equiv) were added in sequence to a solution of the acid 16 (35.0 mg, 61.2 µmol, 1 equiv) in tetrahydrofuran (790 µL) at 23° C. N,N-Dimethylethylenediamine (16.7 µL, 153 µmol, 2.50 equiv) was then added to the reaction mixture. The resulting mixture was stirred for 7 h at 23° C. The product mixture was concentrated. The concentrated product mixture was diluted with ethyl acetate (10 mL). The diluted product mixture was poured into a separatory funnel that had been charged with saturated aqueous sodium bicarbonate solution (5.0 mL) and the layers that formed were separated. The aqueous layer was extracted with ethyl acetate (2×10 mL). The organic layers were combined and the combined organic layers were dried over sodium sulfate. The dried solution was filtered and the filtrate was concentrated to provide the amide S2 as a white solid (18.1 mg, 46%). The product so obtained was used without further purification. $^1$H NMR (500 MHz, CD$_2$Cl$_2$) δ 8.06 (s, 1H, H$_{11}$), 8.01 (s, 1H, H$_{10}$), 7.64 (bs, 1H, H$_{12}$), 6.33 (bs, 1H, H$_6$), 6.01 (s, 1H, H$_8$), 5.62 (d, J=15.0 Hz, 1H, H$_9$), 5.55 (d, J=14.2 Hz, 1H, H$_9$), 5.38 (d, J=7.4 Hz, 1H), 3.82-3.74 (m, 1H, H$_3$), 3.66-3.58 (m, 1H, H$_5$), 3.51 (app q, J=5.9 Hz, 2H, H$_{13}$), 3.48-3.41 (m, 1H, H$_5$), 2.51 (t, J=6.1 Hz, 2H, H$_{14}$), 2.27 (s, 6H, H$_{15}$), 1.89-1.81 (m, 1H, H$_4$), 1.80-1.69 (m, 1H, H$_4$), 1.52-1.45 (m, 2H, H$_7$), 1.41 (s, 9H, H$_1$), 1.37-1.32 (m, 2H, H$_7$), 1.19 (d, J=6.5 Hz, 3H, H$_2$). $^{13}$C NMR (126 MHz, CD$_2$Cl2) δ 168.4 (C), 166.0 (C), 163.1 (C), 162.7 (C), 161.2 (C), 160.5 (C), 156.1 (C), 154.4 (C), 151.8 (C), 148.5 (C), 123.8 (CH), 119.2 (CH), 110.3 (C), 103.9 (CH), 79.2 (C), 58.7 (CH$_2$), 47.1 (CH), 45.7 (CH$_3$), 45.1 (CH$_2$), 40.6 (C), 37.5 (CH$_2$), 36.1 (CH$_2$), 28.7 (CH$_3$), 25.0 (CH$_2$), 21.3 (CH$_3$), 16.2 (CH$_2$). IR (ATR-FTIR), cm$^{-1}$: 3327 (br w), 2972 (w), 1694 (w), 1651 (s), 1541 (m), 1250 (m), 1165 (m), 568 (m). HRMS-CI (m/z): [M+H]$^+$ calcd for C$_{30}$H$_{40}$N$_7$O$_5$S$_2$, 642.2527; found, 642.2532. [α]$_D^{20}$ −125.8 (c 0.93, CH$_3$OH).

52
Synthesis of the Amide 17a:

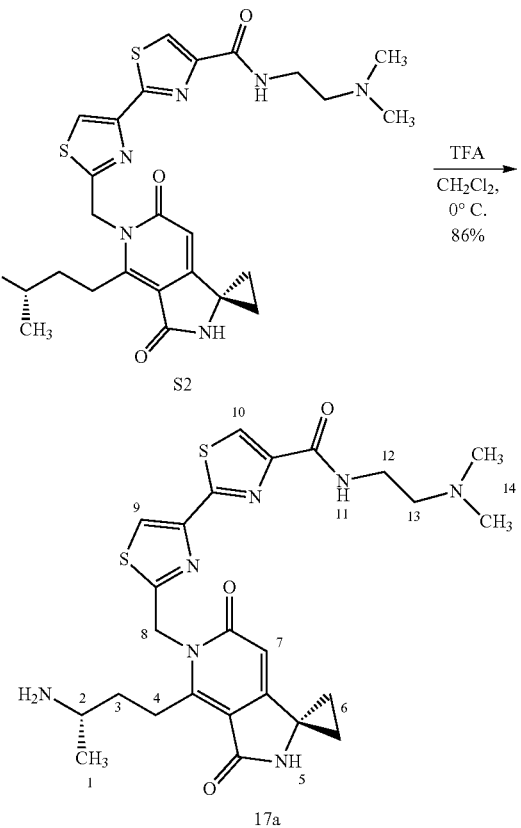

Trifluoroacetic acid (206 µL, 2.69 mmol, 120 equiv) was added dropwise via syringe to a solution of the amide S2 (14.4 mg, 22.4 µmol, 1 equiv) in dichloromethane (560 µL) at 0° C. The reaction mixture was stirred for 14 h at 0° C. The reaction mixture was concentrated. The concentrated product mixture was diluted with chloroform (10 mL). The diluted product mixture was poured into a separatory funnel that had been charged with saturated aqueous sodium bicarbonate solution (5.0 mL) and the layers that formed were separated. The aqueous layer was extracted with chloroform (2×10 mL). The organic layers were combined and the combined organic layers were dried over sodium sulfate. The dried solution was filtered and the filtrate was concentrated to provide the amide 17a as a white solid (10.5 mg, 86%). The product so obtained was used without further purification. $^1$H NMR (400 MHz, CD$_3$OD) δ 8.24 (s, 1H, H$_{10}$), 8.18 (s, 1H, H$_9$), 6.19 (s, 1H, H$_7$), 5.73 (d, J=15.4 Hz, 1H, H$_8$), 5.68 (d, J=15.5 Hz, 1H, H$_8$), 3.75-3.62 (m, 1H, H$_4$), 3.60-3.50 (m, 3H, H$_4$, H$_{12}$), 3.10-3.02 (m, 1H, H$_2$), 2.59 (t, J=6.7 Hz, 2H, H$_{13}$), 2.32 (s, 6H, H$_{14}$), 1.87-1.72 (m, 2H, H$_3$), 1.58-1.50 (m, 2H, H$_6$), 1.47-1.40 (m, 2H, H$_6$), 1.18 (d, J=6.3 Hz, 3H, H$_1$). $^{13}$C NMR (151 MHz, CD$_3$OD) δ 169.5 (C), 167.5 (C), 165.0 (C), 163.7 (C), 163.4 (C), 162.5 (C), 154.9 (C), 151.7 (C), 149.1 (C), 125.2 (CH), 120.2 (CH), 112.3 (C), 104.4 (CH), 59.3 (CH$_2$), 47.7 (CH), 46.1 (CH$_2$), 45.5 (CH$_3$), 41.5 (C), 39.0 (CH$_2$), 38.0 (CH$_2$), 25.5 (CH$_2$), 22.5 (CH$_3$), 16.3 (CH$_2$). IR (ATR-FTIR), cm$^{-1}$: 3355 (br w), 2956 (w), 1691 (w), 1648 (s), 1572 (w), 1545 (w), 1288 (m), 568 (m). HRMS-CI (m/z): [M+H]$^+$ calcd for C$_{25}$H$_{32}$N$_7$O$_3$S$_2$, 542.2003; found, 542.2004. [α]$_D^{20}$ −13.0 (c 1.0, CH$_3$OH).

Synthesis of the Amide S3:

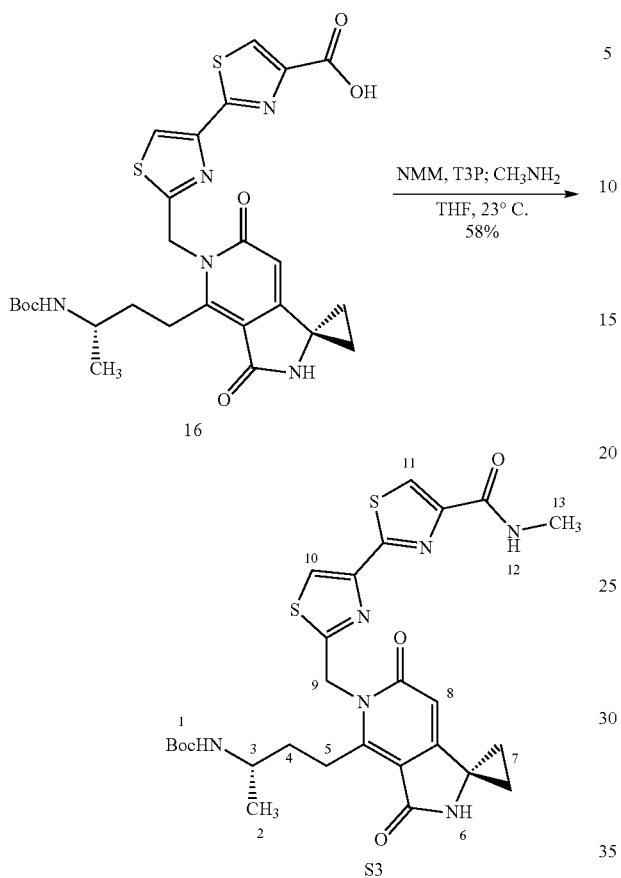

A solution of T3P in ethyl acetate (50 wt %, 54.7 µL, 91.8 µmol, 1.50 equiv) and 4-methylmorpholine (33.7 µL, 306 µmol, 5.00 equiv) were added in sequence to a solution of the acid 16 (35.0 mg, 61.2 µmol, 1 equiv) in tetrahydrofuran (790 µL) at 23° C. A solution of methylamine in tetrahydrofuran (2.00 M, 77 µL, 153 µmol, 2.50 equiv) was then added to the reaction mixture. The resulting mixture was stirred for 7 h at 23° C. The product mixture was concentrated. The concentrated product mixture was diluted with ethyl acetate (10 mL). The diluted product mixture was poured into a separatory funnel that had been charged with saturated aqueous sodium bicarbonate solution (5.0 mL) and the layers that formed were separated. The aqueous layer was extracted with ethyl acetate (2×10 mL). The organic layers were combined and the combined organic layers were dried over sodium sulfate. The dried solution was filtered and the filtrate was concentrated to provide the amide S3 as a white solid (20.8 mg, 58%). The product so obtained was used without further purification. $^1$H NMR (600 MHz, CD$_3$OD) δ 8.22 (s, 1H, H$_{11}$), 8.16 (s, 1H, H$_{10}$), 6.16 (s, 1H, H$_8$), 5.71 (d, J=15.8 Hz, 1H, H$_9$), 5.65 (d, J=15.8 Hz, 1H, H$_9$), 3.74 (app h, J=6.4 Hz, 1H, H$_3$), 3.60-3.50 (m, 2H, H$_5$), 2.96 (s, 3H, H$_{13}$), 1.89-1.75 (m, 2H, H$_4$), 1.54-1.51 (m, 2H, H$_7$), 1.43-1.40 (m, 2H, H$_7$), 1.37 (s, 9H, H$_1$), 1.17 (d, J=6.7 Hz, 3H, H$_2$). $^{13}$C NMR (151 MHz, CD$_3$OD) δ 169.4 (C), 167.4 (C), 164.9 (C), 164.0 (C), 163.7 (C), 162.5 (C), 157.9 (C), 155.1 (C), 151.8 (C), 149.3 (C), 124.9 (CH), 119.8 (CH), 112.2 (C), 104.3 (CH), 79.9 (C), 47.8 (CH), 45.9 (CH$_2$), 41.5 (C), 36.8 (CH$_2$), 28.9 (CH$_3$), 26.3 (CH$_3$), 25.9 (CH$_2$), 21.2 (CH$_3$), 16.3 (CH$_2$). IR (ATR-FTIR), cm$^{-1}$: 3284 (br w), 2971 (w), 1694 (m), 1652 (s), 1573 (m), 1550 (m), 1167 (m), 570 (s). HRMS-CI (m/z): [M+H]$^+$ calcd for C$_{27}$H$_{33}$N$_6$O$_5$S$_2$, 585.1948; found, 585.1948. [α]$_D^{20}$ −101.2 (c 0.85, CH$_3$OH).

Synthesis of the Amide 17b:

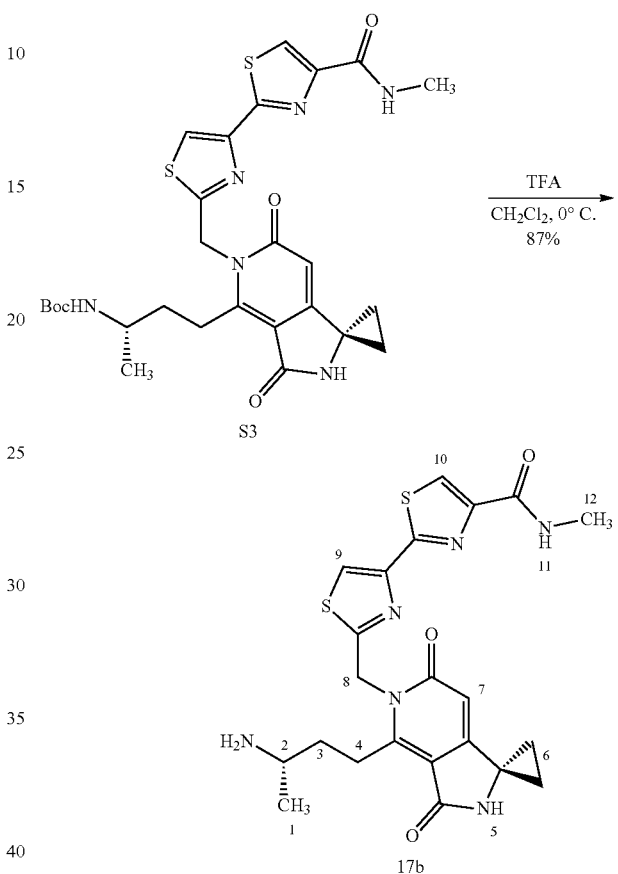

Trifluoroacetic acid (273 µL, 3.57 mmol, 120 equiv) was added dropwise via syringe to a solution of the amide S3 (17.4 mg, 29.8 µmol, 1 equiv) in dichloromethane (740 µL) at 0° C. The reaction mixture was stirred for 14 h at 0° C. The reaction mixture was concentrated. The concentrated product mixture was diluted with chloroform (10 mL). The diluted product mixture was poured into a separatory funnel that had been charged with saturated aqueous sodium bicarbonate solution (5.0 mL) and the layers that formed were separated. The aqueous layer was extracted with chloroform (2×10 mL). The organic layers were combined and the combined organic layers were dried over sodium sulfate. The dried solution was filtered and the filtrate was concentrated to provide the amide 17b as a white solid (12.6 mg, 87%). The product so obtained was used without further purification.

$^1$H NMR (600 MHz, CD$_3$OD) δ 8.24 (s, 1H, H$_9$), 8.16 (s, 1H, H$_{10}$), 6.21 (s, 1H, H$_7$), 5.72 (d, J=15.7 Hz, 1H, H$_8$), 5.67 (d, J=15.7 Hz, 1H, H$_8$), 3.74-3.65 (m, 1H, H$_4$), 3.62-3.51 (m, 1H, H$_4$), 3.31-3.26 (m, 1H, H$_2$), 2.96 (s, 3H, H$_{12}$), 2.04-1.86 (m, 2H, H$_3$), 1.58-1.50 (m, 2H, H$_6$), 1.48-1.41 (m, 2H, H$_6$), 1.30 (d, J=6.6 Hz, 3H, H$_1$). $^{13}$C NMR (151 MHz, CD$_3$OD) δ 169.6 (C), 167.3 (C), 164.8 (C), 164.0 (C), 163.7 (C), 162.3 (C), 153.7 (C), 151.8 (C), 149.1 (C), 124.8 (CH), 120.3 (CH), 112.5 (C), 104.8 (CH), 48.1 (CH), 46.0 (CH$_2$), 41.6 (C), 36.4 (CH$_2$), 26.4 (CH$_3$), 25.0 (CH$_2$), 20.3 (CH$_3$), 16.4 (CH$_2$). IR (ATR-FTIR), cm$^{-1}$: 3419 (br w), 2926 (w), 2857 (w), 1688 (w), 1647 (s), 1556 (m), 1289 (w), 568 (m). HRMS-CI (m/z): [M+H]$^+$ calcd for C$_{22}$H$_{25}$N$_6$O$_3$S$_2$, 485.1424; found, 485.1425. [α]$_D^{20}$ −29.0 (c 1.0, CH$_3$OH).

Synthesis of Amide S4:

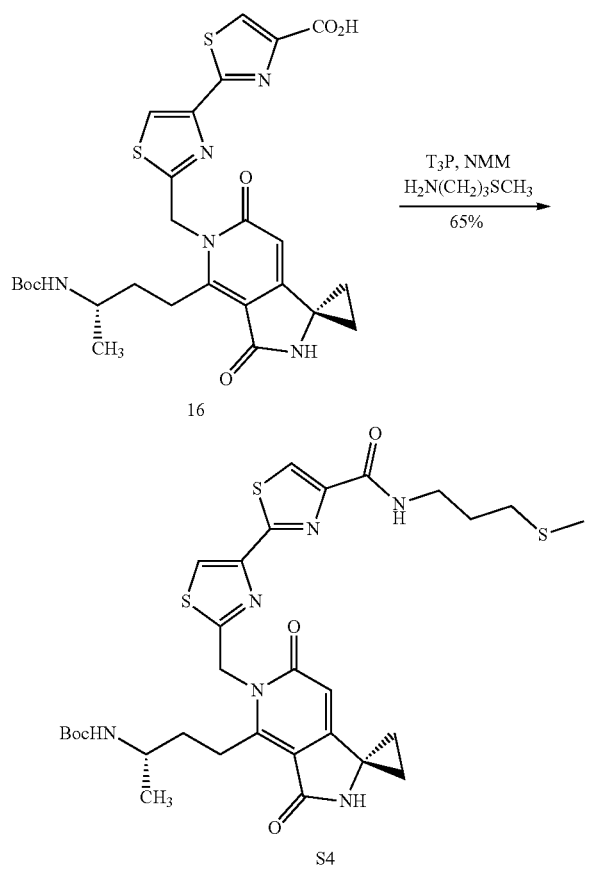

Synthesis of S5:

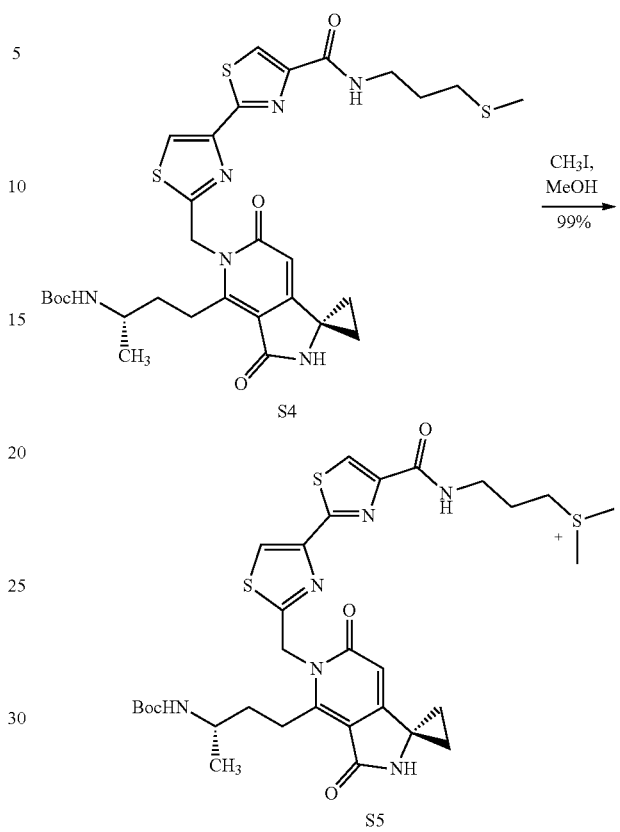

A solution of T$_3$P in ethyl acetate (50 wt %, 0.15 mL, 0.50 mmol, 5.00 equiv) and 4-methylmorpholine (54.8 µL, 0.50 mmol, 5.00 equiv) were added in sequence to a solution of the acid 16 (57.0 mg, 99.7 µmol, 1 equiv) in tetrahydrofuran (2.50 mL) at 23° C. 3-(Methylthio)propylamine (55.9 µL, 0.50 mmol, 5.00 equiv) was then added to the reaction mixture. The resulting mixture was stirred for 12 h at 23° C. The product mixture was concentrated. The concentrated product mixture was diluted with ethyl acetate (10 mL). The diluted product mixture was poured into a separatory funnel that had been charged with saturated aqueous sodium bicarbonate solution (5.0 mL) and the layers that formed were separated. The aqueous layer was extracted with ethyl acetate (2×10 mL). The organic layers were combined and the combined organic layers were dried over sodium sulfate. The dried solution was filtered and the filtrate was concentrated to provide the amide as a white solid (42.7 mg, 65%). The compound S4 could be deprotected (removal of BOC group) using the methods described for the other compounds to produce compound 17c (FIG. 1). $^1$H NMR (400 MHz, CD$_3$OD) δ 8.23 (s, 1H), 8.17 (s, 1H), 6.16 (s, 1H), 5.71 (d, J=15.8 Hz, 1H), 5.65 (d, J=15.7 Hz, 1H), 3.74 (p, J=7.3 Hz, 1H), 3.66-3.51 (m, 1H), 3.51 (t, J=6.9 Hz, 2H), 2.57 (t, J=7.2 Hz, 2H), 2.10 (s, 3H), 1.92 (p, J=7.1 Hz, 2H), 1.87-1.72 (m, 1H), 1.55-1.50 (m, 2H), 1.44-1.39 (m, 4H), 1.37 (s, 9H), 1.17 (d, J=6.5 Hz, 3H).

To a solution of the amide (18.9 mg, 28.0 µmol, 1 equiv) in anhydrous methanol (660 µL) at 23° C. was added iodomethane (0.24 mL, 3.93 mmol, 138 equiv). The resulting mixture was stirred for 12 h at 23° C. The mixture was concentrated to provide the product as a white solid (22.5 mg, 99%). The compound S4 could be deprotected (removal of BOC group) using the methods described for the other compounds to provide compound 17d.

$^1$H NMR (400 MHz, CD$_3$OD) δ 8.25 (s, 1H), 8.21 (s, 1H), 6.16 (s, 1H), 5.72 (d, J=15.9 Hz, 1H), 5.65 (d, J=15.7 Hz, 1H), 3.74 (p, J=6.5 Hz, 1H), 3.60 (t, J=6.4 Hz, 2H), 3.59-3.50 (m, 1H), 3.40 (t, J=7.5 Hz, 2H), 2.96 (s, 6H), 2.16 (t, J=7.3 Hz, 2H), 1.85-1.77 (m, 1H), 1.53 (q, J=5.3, 4.5 Hz, 2H), 1.45-1.36 (m, 4H), 1.38 (s, 9H), 1.17 (d, J=6.6 Hz, 3H).

Biological Experiments

Anti-Cancer Activity

Compounds to be tested for anti-cancer activity were submitted dry, dissolved to 10 mM stocks in DMSO, and stored protected from light at −80° C. until use. DMSO vehicle control wells, and 3 fold serial dilutions of compounds from 10 mM to 6.2 nM were prepared in 384 well plates. Kinamycin and tamoxifen were also added as controls in this manner.

LN2 aliquots of cancer cells (indicated in the tables of FIGS. 3 and 4) were cultured at YCMD and plated in Corning 3707 TC plates at 400 cells/well initial seeding density in 20 uL of growth medium. Cells were incubated overnight at 37'C in a humidified 5% CO2 incubator, and treated with compounds.

20 nL of compound was dispensed into the assay plates using a 384-well pin tool on the Tecan Aquarius. Final assay compound treatments ranged from 10 uM to 6.2 pM, 0.1% DMSO. 10% DMSO controls or 60 uM Tamoxifen served as positive controls for toxicity. Assay plates were incubated 72 hours at 37'C in a 5% CO2 incubator.

For assay readout CellTiter-Glo (Promega) was prepared according to manufacturer's instructions and 20 uL/well was added to assay plates using a MultiDrop. Luminescence was read on an Envision plate reader (Perkin Elmer) with 0.3 second sampling time per well after a 10 min. room temperature incubation in the dark.

Analysis

Figure 3:
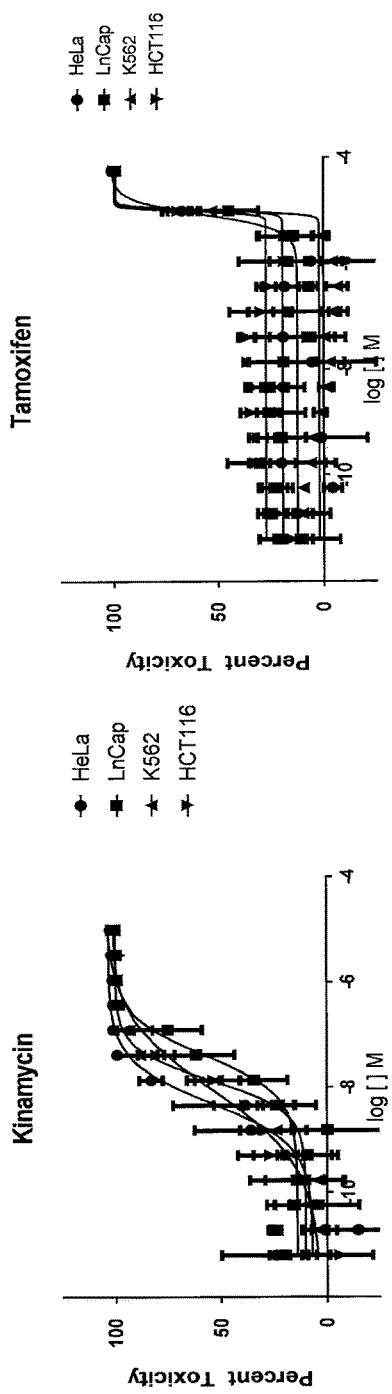
FIG. 3 shows anti-cancer activity of kinamycin and tamoxifen against several cancer cell lines as a comparison basis for assessing the anti-cancer activity of compounds according to the present invention.
Figure 4:
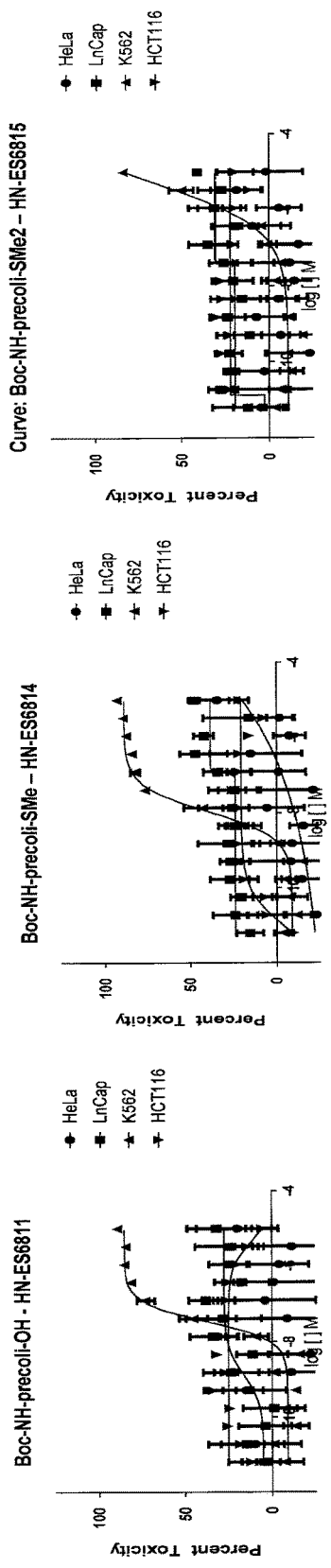
FIG. 4 shows the anti-cancer activity of certain preferred compounds according to the present invention.

Toxic effects have low luminescence signal relative to the vehicle control evidencing low toxicity. Raw data (luminescence counts per second) were normalized to percent effect by the formula: [(DMSO vehicle−POS COntrol)/(DMSO vehicle−SAMPLE)]*100. The dilution curves were run in quaruptlicate. 10% DMSO treated or 60 uM Tamoxifen wells are Positive controls (100% (toxicity), and DMSO vehicle (0.1% DMSO) wells are Negative controls 0% effect (no toxicity). 24 positive and 24 negative control wells were run on every plate. The date was plotted in GraphPad Prism using a variable slope 4-parameter fit. 4 parameters are lower baseline (~0% effect), upper baseline (~100% effect), inflection point ($IC_{50}$) and Hill slope. FIG. 3, Table 1 shows the anti-cancer impact of Kinamycin and Tamoxifen on cancer cell lines tested. In most instances, these compounds inhibited cancer cell growth at $ED_{50}$ values ranging from approximately 10-5 to about 5×10-9. FIG. 4, Table 2 shows the anti-cancer impact of compounds according to the present invention where the compounds evidenced substantial anti-cancer activity within the range of approximately $5.5 \times 10^{-5}$ to approximately $1 \times 10^{-8}$. More specifically, compound 17a showed anti-cancer activity at 35 nM and compound S4 showed anti-cancer activity at 11 nM.

The invention claimed is:

1. A compound according to the chemical structure I:

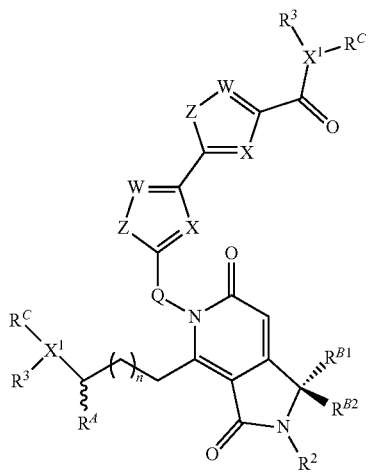

Where X is N and W is C—$R^1$;
Each Z is S or CR(R);

Each R is independently H, a $C_1$-$C_3$ alkyl group optionally substituted with one or two hydroxyl groups or up to three halogen groups or a O—($C_1$-$C_3$) alkoxy group;

Q is C($R^Q$)$R^Q$;

Each $X^1$ is N;

$R^A$ is H or an optionally substituted $C_1$-$C_8$ alkyl or alkene group;

Each $R^Q$ is independently H or a $C_1$-$C_3$ alkyl group which is optionally substituted with one or two hydroxyl groups or up to three halogen groups;

$R^1$ and $R^2$ are each independently H or a $C_1$-$C_3$ alkyl group which is optionally substituted with one or two hydroxyl groups or up to three halogen groups;

Each $R^3$ is independently H, a $C_1$-$C_6$ alkyl group optionally substituted with 1 or 2 hydroxyl groups or up to three halogen groups, a protecting group $P_G$ or a targeting element $T_E$ which is linked to $X^1$ through a linker $L_C$ which is optionally cleavable, wherein said targeting element $T_E$ is a small molecule which binds to a folate receptor, a monoclonal antibody or antibody fragment (FAB), a PSMA binding moiety, a YSA peptide which binds to Ephrin A2, a low pH insertion peptide, a group according to the chemical structure

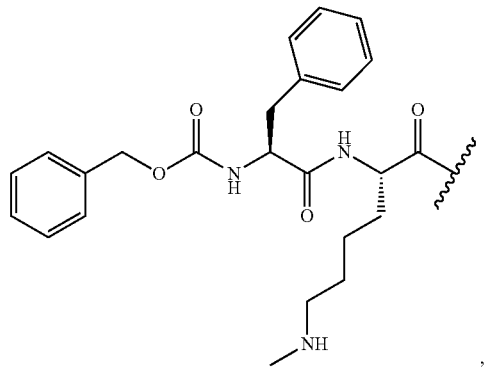 [SMILES: *C(=O)[C@H](CCCCNC)NC(=O)[C@H](Cc1ccccc1)NC(=O)OCc1ccccc1]

or a cysteine-cathepsin moiety;

n is 0, 1, 2, 3, or 4;

$R^{B1}$ and $R^{B2}$ are each independently H, a $C_1$-$C_3$ alkyl group which is optionally substituted with one or two hydroxyl groups or up to three halo groups or together $R^{B1}$ and $R^{B2}$ form a cyclopropyl or cyclobutyl group;

Each $R^C$ is independently H, a $C_1$-$C_{12}$ optionally substituted alkyl or alkene group, a $C_1$-$C_{12}$ optionally substituted acyl group or a $C_2$-$C_{12}$ optionally substituted ester group, a —$(CH_2)_{n1}NR_1R_2$ or a —$(CH_2)_{n1}SR_SR_{S1}$ group where $R_S$ is absent or a $C_1$-$C_6$ optionally substituted alkyl group and $R_1$, $R_2$ and $R_{S1}$ are each independently H or a $C_1$-$C_6$ optionally substituted alkyl group, a protecting group $P_G$ or a targeting element $T_E$ as described above which is linked to the nitrogen through a linker $L_C$ which is optionally cleavable, and n1 is 1-8, or $R^C$ forms a dimer compound through a linker group, the dimer compound according to the general chemical structure(s):

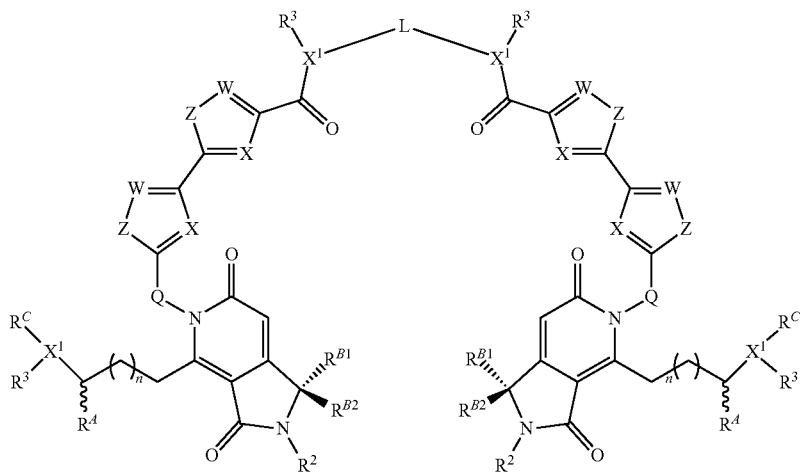

or

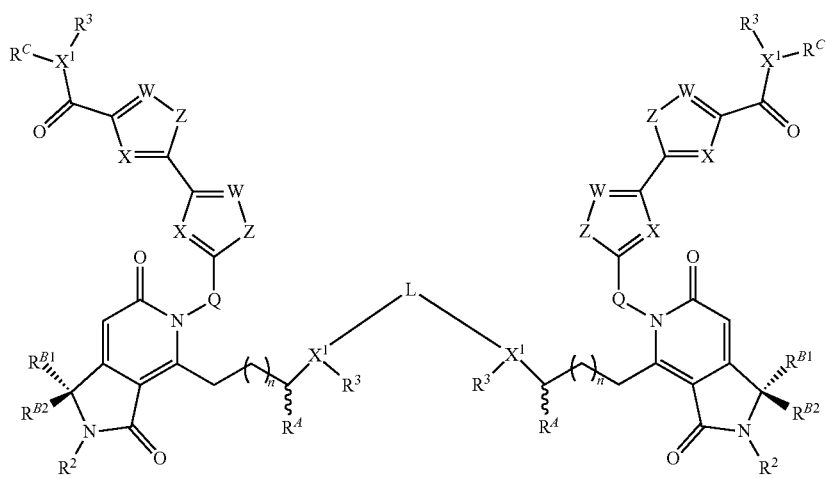

Where each of X, W, Z, $R^2$, $R^3$, $R^A$, n, $R^{B1}$, $R^{B2}$, and $X^1$ is the same for compound I as above;

$R^C$ is independently H, a $C_1$-$C_{12}$ optionally substituted alkyl or alkene group, a $C_1$-$C_{12}$ optionally substituted acyl or ester group, a —$(CH_2)_{n1}NR_1R_2$ or a —$(CH_2)_{n1}SR_SR_{S1}$ group where $R_S$ is absent or a $C_1$-$C_6$ optionally substituted alkyl group and $R_1$, $R_2$ and $R_{S1}$ are each independently H or a $C_1$-$C_6$ optionally substituted alkyl group, a protecting group $P_G$ or a targeting element $T_E$ as described above which is linked to the nitrogen through a linker $L_C$ which is optionally cleavable, and n1 is 1-8; and L is a linker group which covalently links the dimeric portions of the molecule to each other, or a pharmaceutically acceptable salt, stereoisomer, solvate or polymorph thereof.

2. A compound of claim 1 according to the chemical structure II:

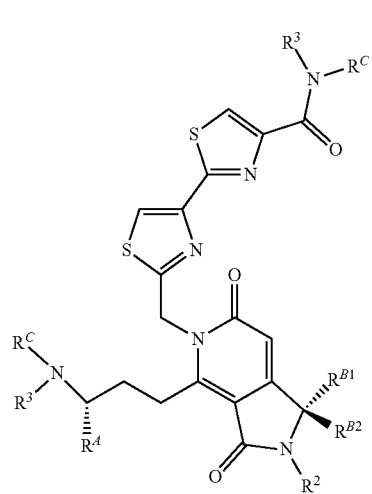

Where $R^A$ is H or a $C_1$-$C_3$ alkyl;

$R^2$ is H or a $C_1$-$C_3$ alkyl group which is optionally substituted with one or two hydroxyl groups or up to three halogen groups;

Each $R^3$ is independently H, a $C_1$-$C_6$ alkyl group optionally substituted with 1 or 2 hydroxyl groups or up to three halogen groups, a protecting group $P_G$ or a targeting element $T_E$ which is linked to the adjacent nitrogen through an optionally cleavable linker Lc, wherein said targeting element $T_E$ is a small molecule which binds to a folate receptor, a monoclonal antibody or antibody fragment (FAB), a PSMA binding moiety, a YSA peptide which binds to Ephrin A2, a low pH insertion peptide, a group according to the chemical structure

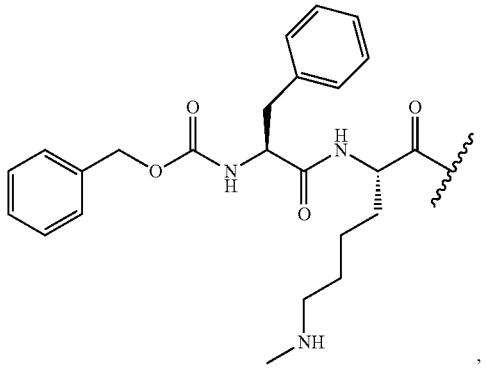 [SMILES: *C(=O)[C@H](CCCCNC)NC(=O)[C@H](Cc1ccccc1)NC(=O)OCc1ccccc1]

or a cysteine-cathepsin moiety;

$R^{B1}$ and $R^{B2}$ are each independently H, a $C_1$-$C_3$ alkyl group which is optionally substituted with one or two hydroxyl groups or up to three halo groups or together $R^{B1}$ and $R^{B2}$ form a cyclopropyl or cyclobutyl group;

Each $R^C$ is independently H, a $C_1$-$C_{12}$ alkyl or alkene group which is optionally substituted with one or two hydroxyl groups and up to five halo groups, a $C_1$-$C_{12}$ optionally substituted acyl group, a $C_2$-$C_{12}$ optionally substituted ester group, or a —$(CH_2)_{n1}NR_1R_2$ or a —$(CH_2)_{n1}SR_SR_{S1}$ group where $R_S$ is absent or a $C_1$-$C_6$ optionally substituted alkyl group and $R_1$, $R_2$ and $R_{S1}$ are each independently H or a $C_1$-$C_6$ optionally substituted alkyl group or $R^C$ is a protecting group $P_G$ or a targeting element $T_E$ as described above which is linked to the nitrogen through an optionally cleavable linker $L_C$, and n1 is 1-8, or $R^C$ forms a dimer compound through a linker group, the dimer compound according to the chemical structure(s):

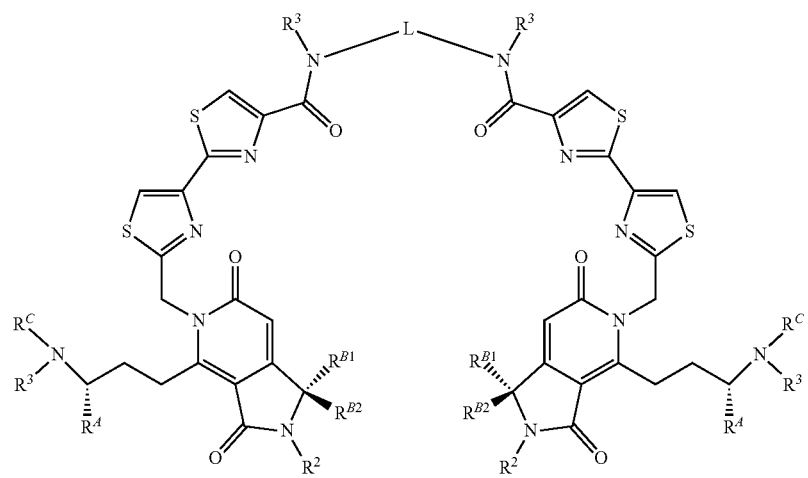

or

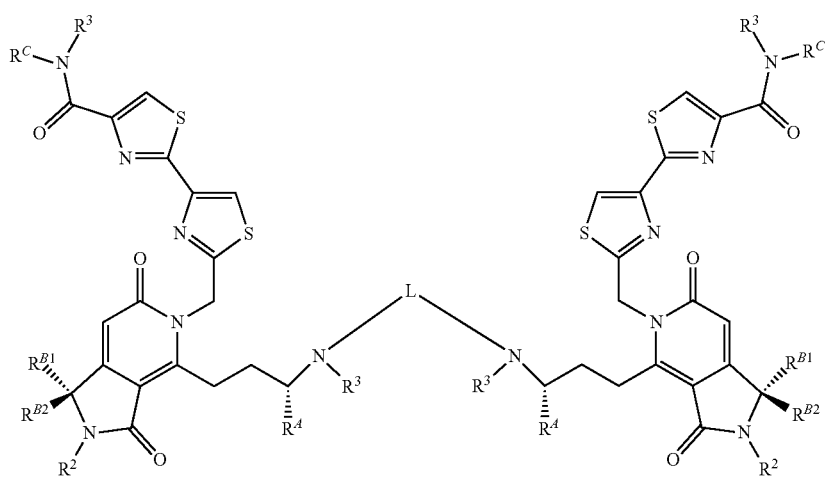

Where $R^A$, $R^2$, $R^3$, $R^{B1}$ and $R^{B2}$ are the same as for compound II above;

$R^C$ is independently H, a $C_1$-$C_{12}$ optionally substituted alkyl or alkene group, a $C_1$-$C_{12}$ optionally substituted acyl group, a $C_2$-$C_{12}$ optionally substituted ester group, a —$(CH_2)_{n1}NR_1R_2$ or a —$(CH_2)_{n1}SR_SR_{S1}$ group where $R_S$ is absent or a $C_1$-$C_6$ optionally substituted alkyl group and $R_1$, $R_2$ and $R_{S1}$ are each independently H or a $C_1$-$C_6$ optionally substituted alkyl group, a protecting group $P_G$ or a targeting element $T_E$ as described above which is linked to the nitrogen through a linker $L_C$ which is optionally cleavable, and n1 is 1-8; and L is a linker group which covalently links the dimeric portions of the molecule to each other, or a pharmaceutically acceptable salt, stereoisomer, solvate or polymorph thereof.

3. The compound according to claim 1 wherein Z is S; W is C—H; R is H, methyl or OMe; $R^A$ is H or methyl; $R^1$ and $R^2$ are each independently H or methyl; $R^3$ H, methyl, a ter-butyloxycarbonyl (BOC) protecting group or a targeting element $T_E$, $R^{B1}$ and $R^{B2}$ are each independently H, methyl or together form a cyclopropyl group and $R^C$ is H, methyl, a $C_1$-$C_{12}$ optionally substituted acyl group, a $C_2$-$C_{12}$ optionally substituted ester group, a —$(CH_2)_{n1}$—$(CH_3)_2$ group, a —$(CH_2)_{n1}$—$SCH_3$ group or a —$(CH_2)_{n1}$—$S^\oplus(CH_3)_2$ group where n1 is 1, 2, 3 or 4 or no more than one $R^C$ forms a dimer compound through linker L where L is a —$(CH_2)_mN(R)(CH_2)_m$— group where R is H or a $C_1$-$C_3$ alkyl group and each m is independently an integer from 1-12, or a pharmaceutically acceptable salt, stereoisomer, solvate or polymorph thereof.

4. The compound according to claim 2 wherein $R^A$ is H or methyl; $R^2$ is H or methyl; $R^3$ is H, methyl, a ter-butyloxycarbonyl (BOC) protecting group $P_G$ or a targeting element $T_E$ which is linked to the adjacent nitrogen through a linker $L_C$; $R^{B1}$ and $R^{B2}$ are each independently H, methyl or together form a cyclopropyl group and $R^C$ is H, methyl, a $C_1$-$C_{12}$ optionally substituted acyl group, a $C_2$-$C_{12}$ optionally substituted ester group, a —$(CH_2)_{n1}$—$N(CH_3)_2$ group, a —$(CH_2)_{n1}$—$SCH_3$ group or a —$(CH_2)_{n1}$—$S^\oplus(CH_3)_2$ group where n1 is 1, 2, 3 or 4 or one $R^C$ forms a dimer compound through linker L where L is a —$(CH_2)_mN(R)(CH_2)_m$— group where R is H or a $C_1$-$C_3$ alkyl group (preferably H or methyl) and each m is independently from 1-10, or a pharmaceutically acceptable salt, stereoisomoer, solvate or polymorph thereof.

5. A compound of claim 1 according to the chemical structure:

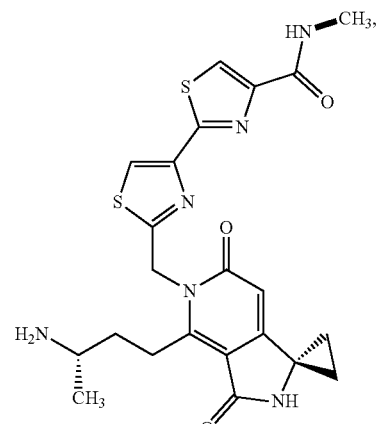

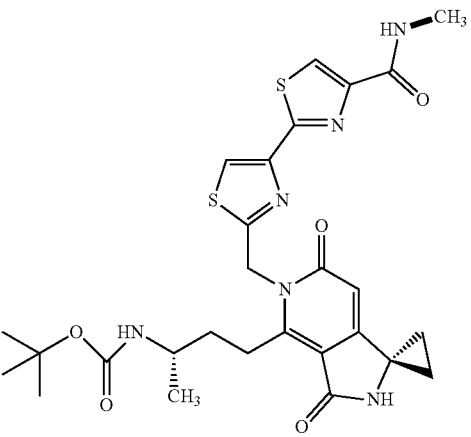

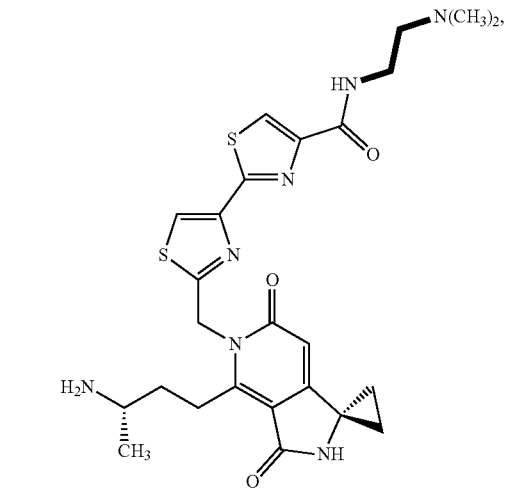
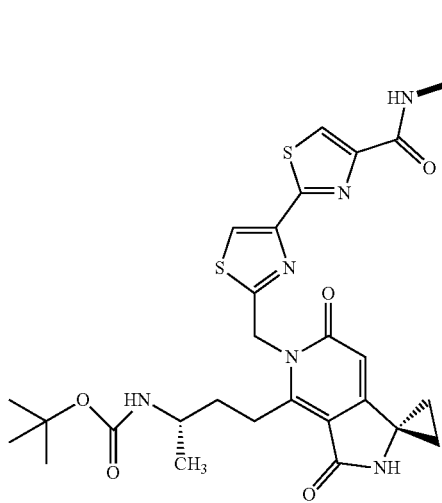
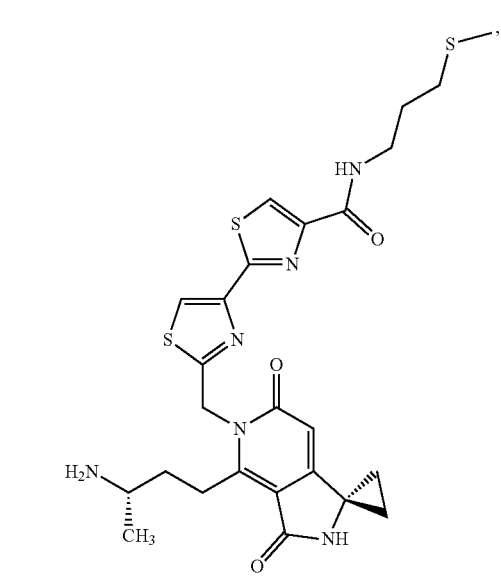
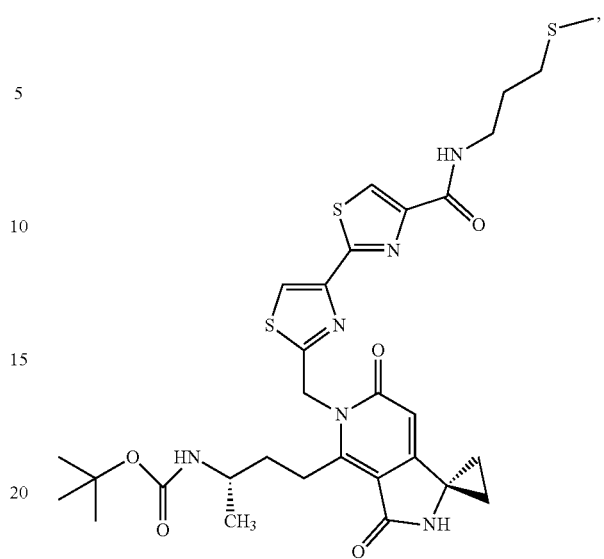
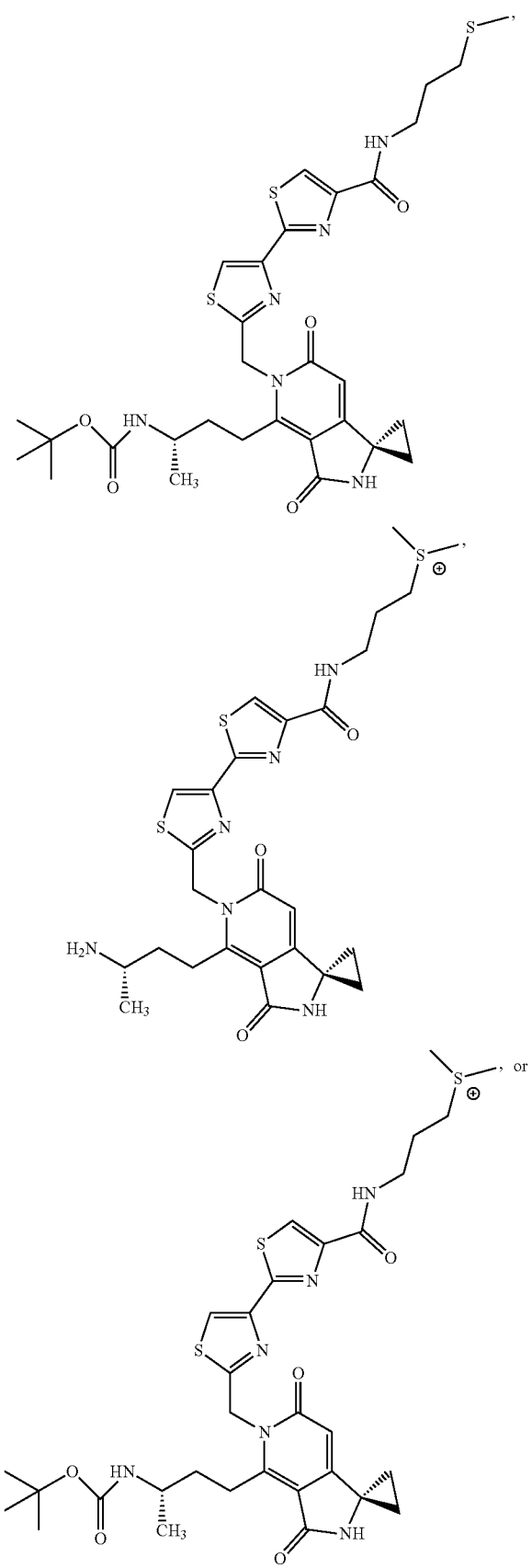

a pharmaceutically acceptable salt, stereoisomer, solvate or polymorph thereof.

6. A compound of claim 1 according to the chemical structure:

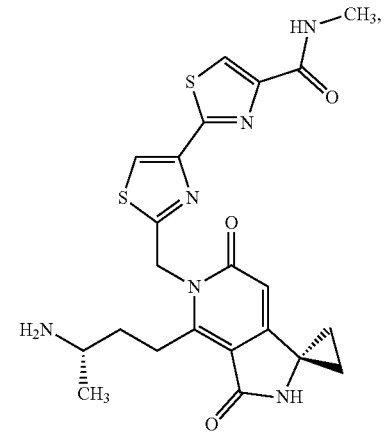

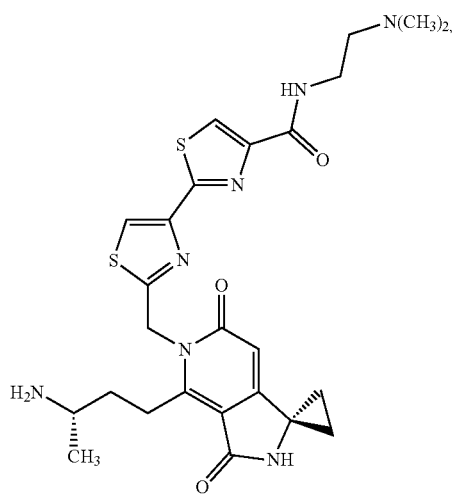

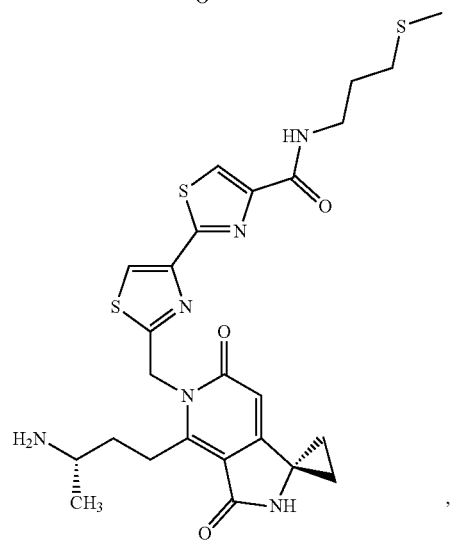

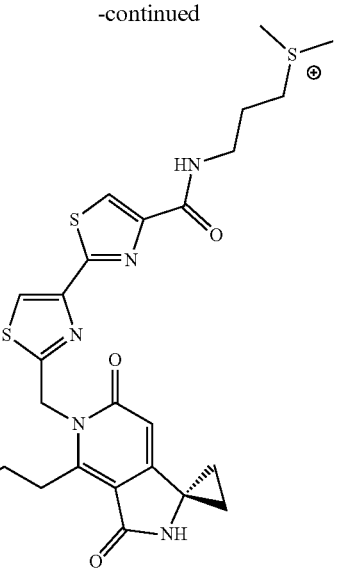

, or a pharmaceutically acceptable salt, stereoisomer, solvate or polymorph thereof.

7. A pharmaceutical composition comprising an anti-cancer effective amount of a compound according to claim 1 in combination with a pharmaceutically acceptable carrier, additive or excipient.

8. The compound according to claim 1 wherein $R^3$ is H or methyl, $R^C$ is H, methyl, $-(CH_2)_{n1}NR_1R_2$ or a $-(CH_2)_{n1}SR_SR_{S1}$ group where $R_S$ is absent or a $C_1$-$C_6$ optionally substituted alkyl group and $R_1$, $R_2$ and $R_{S1}$ are each independently H or a $C_1$-$C_6$ alkyl group and n1 is an integer from 1-6.

9. The compound according to claim 2 wherein $R^3$ is H or methyl, $R^C$ is H, methyl, $-(CH_2)_{n1}NR_1R_2$ or a $-(CH_2)_{n1}SR_SR_{S1}$ group where $R_S$ is absent or a methyl group and $R_1$, $R_2$ and $R_{S1}$ are each independently H or a $C_1$-$C_6$ alkyl group and n1 is an integer from 1-6.

10. The compound according to claim 3 wherein $R^3$ is H or methyl, $R^C$ is H, methyl, $-(CH_2)_{n1}NR_1R_2$ or a $-(CH_2)_{n1}SR_SR_{S1}$ group where $R_S$ is absent or a methyl group and $R_1$, $R_2$ and $R_{S1}$ are each independently H or a $C_1$-$C_6$ alkyl group and n1 is an integer from 1-6.

11. The compound according to claim 4 wherein $R^3$ is H or methyl, $R^C$ is H, methyl, $-(CH_2)_{n1}NR_1R_2$ or a $-(CH_2)_{n1}SR_SR_{S1}$ group where $R_S$ is absent or a methyl group and $R_1$, $R_2$ and $R_{S1}$ are each independently H or a $C_1$-$C_6$ alkyl group and n1 is an integer from 1-6.

12. The compound according to claim 1 wherein $R^3$ is H or methyl, $R^C$ is H, methyl, $-(CH_2)_{n1}NR_1R_2$ or a $-(CH_2)_{n1}SR_SR_{S1}$ group where $R_S$ is absent or a methyl group, $R_{S1}$ is H or a methyl group, $R_1$ and $R_2$ are each independently H or a $C_1$-$C_3$ alkyl group and n1 is an integer from 1-6.

13. The compound according to claim 2 wherein $R^3$ is H or methyl, $R^C$ is H, methyl, $-(CH_2)_{n1}NR_1R_2$ or a $-(CH_2)_{n1}SR_SR_{S1}$ group where $R_S$ is absent or a methyl group, $R_{S1}$ is H or a methyl group, $R_1$ and $R_2$ are each independently H or a $C_1$-$C_3$ alkyl group and n1 is an integer from 1-6.

14. The compound according to claim 3 wherein $R^3$ is H or methyl, $R^C$ is H, methyl, $-(CH_2)_{n1}NR_1R_2$ or a $-(CH_2)_{n1}SR_SR_{S1}$ group where $R_S$ is absent or a methyl group, $R_{S1}$ is H or a methyl group, $R_1$ and $R_2$ are each independently H or a $C_1$-$C_3$ alkyl group and n1 is an integer from 1-6.

15. The compound according to claim 4 wherein $R^3$ is H or methyl, $R^C$ is H, methyl, —$(CH_2)_{n1}NR_1R_2$ or a —$(CH_2)_{n1}SR_SR_{S1}$ group where $R_S$ is absent or a methyl group, $R_{S1}$ is H or a methyl group, $R_1$ and $R_2$ are each independently H or a $C_1$-$C_3$ alkyl group and n1 is an integer from 1-6.

16. A pharmaceutical composition comprising an anticancer effective amount of a compound according to claim 8 in combination with a pharmaceutically acceptable carrier, additive or excipient.

17. A pharmaceutical composition comprising an anticancer effective amount of a compound according to claim 9 in combination with a pharmaceutically acceptable carrier, additive or excipient.

18. A pharmaceutical composition comprising an anticancer effective amount of a compound according to claim 10 in combination with a pharmaceutically acceptable carrier, additive or excipient.

19. A pharmaceutical composition comprising an anticancer effective amount of a compound according to claim 11 in combination with a pharmaceutically acceptable carrier, additive or excipient.

20. A compound according to the chemical structure I:

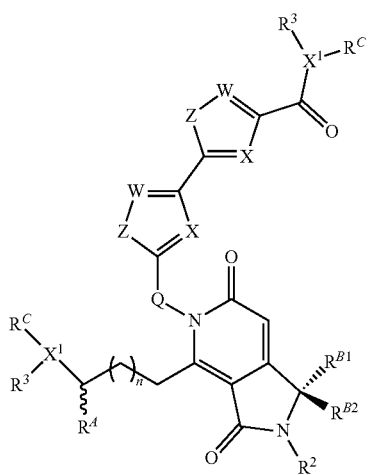

Where X is N and W is C—$R^1$;
Each Z is S;
Each R is independently H, a $C_1$-$C_3$ alkyl group optionally substituted with one or two hydroxyl groups or up to three halogen groups or a O—($C_1$-$C_3$) alkoxy group;

Q is $C(R^Q)R^Q$;
Each $X^1$ is N;
$R^A$ is H or a $C_1$-$C_8$ alkyl or alkene group;
Each $R^Q$ is independently H or a $C_1$-$C_3$ alkyl group which is optionally substituted with one or two hydroxyl groups or up to three halogen groups;
$R^1$ and $R^2$ are each independently H or a $C_1$-$C_3$ alkyl group which is optionally substituted with one or two hydroxyl groups or up to three halogen groups;
Each $R^3$ is independently H, a $C_1$-$C_6$ alkyl group optionally substituted with 1 or 2 hydroxyl groups or up to three halogen groups or a protecting group $P_G$,
n is 0, 1, 2, 3, or 4;
$R^{B1}$ and $R^{B2}$ are each independently H, a $C_1$-$C_3$ alkyl group which is optionally substituted with one or two hydroxyl groups or up to three halo groups or together $R^{B1}$ and $R^{B2}$ form a cyclopropyl or cyclobutyl group;
Each $R^C$ is independently H, a $C_1$-$C_{12}$ alkyl or alkene group which is optionally substituted with one or two hydroxyl groups and up to five halo groups, a $C_1$-$C_{12}$ acyl group or a $C_2$-$C_{12}$ ester group, a —$(CH_2)_{n1}NR_1R_2$ or a —$(CH_2)_{n1}SR_SR_{S1}$ group where $R_S$ is absent or a $C_1$-$C_6$ alkyl group and $R_1$, $R_2$ and $R_{S1}$ are each independently H or a $C_1$-$C_6$ alkyl group or a protecting group $P_G$, and n1 is 1-8, or
a pharmaceutically acceptable salt, stereoisomer, solvate or polymorph thereof.

21. The compound according to claim 20 wherein $R^3$ is H or methyl, $R^C$ is H, methyl, —$(CH_2)_{n1}NR_1R_2$ or a —$(CH_2)_{n1}SR_SR_{S1}$ group where $R_S$ is absent or a methyl group, $R_{S1}$ is H or a methyl group, $R_1$ and $R_2$ are each independently H or a $C_1$-$C_3$ alkyl group and n1 is an integer from 1-6.

22. A pharmaceutical composition comprising an anticancer effective amount of a compound according to claim 20 in combination with a pharmaceutically acceptable carrier, additive or excipient.

23. A pharmaceutical composition comprising an anticancer effective amount of a compound according to claim 21 in combination with a pharmaceutically acceptable carrier, additive or excipient.

24. A pharmaceutical composition comprising an anticancer effective amount of a compound according to claim 5 in combination with a pharmaceutically acceptable carrier, additive or excipient.

25. A pharmaceutical composition comprising an anticancer effective amount of a compound according to claim 6 in combination with a pharmaceutically acceptable carrier, additive or excipient.

* * * * *